United States Patent [19]

Honda et al.

[11] Patent Number: 4,698,423

[45] Date of Patent: Oct. 6, 1987

[54] ELLIPTICINE DERIVATIVE AND PRODUCTION PROCESS THEREOF

[75] Inventors: Tadashi Honda; Toshihiro Nakanishi, both of Ibaraki, Japan

[73] Assignee: Suntory Limited, Osaka, Japan

[21] Appl. No.: 758,879

[22] Filed: Jul. 25, 1985

[30] Foreign Application Priority Data

Jul. 31, 1984 [JP] Japan .................................. 59-161296

[51] Int. Cl.<sup>4</sup> .................. C07D 471/02; A61K 31/475
[52] U.S. Cl. ...................................... 536/24; 514/908; 536/55; 546/70
[58] Field of Search ............................. 536/23, 24, 55; 514/908, 43; 546/70

[56] References Cited

U.S. PATENT DOCUMENTS

| | | | |
|---|---|---|---|
| 3,480,613 | 11/1969 | Walton | 536/26 |
| 4,182,859 | 1/1980 | Erhardt | 536/23 |
| 4,210,745 | 7/1980 | Montgomery | 536/24 |
| 4,310,667 | 1/1982 | Le Pecq et al. | 514/908 |
| 4,479,942 | 10/1984 | Yamashita et al. | 536/24 |

*Primary Examiner*—Ronald W. Griffin
*Attorney, Agent, or Firm*—Burns, Doane, Swecker & Mathis

[57] ABSTRACT

An ellipticine derivative having the structure:

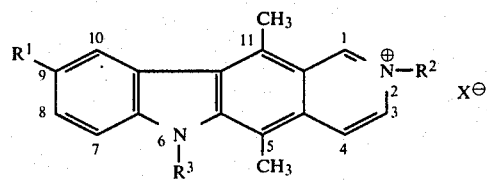

as well as process for the preparation of such ellipticine derivatives. The ellipticine derivatives have antineoplastic or antitumor activity.

20 Claims, No Drawings

ELLIPTICINE DERIVATIVE AND PRODUCTION PROCESS THEREOF

BACKGROUND OF THE INVENTION

1. Field of the Invention

The present invention relates to a novel ellipticine derivative having a strong antineoplastic or antitumor activity and, also, relates to a production process thereof.

2. Description of the Related Art

Pyridocarbazole alkaloids such as ellipticine, i.e., 5, 11-dimethyl-6H-pryrido [4,3-b] carbazole (i.e., R=H in the following general formula (A)), and 9-methoxyellipticine (i.e., R=OCH$_3$ in the following general formula (A)) are known as alkaloids contained in, for example, Aspidospermina and Ochrosia leaves.

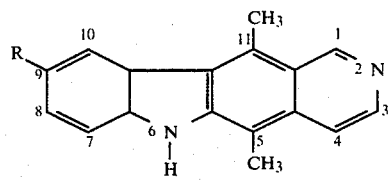

Recently, it was reported in J. Rouess'e et. al, Bull. Cancer (Paris), 68, 437–441 (1981) that 2-methyl-9-hydroxyelliptiscinium acetate (Celiptium) having the general formula (B):

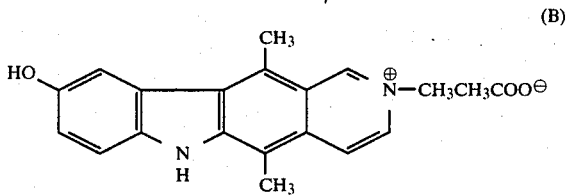

is effective against mammary cancer. It was also reported, in R.W. Guthrie et. al, J. Medicinal Chemistry, 18 (7), 755–760 (1975), that elipticine and 9-methoxyellipticine are effective against the tumor of animals used for experiments, mouse lymphoid leukemia L-1210 and Sarcoma 180 (solid) and, in Japanese Examined Patent Publication (Kokoku) No. 58-35196 and British Pat. No. 1436080, that the activity of 9-hydroxyellipticine against mouse lymphoid leukemia L-1210 is higher, by more than 100 to 1000 fold, than that of 9-methoxyellipticine.

As mentioned above, compounds having a pyridocarbazole skeleton are useful because they have an antineoplastic or antitumor activity. Various studies or research to synthesize those compounds have been reported in, for example, L.K. Dalton et. al., Aust. J. Chem., 20, 2715–2727 (1967); A.H. Jackson et. al., J. Chem. Soc. Perkin I, 1698–1704 (1977); J.Y. Lallemand et. al, Tetrahedron Letters, No. 15, 1261–1264 (1978); and European Patent Specification No. 9445. Furthermore, it is disclosed in U.S. Pat. No. 4,434,290 that compounds having certain substituents introduced into the pyridocarbazole skeleton have an activity against mouse lymphoid leukemia L-1210.

However, ellipticine, 9-methoxyellipticine, and 9-hydroxyellipticine have not been clinically used yet as an antineoplastic or antitumor agent. This is because, among other reasons, the water-solubilities of these compounds are very poor. Although Japanese Unexamined Patent Publication (Kokai) No. 58-222087 proposes the oxidation of 2-alkyl-9-hydroxyellipticinium salts to introduce amino acids, oligopeptides, nucleotides, or nucleosides into the 10-position of the skeleton. However, these compounds do not provide desirable life-prolongation effects against mouse lymphoid leukemia L-1210.

SUMMARY OF THE INVENTION

Accordingly, the objects of the present invention are to improve the above-mentioned state of the prior art and to provide novel ellipticine derivatives having a remarkable antineoplastic or antitumor activity.

Other objects and advantages of the present invention will be apparent from the following description.

In accordance with the present invention, there is provided an ellipticine derivative having the general formula (I):

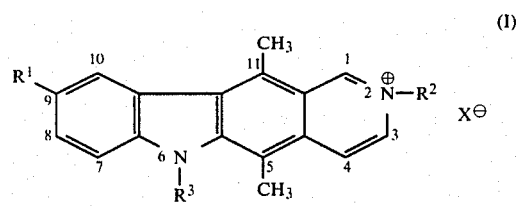

wherein
R$^1$ represents a hydrogen atom, a hydroxyl group, an alkoxyl group having 1 to 4 carbon atoms, or an acyloxy group having 2 to 7 carbon atoms;
R$^2$ represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms an acylated N-acylamino aldose residue having, an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid residue having, substituted for the hydrogen atom of the hydroxyl group of the sugar, an alkylacyl group with 2 to 4 carbon atoms or an arylacyl group with 7 to 9 carbon atoms, an acylated aldohexuronic acid ester residue having, substituted for the hydrogen atom of the hydroxyl group of the sugar, an alkylacyl group with 2 to 4 carbon atoms or an arylacyl group with 7 to 9 carbon atoms, an arylalkylated aldose residue having, substituted for the hydrogen atom of the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated N-acylaminoaldose residue having an amino group with an acyl group with 2 to 4 carbon atoms and having, substituted for the hydrogen of the hydroxyl group of the sugar, an arylalkyl group with 7 to 8 carbon atoms an arylalkylated aldohexuronic amide residue having, substituted for the hydrogen atom of the hydroxyl group of the sugar, an arylalkyl group with 7 to 8 carbon atoms, an arylalkylated aldohexuronic acid residue having, substituted for the hydrogen atom of the hydroxyl group of the sugar, an arylalkyl group with 7 to 8 carbon atoms, an arylalkylated aldohexuronic acid ester residue having, substituted for the hydrogen atom of the hydroxyl group of the sugar, an arylalkyl group with 7 to 8 carbon atoms; and $R^3$ represents a hydrogen atom, a linear, branched, cyclic, or cyclic-linear alkyl group having 1 to 5 carbon atoms;

$X^{\ominus}$ represents a pharmaceutically acceptable inorganic or organic acid anion; and The bond represented by $N^{\oplus}$—$R^2$ in the general formula (I) represents a glycoside bond between a nitrogen atom in the 2-position of the ellipticine and a carbon atom in the 1-position of the sugar.

DESCRIPTION OF THE PREFERRED EMBODIMENT

The present inventors have noticed the antineoplastic or antitumor activities of ellipticine in the course of their study to develop various useful derivative having pharmaceutical activities derived from naturally occurring skeletones. It has been intended to improve the very poor water-solubility of the skeleton of the ellipticine. It is known in the art that alkyl groups, hydroxyalkyl groups, aminoalkyl groups and the like are introduced into the nitrogen atom in the 2-position of ellipticine as shown in U.S. Pat. No. 4,310,667. It has been found that, when sugar is introduced into the nitrogen atom in the 2-position of ellipticine, to improve the water-solubility of ellipticine, the resultant ellipticine derivatives having the above-mentioned general formula (I) are useful compounds having the desired water-solubility and remarkably strong antineoplastic or antitumor activity.

The introduction of sugar into the nitrogen atom in the 2-position of ellipticine can be readily carried out in the same manner as in the well-known reaction used in the synthesis of nicotinic amide nucleotide wherein sugar makes a covalent bond with the nitrogen atom of the pyridine ring to form a quaternary salt, as disclosed in, for example, L.J. Haynes et, al., J. Chem, Soc., 303–308 (1950) and L.J. Haynes et. al. J. Chem. Soc., 3727–3732 (1957). Furthermore, it is expected, as disclosed in S. C. Jain et. al., J. Mol. Biol., 135, 813–840 (1979), that the introduction of a substituent having an appropriate size and a hydrophilic property into the nitrogen atom in the 2-position of ellipticine further increases the affinity thereof with the base of nucleic acid.

The ellipticine derivatives having the general formula (I) can be readily produced from ellipticine derivatives having the following general formula (II) according to the present invention.

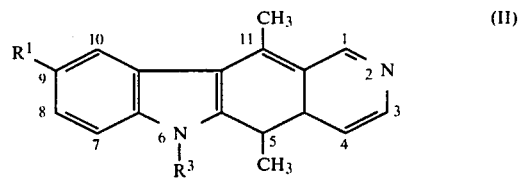

wherein $R^1$ and $R^3$ are the same as defined above. Of the ellipticine derivatives having the general formula (II), ellipticine ($R^1$=H, $R^3$=H), and 9-methoxyellipticine ($R^1$=OCH$_3$, $R^3$=H) are naturally occuring alkaloids as mentioned above. These natural substances can be used as a starting material in the present invention. The ellipticine derivatives (II) can be prepared from pyridocarbazoles as described in, for example, L.K. Dalton et. al., Aust. J. Chem., 20, 2715–2727 (1967). Furthermore, the ellipticine derivatives (II) having an alkyl group with 1 to 5 carbon atoms as $R^3$ of the general formula (II) can be prepared by, for example, treating the above-mentioned ellipticine derivatives having a hydrogen atom as $R^3$ of the general formula (II) with a base such as sodium hydride, potassium hydride, potassium t-butoxide, or triphenylmethyl sodium in an organic solvent such as amido or other type solvents, preferably dimethylformamide to form the alkali metal salts, followed by the addition of the corresponding alkyl halides such as methyl iodide, ethyl iodide, propyl iodide, isopropyl iodide, butyl iodide, sec-butyl iodide, isobutyl iodide, pentyl iodide, cyclopropylmethyl iodide, cyclobutylmethyl iodide, cyclopropylethyl iodide, methyl bromide, ethyl bromide, propyl bromide, isopropyl bromide, butyl bromide, sec-butyl bromide, isobutyl bromide, pentyl bromide, cyclopropylmethyl bromide, cyclobutylmethyl bromide, and cyclopropylethyl bromide.

According to the present invention, the abovementioned ellipticine derivatives (II) are reacted with aldose derivatives having the following general formula (III) upon heating (e.g., 80° C. to 130° C.) in the presence or absence of an acid captured reagent in an organic solvent.

$$R^4—Y \quad \text{(III)}$$

wherein $R^4$ represents an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid ester residue having, substituted for the hydrogen atom of the hydroxyl group of the sugar, an alkylacyl group with 2 to 4 carbon atoms or an arylacyl group with 7 to 9 carbon atoms, an arylalkylated aldose residue having, substituted for the hydrogen atom of the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated N-acylaminoaldose residue having an amino group with an acyl group with 2 to 4 carbon atoms and having, substituted for the hydrogen atom of the hydroxyl group of the sugar, an arylalkyl group with 7 to 8 carbon atoms, an arylalkylated aldohexuronic amide residue having, substituted for the hydrogen atom of the hydroxyl group of the sugar, an arylakyl group with 7 to 8 carbon atoms, an arylalkylated aldohexuronic acid ester residue having, substituted for the hydrogen atom of the hydroxyl group of the sugar, an arylakyl group with 7 to 8 carbon atoms; and Y represents a halogen atom.

As a result of the above-mentioned reaction between the compounds (II) and (III), the ellipticine derivatives having the following general formula (Ia) are obtained according to the present invention.

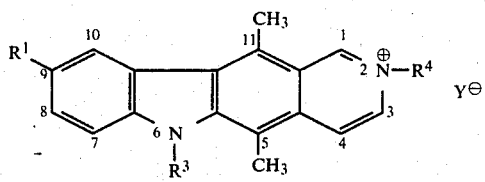

wherein $R^1$, $R^3$, $R^4$ and $Y^\ominus$ are the same as defined above and the bond represented by $N^\oplus$—$R^4$ in the general formula (Ia) represents a glycoside bond between a nitrogen atom in the 2-position of the ellipticine and a carbon atom in the 1-position of the sugar.

The above-mentioned reaction can be advantageously carried out when the starting material (III) is readily available, as in the case of chloro- or bromosugar. As mentioned above, the ellipticine derivatives (Ia) can be obtained by heating the reactants (II) and (III) in an organic solvent such as nitromethane, acetonitrile, propionitrile, benzene, toluene, xylene, dimethylformamide, dimethylsulfoxide, or aniline. Furthermore, this reaction can be effected in the presence of an acid captured reagent with or without heating in an organic solvent. Examples of such acid captured reagents are calcium carbonate, cadmium carbonate, basic zinc carbonate, silver carbonate, and basic copper carbonate. The use of these metal compounds allows the reaction yield to be increased.

The resultant ellipticine derivatives (Ia) can be separated and purified, after the completion of the reaction, by column chromatography, fractional thin-layer chromatography or recrystallization. For example, when cadmium carbonate is used as a base, the resultant ellipticine (Ia) can be purified by column chromatography to such an extent that the content of the cadmium is less than 0.1 ppm as determined by atomic absorption spectroscopy.

The above-mentioned ellipticine derivatives (Ia) can be ion-exchanged with an ion-exchange resin to obtain ellipticine derivatives having the following general formula (Ib):

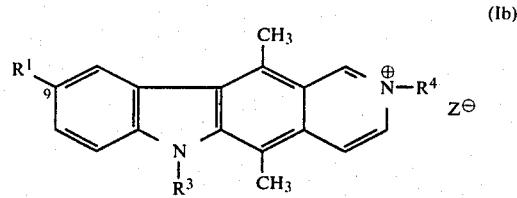

wherein $R^1$, $R^3$, and $R^4$ are the same as defined above and $Z^\ominus$ is a pharmaceutically acceptable inorganic or organic acid anion.

Examples of the pharmaceutically acceptable inorganic or organic acid anions are those derived from, for example, hydrochloric acid, hydrobromic acid, hydroiodic acid, perchloric acid, sulfuric acid, phosphoric acid, nitric acid, carbonic acid, acetic acid, propionic acid, oxalic acid, tartaric acid, lactic acid, malic acid, formic acid, fumaric acid, maleic acid, butyric acid, valeric acid, caproic acid, heptanoic acid, capric acid, citric acid, butyric acid, salicylic acid, methane sulfonic acid, succinic acid, aspartic acid, glutamic acid, benzoic acid, and cinnamic acid.

Examples of the ion-exchange resins usable in the above-mentioned ion-exchange reaction are commercially available anion exchange resins such as Amberlite (available from Organo K.K. Japan), Dowex (available from Dow Chemical Company), and BIO-RAD (available from BIO-RAD Chemical Division).

The above-mentioned ellipticine derivatives (Ib) can be further hydrolyzed to obtain ellipticine derivatives having the following general formula (Ic):

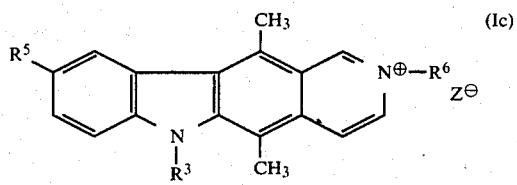

wherein $R^3$ and $Z^\ominus$ are the same as defined above, $R^5$ represents a hydrogen atom, a hydroxyl group, or an alkoxyl group having 1 to 4 carbon atoms, and $R^6$ represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an arylalkylated aldose residue having, substituted for the hydrogen atom of the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated aldohexuronic amide residue having, substituted for the hydrogen atom of the hydroxyl group of the sugar, an arylalkyl group with 7 to 8 carbon atoms, an arylalkylated aldohexuronic acid residue having, substituted for the hydrogen atom of the hydroxyl group of the sugar, an arylalkyl group with 7 to 8 carbon atoms, an arylalkylated N-acylaminoaldose residue having an amino group substituted with an acyl group with 2 to 4 carbon atoms and having, substituted for the hydrogen atom of the hydroxyl group of the sugar, an arylalkyl group with 7 to 8 carbon atoms.

The above-mentioned hydrolysis can be carried out in the presence of a base, especially a weak base. Examples of such weak bases are ammonia, sodium bicarbonate, potassium bicarbonate, basic sodium phosphate, basic potassium phosphate, sodium tetraborate ($Na_2B_4O_7$), potassium tetraborate ($K_2B_4O_7$), lithium carbonate, sodium carbonate, potassium carbonate, calcium carbonate, trialkyl amines, calcium hydroxide, aqueous dilute solutions of sodium hydroxide, and potassium hydroxide. Of these bases, the use of ammonia or an aqueous sodium bicarbonate solution is most preferable under conventional hydrolysis conditions according to sugar chemistry.

On the other hand, the above-mentioned ellipticine derivatives (Ia) can be hydrolyzed to obtain ellipticine derivatives having the following general formula (Id):

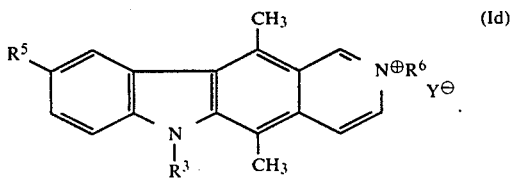

wherein $R^3$, $R^5$, $R^6$ and $Y^\ominus$ are the same as defined above.

These ellipticine derivatives (Id) can be ion-exchanged, in the same manner as mentioned above, to obtain the above-mentioned ellipticine derivatives (Ic). Thus, according to the synthetic methods mentioned above, the ellipticine derivatives (Ia) to (Id) having sugar, acylated sugar, or arylalkylated sugar bonded to the nitrogen atom in the 2-position of the ellipticine skeleton can be produced.

The above-mentioned ellipticine derivatives (Ib) can be further treated with a dealkylating reagent to obtain ellipticine derivatives having the following general formula (Ie):

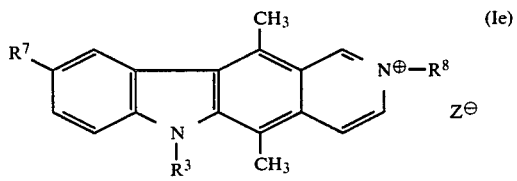

wherein $R^3$ and $Z^\ominus$ are the same as defined above, $R^7$ represents a hydrogen atom, a hydroxyl group, or an acyloxy group having 2 to 7 carbon atoms; and $R^8$ represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylcyl group with 7 to 9 carbon atoms, an acylated aldohexuronic acid residue having, substituted for the hydrogen atom of the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms.

Typical examples of the dealkylating agents usable in the above-mentioned reaction are trialkyl silyl iodide, most preferably trimethyl silyl iodide. The dealkylating reaction can be carried out in any inert solvent, preferably in a chlorine type or aromatic type hydrocarbon solvent. After the completion of the reaction, the resultant ellipticine derivatives (Ie) can be purified by recrystallization, column chromatography, or fractional thin-layer chromatography. Furthermore, the above-mentioned ellipticine derivatives (Ia) can be subjected to dealkylation reaction in the same manner to obtain ellipticine derivatives having the following general formula (Ig):

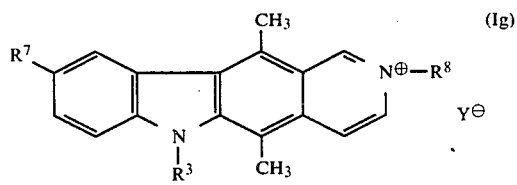

wherein $R^3$, $R^7$, $R^8$ and $Y^\ominus$ are the same as defined above.

The resultant ellipticine derivatives (Ig) can be ion-exchanged as mentioned above to obtain the above-mentioned ellipticine derivatives (Ie).

The above-mentioned ellipticine derivatives (Ie) can be further hydrolyzed to obtain ellipticine derivatives having the general formula (If):

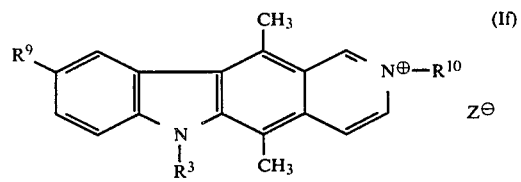

wherein $R^3$ and $Z^\ominus$ are the same as defined above, $R^9$ represents a hydrogen atom or a hydroxyl group, and $R^{10}$ represents an aldose residue, a deoxyaldose residue, an N-acylaminoaldose residue having a substituted acyl group with 2 to 4 carbon atoms bonded to the N atom, an aldohexuronic amide residue, or an aldohexuronic acid residue. The bases usable in the hydrolysis are the same as mentioned above. The above-mentioned ellipticine derivatives (Ig) can be hydrolyzed in the same manner as mentioned above to obtain ellipticine derivatives having the general formula (Ih):

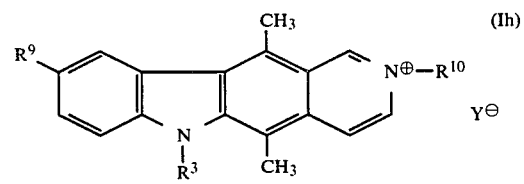

wherein $R^3$, $R^9$, $R^{10}$, and $Y^\ominus$ are the same as defined above.

The ellipticine derivatives (Ih) can be ion-exchanged as mentioned above, to form the above-mentioned ellipticine derivatives (If).

Furthermore, the above-mentioned ellipticine derivatives (Ic) can be further dealkylated as mentioned above to obtain ellipticine derivatives having the general formula (If).

The ellipticine derivatives (Id) can be further dealkylated to form the ellipticine derivative having the above-mentioned general formula (Ih).

As mentioned above, the above-mentioned various derivatives (Ib) to (Ih) can be obtained by the hydrolysis, dealkylation, and/or ion-exchanging from the ellipticine derivatives (Ia) obtained from the reactions of the ellipticine derivatives (II) with the aldose derivatives (III).

The glycoside bond between the nitrogen atom in the 2-position of the ellipticine derivatives and the carbon atom in the 1-position of the sugar can be confirmed by nuclear magnetic resonance (NMR) spectrum, mass spectrum, and elementary analysis. Thus, when the signal of the hydrogen atom in the 1-position of the sugar (i.e., anomeric hydrogen) is irradiated, the signal intensity of the hydrogen atom in the 1- and 3-position of the ellipticine derivative is increased (NOE). Therefore, the bonding of the carbon atom in the 1-position of the sugar to the nitrogen atom in the 2-position of the ellipticine derivatives can be confirmed.

Examples of the substituent $R^2$ in the abovementioned general formula (I) are the residues of aldotetroses such as D-erythrose, D-threose, L-erythrose, L-threose, di-O-acetyl-D-erythrose, di-O-acetyl-D-threose, di-O-acetyl-L-erythrose, di-O-acetyl-L-threose, di-O-benzoyl-D-erythrose, di-O-benzoyl-D-threose, di-O-benzoyl-L-erythrose, di-O-benzoyl-L-threose, di-O-benzyl-D-erythrose, di-O-benzyl-D-threose, di-O-benzyl-L-erythrose, and di-O-benzyl-L-threose; the residues of aldopentoses such as D-ribose, D-xylose, L-ribose, L-xylose, D-arabinose, D-lyxose, L-arabinose, L-lyxose, tri-O-acetyl-D-ribose, tri-O-acetyl-D-xylose, tri-O-acetyl-L-ribose, tri-O-acetyl-L-xylose, tri-O-acetyl-D-arabinose, tri-O-acetyl-D-lyxose, tri-O-acetyl-L-arabinose, tri-O-acetyl-L-lyxose, tri-O-benzoyl-D-ribose, tri-O-benzoyl-D-xylose, tri-O-benzoyl-L-ribose, tri-O-benzoyl-L-xylose, tri-O-benzoyl-D-arabinose, tri-O-benzoyl-D-lyxose, tri-O-benzoyl-L-arabinose, tri-O-benzoyl-L-lyxose, tri-O-benzyl-D-ribose, tri-O-benzyl-D-xylose, tri-O-benzyl-L-ribose, tri-O-benzyl-L-xylose, tri-O-benzyl-D-arabinose, tri-O-benzyl-D-lyxose, tri-O-benzyl-L-arabinose, and tri-O-benzyl-L-lyxose; the residues of aldohexoses such as D-glucose, D-mannose, L-glucose, L-mannose, D-allose, D-altrose, L-allose, L-altrose, D-gulose, D-idose, L-gulose, L-idose, D-galactose, D-talose, L-galactose, L-talose, tetra-O-acetyl-D-glucose, tetra-O-acetyl-D-mannose, tetra-O-acetyl-L-glucose, tetra-O-acetyl-L-mannose, tetra-O-acetyl-D-allose, tetra-O-acetyl-D-altrose, tetra-O-acetyl-L-allose, tetra-O-acetyl-L-altrose, tetra-O-acetyl-D-gulose, tetra-O-acetyl-D-idose, tetra-O-acetyl-L-gulose, tetra-O-acetyl-L-idose, tetra-O-acetyl-D-galactose, tetra-O-acetyl-D-talose, tetra-O-acetyl-L-galactose, tetra-O-acetyl-L-talose, tetra-O-benzoyl-D-glucose, tetra-O-benzoyl-D-mannose, tetra-O-benzoyl-L-glucose, tetra-O-benzoyl-L-mannose, tetra-O-benzoyl-D-allose, tetra-O-benzoyl-D-altrose, tetra-O-benzoyl-L-allose, tetra-O-benzoyl-L-altrose, tetra-O-benzoyl-D-gulose, tetra-O-benzoyl-D-idose, tetra-O-benzoyl-L-gulose, tetra-O-benzoyl-L-idose, tetra-O-benzoyl-D-galactose, tetra-O-benzoyl-D-talose, tetra-O-benzoyl-L-galactose, tetra-O-benzoyl-L-talose, tetra-O-benzyl-D-glucose, tetra-O-benzyl-D-mannose, tetra-O-benzyl-L-glucose, tetra-O-benzyl-L-mannose, tetra-O-benzyl-D-allose, tetra-O-benzyl-D-altrose, tetra-O-benzyl-L-allose, tetra-O-benzyl-L-altrose, tetra-O-benzyl-D-gulose, tetra-O-benzyl-D-idose, tetra-O-benzyl-L-gulose, tetra-O-benzyl-L-idose, tetra-O-benzyl-D-galactose, tetra-O-benzyl-D-talose, tetra-O-benzyl-L-galactose, and tetra-O-benzyl-L-talose, the residues of 2- or 6-deoxyaldohexoses such as D-quinovose (i.e., 6-deoxy-D-glucose) L-rhamnose (i.e., 6-deoxy-L-mannose), L-fucose (i.e., 6-deoxy-L-galactose), D-fucose (i.e., 6-deoxy-D-galactose), 6-deoxy-D-allose, 6-deoxy-L-altrose, 6-deoxy-D-gulose, 6-deoxy-L-talose, tri-O-acetyl-D-quinovose, tri-O-acetyl-L-rhamnose, tri-O-acetyl-L-fucose, tri-O-acetyl-D-fucose, 6-deoxy-tri-O-acetyl-D-allose, 6-deoxy-tri-O-acetyl-L-altrose, 6-deoxy-tri-O-acetyl-D-gulose, 6-deoxy-tri-O-acetyl-L-talose, tri-O-benzoyl-D-quinovose, tri-O-benzoyl-L-rhamnose, tri-O-benzoyl-L-fucose, trio-O-benzoyl-D-fucose, 6-deoxy-tri-O-benzoyl-D-allose, 6-deoxy-tri-O-benzoyl-D-altrose, 6-deoxy-tri-O-benzoyl-D-gulose, 6-deoxy-tri-O-benzoyl-L-talose, tri-O-benzyl-D-quinavose, tri-O-benzyl-L-rhamnose, tri-O-benzyl-L-fucose, tri-O-benzyl-D-fucose, 6-deoxy-tri-O-benzyl-D-allose, 6-deoxy-tri-O-benzyl-D-altrose, 6-deoxy-tri-O-benzyl-D-gulose, 6-deoxy-tri-O-benzyl-L-talose, 2-deoxy-D-glucose, 2-deoxy-D-gulose, 2-deoxy-D-galactose, 2-deoxy-tri-O-acetyl-D-glucose, 2-deoxy-tri-O-acetyl-D-gulose, 2-deoxy-tri-O-acetyl-D-galactose, 2-deoxy-tri-O-benzoyl-D-glucose, 2-deoxy-tri-O-benzoyl-D-gulose, 2-deoxy-tri-O-benzoyl-D-galactose, 2-deoxy-tri-O-benzyl-D-glucose, 2-deoxy-tri-O-benzyl-D-gulose, and 2-deoxy-tri-O-benzyl-D-galactose; the residues of 2- or 5-deoxyaldopentoses such as 2-deoxy-D-ribose, 5-deoxy-L-arabinose, 5-deoxy-D-xylose, 5-deoxy-D-lyxose, 5-deoxy-D-ribose, 2-deoxy-di-O-acetyl-D-ribose, 5-deoxy-di-O-acetyl-L-arabinose, 5-deoxy-di-O-acetyl-D-xylose, 5-deoxy-di-O-acetyl-D-lyxose, 5-deoxy-di-O-acetyl-D-ribose, 2-deoxy-di-O-benzoyl-D-ribose, 2-deoxy-di-O-benzoyl-D-arabinose, 5-deoxy-di-O-benzoyl-D-xylose, 5-deoxy-di-O-benzoyl-D-lyxose, 5-deoxy-di-O-benzoyl-D-ribose, 2-deoxy-di-O-benzyl-D-ribose, 5-deoxy-di-O-benzyl-L-arabinose, 5-deoxy-di-O-benzyl-D-xylose, 5-deoxy-di-O-benzyl-D-lyxose, 5-deoxy-di-O-benzyl-D-ribose; the residues of N-acylaminoaldoses such as N-acetyl-D-galactosamine (2-acetamido-2-deoxy-D-galactose), N-acetyl-D-glucosamine(2-acetamido-2-deoxy-D-glucose), N-acetyl-D-gulosamine(2-acetamido-2-deoxy-D-gulose), N-acetyl-D-talosamine(2-acetamido-2-deoxy-D-talose), N-acetyl-D-mannosamine(2-acetamido-2-deoxy-D-mannose), N-acetyl-D-kanosamine(6-acetamido-6-deoxy-D-glucose), N-acetyl-D-fucosamine(2-acetamido-2,6-dideoxy-L-galactose), N-acetyl-L-fucosamine, N-acetyl-mycosamine(3-acetamido-3,6-dideoxy-D-mannose), N-acetyl-pneumosamine(2-acetamido-2,6-dideoxy-L-talose), N-acetyl-tri-O-acetyl-D-galactosamine, N-acetyl-tri-O-acetyl-D-glucosamine, N-acetyl-tri-O-acetyl-D-gulosamine, N-acetyl-tri-O-acetyl-D-talosamine, N-acetyl-tri-O-acetyl-D-mannosamine, N-acetyl-tri-O-acetyl-kanosamine, N-acetyl-di-O-acetyl-D-fucosamine, N-acetyl-di-O-acetyl-L-fucosamine, N-acetyl-di-O-acetyl-mycosamine, N-acetyl-di-O-acetyl-pneumosamine, N-acetyl-tri-O-benzoyl-D-galactosamine, N-acetyl-tri-O-benzoyl-D-glucosamine, N-acetyl-tri-O-benzoyl-D-gulosamine, N-acetyltri-O-benzoyl-D-talosamine, N-acetyl-tri-O-benzoyl-D-mannosamine, N-acetyl-tri-O-benzoyl-kanosamine, N-acetyl-di-O-benzoyl-D-fucosamine, N-acetyl-di-O-benzoyl-L-fucosamine, N-acetyl-di-O-benzoyl-mycosamine, N-acetyl-di-O-benzoyl-pneumosamine, N-acetyl-tri-O-benzyl-D-galactosamine, N-acetyl-tri-O-benzyl-D-glucosamine, N-acetyl-tri-O-benzyl-D-gulosamine, N-acetyl-tri-O-benzyl-D-talosamine, N-acetyl-tri-O-benzyl-D-mannosamine, N-acetyl-tri-O-benzyl-kanosamine, N-acetyl-di-O-benzyl-D-fucosamine, N-acetyl-di-O-benzyl-L-fucosamine, N-acetyl-di-O-benzyl-mycosamine, N-acetyl-di-O-benzyl-pneumosamine; the residues of aldohexuronic acid derivatives such as L-iduronic acid, D-galacturonic acid, D-glucuronic acid, L-glucuronic acid, D-mannuronic acid, methyl tri-O-acetyl-L-iduronate, methyl tri-O-acetyl-D-galacturonate, methyl tri-O-D-glucuronate, methyl tri-O-acetyl-L-glucuronate, methyl tri-O-acetyl-D-mannuronate, methyl tri-O-benzoyl-L-iduronate, methyl tri-O-benzoyl-D-galacturonate, methyl tri-O-benzoyl-D-glucuronate, methyl tri-O-benzoyl-L-glucuronate, methyl tri-O-benzyl-L-iduronate, methyl tri-O-benzyl-D-galacturonate, methyl tri-O-benzyl-D-glucuronate, and methyl tri-O-benzyl-L-glucuronate; and the residues of aldohexuronic amides such as L-iduronic amide, D-galacturonic amide, D-glucuronic amide, L-glucuronic amide, D-mannuronic amide, tri-O-acetyl-L-iduronic amide, tri-O-acetyl-D-galacturonic amide, tri-O-acetyl-D-glucuronic amide, tri-O-acetyl-L-glucuronic amide tri-O-acetyl-D-mannuronic amide, tri-O-benzoyl-L-iduronic amide, tri-O-benzoyl-D-galacturonic amide, tri-O-benzoyl-D-glucuronic amide, tri-O-benzoyl-L-glucuronic amide, tri-O-benzoyl-D-mannuronic amide, tri-O-benzyl-L-iduronic amide, tri-O-benzyl-D-galacturonic amide, tri-O-benzyl-D-glucuronic amide, tri-O-benzyl-L-glucuronic amide, and tri-O-benzyl-D-mannuronic amide.

The ellipticine derivatives according to the present invention are generally disclosed and decomposed within a wide temperature range during the measurement of melting points and, therefore, do not exhibit clear melting points.

The ellipticine derivatives having the general formula (I) (and the general formulae (Ia) to (Ih), according to the present invention have remarkable antineoplastic or antitumor effects against mouse lymphoid leukemia L 1210 as shown in the Examples hereinbelow. It is considered that the present ellipticine derivatives are effective antineoplastic or antitumor agents in view of the fact that the antineoplastic or antitumor activity of the present ellipticine derivatives is superior to that of Celiptium used as a control, which is clinically administered to patients with mammary cancer.

When the present ellipticine derivatives are used as an antineoplastic or antitumor agent, they can be used in any form, for example, in the form of injection such as endovenous, intramuscular, or hypodermic injection, in the form of oral administration drugs such as tablets, granulars, powder, or troches, or in the form of endermic drugs such as vaginal or rectal suppository, or ointments.

In the practice of the formulation, any conventional and pharmaceutically acceptable ingredients including diluents, carriers, excipients, binders, and vehicles can be used. Pharmaceutically acceptable vehicles such as atoxic liquid oil can be used as a suspending agent.

REMARKS

The compound Nos. 1 to 14 in Table 1 have the following general formula:

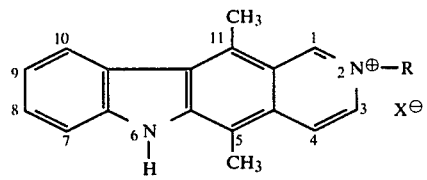

The compound Nos. 15 to 28 in Table 1 have the following general formula:

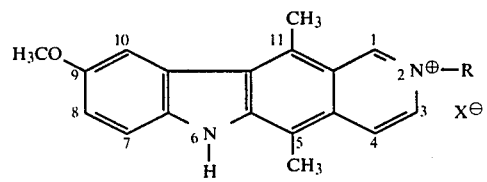

The compound Nos. 29 to 52 in Table 1 have the following general formula:

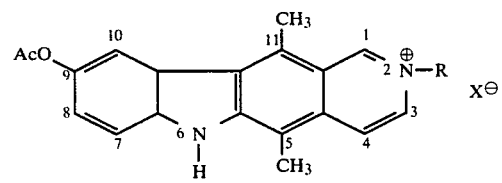

The compound Nos. 53 to 112 in Table 1 have the following general formula:

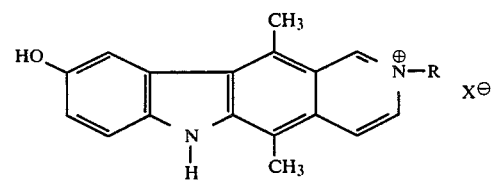

The compound Nos. 113 to 172 in Table 2 have the following general formula:

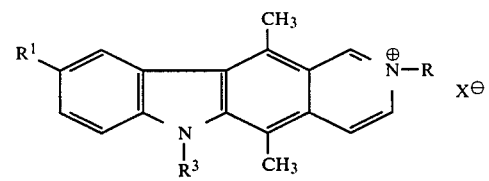

EXAMPLES

The present invention now will be further illustrated by, but is by no means limited to, the following examples.

In the examples, the following abbreviations and commercial products are used.
Ac: Acetyl group
Bz: Benzoyl group
Bn: Benzyl group BIO-RAD Ag1-X8: Ion exchange resin available from BIO-RAD Chemical Division Sephadex LH20: Gel infiltration resin available from Pharmacia Fine Chemicals A.G.

Kieselgel 60: Silicagel available from Merck & Co., Inc.

Furthermore, the analytical data in the Examples were obtained as follows:

UV absorption spectrum: Shimadzu UV-250 or Beckman DU-8 Spectrophotometer

IR absorption spectrum: Hitachi 260-10 or Nicolet 5DX(FT-IR)

Specific rotatory power [α]$_D$: Perkin-Elmer 241 Polarimeter or JASCO DIP-181 Digital Polarimeter Proton NMR: Nicolet NT-360, Nicolet NT-300, or Nippon Denshi GX-270

Mass spectrum: SIMS method (partial chemical ionization (C.I.) method)

In Examples 96, 97, 109, 110, and 111, molecular ellipticity in water was used instead of [α]$_D$.

[α]$_D$ was measured by the following conditions:

| | |
|---|---|
| Example 1 to 12 | at 29° C. |
| Examples 13, 14 | at 25° C. |
| Examples 15 to 28 | at 31° C. |
| Examples 29 to 52 | at 26° C. in methanol |
| Example 53 | at 29° C. |
| Example 54 | at 26° C. |
| Examples 55 to 61 | at 29° C. |
| Examples 62 to 95 | } in 1% CF$_3$COOH—H$_2$O at 25° C. |
| Examples 98 to 106 | | another condition was shown in Tables 1 and 2. In Tables 1 and 2, the following abbreviations are used.

MeOH: methanol
EtOH: ethanol
DMSO: dimethylsulfoxide.

EXAMPLE 1

Preparation of 2-(2,3,4,6-tetra-O-acetyl-β-D-galactopyranosyl)ellipticinium bromide

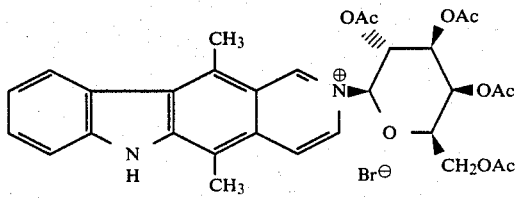

A 300 mg amount of ellipticine, 860 mg of 2,3,4,6-tetra-O-acetyl-α-D-galactopyranosyl bromide, and 1.190 g of cadmium carbonate were suspended in 37 ml of nitromethane and the solution was heated under reflux for 20 minutes. After cooling the insoluble matter was filtered and washed with a small amount of nitromethane. The nitromethane layer was concentrated in vacuo to obtain 1.4 g of the crystalline residue.

The residue obtained above was subjected to silicagel column chromatography using, as an elute solvent, a mixture of chloroform and methanol (95:5). Thus, 810 mg of the crystalline compound was obtained. This compound contained a small amount of impurities and, therefore, the compound was purified by column chromatography (Sephadex LH20, solvent: methanol). As a result, 567 mg of the desired compound was obtained.

The analytical data of the resultant compound are shown in Table 1.

EXAMPLE 2

Preparation of 2-β-D-galactopyranosylellipticinium bromide

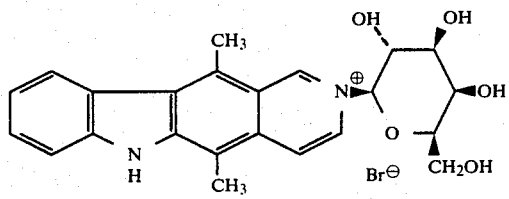

A 250 mg amount of the ellipticine derivative obtained in Example 1 was dissolved in 50 ml of methanol saturated with gaseous ammonia and was allowed to stand overnight in a refrigerator. The insoluble matter was filtered and then, the resultant solution was concentrated to obtain 105 mg of the desired compound.

The results are shown in Table 1.

EXAMPLE 3 to 5

The following ellipticine derivatives were prepared in the same manner as in Examples 1 and 2.

Example 3: 2-(2,3,5-tri-O-benzoyl-β-D-ribofuranosyl)ellipticinium bromide.

Example 4: 2-β-D-ribofuranosylellipticinium bromide.

Example 5: 2-(2,3,4,6-tetra-O-acetyl-β-D-glucopyranosyl)ellipticinium bromide.

The results are shown in Table 1.

EXAMPLE 6

Preparation of 2-β-D-glucopyranosylellipticinium acetate

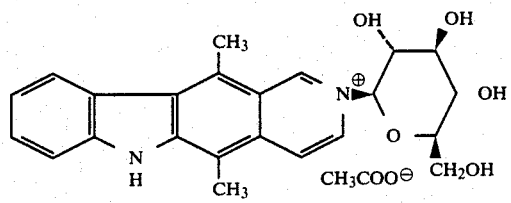

A 98 mg amount of the ellipticinium derivative obtained in Example 5 was dissolved in a dimethylformamide-water solvent and was then passed through an ion exchange resin column (BIO-RAD, AG1-X8, acetate type). The column was eluted with water. Thus, 111 mg of 2-(2,3,4,6-tetra-O-acetyl-β-D-glucopyranosyl)ellipticinium acetate was obtained. To the resultant compound, 15 ml of methanol saturated with gaseous ammonia was added and the mixture was allowed to stand at a temperature of 0° C. to 5° C. for 15 hours. After concentrating, a small amount of methanol was added to the concentrated mixture and, then, ethyl acetate was added to precipitate 52 mg of the desired compound in the form of powder.

EXAMPLES 7 TO 12

The following ellipticine derivatives were prepared in the same manner as in Examples 1 and 2.

Example 7: 2-(2,3,4-tri-O-acetyl-β-D-fucopyranosyl)ellipticinium bromide.

Example 8: 2-β-D-fucopyranosylellipticinium bromide.

Example 9: 2-(2,3,4-tri-O-acetyl-β-L-fucopyranosyl)ellipticinium bromide.

Example 10: 2-β-L-fucopyranosylellipticinium bromide.

Example 11: 2-(2,3,4-tri-O-acetyl-α-L-rhamnopyranosyl)ellipticinium bromide.

Example 12: 2-α-L-rhamnopyranosylellipticinium bromide.

The results are shown in Table 1.

EXAMPLE 13

Preparation of 2-(2,3,5-tri-O-benzoyl-β-D-xylofuranosyl)ellipticinium chloride

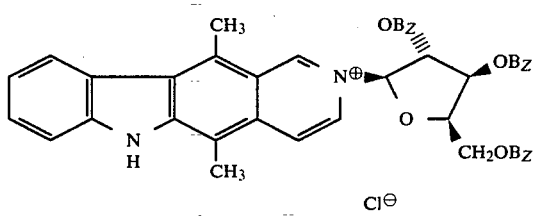

A 70 mg amount of ellipticine, 70 mg of cadmium carbonate, and 230 mg of 2,3,5-tri-O-benzoyl-α-D-xylofuranosyl chloride were suspended in 7 ml of nitromethane and the suspension was heated under reflux for 10 minutes. The insoluble matter was filtered and the resultant solution was concentrated. The residue thus obtained was subjected to silicagel column chromatography (Kieselgel 60, 50 ml) and the column was eluted by a solvent mixture of methylene chloride and methanol (90:10). The resultant product was then purified by gel filtration chromatography (Sephadex LH-20, 2.0 cmφ×18 cm). Thus, 70.2 mg of the desired product was eluted with methanol.

The results are shown in Table 1.

When 2,3,5-tri-O-benzoyl-α-L-xylofuranosyl chloride was used, 2-(2,3,5-tri-O-benzoyl-β-L-xylofuranosyl)ellipticinium chloride was obtained.

EXAMPLE 14

Preparation of 2-β-D-xylofuranosylellipticinium chloride

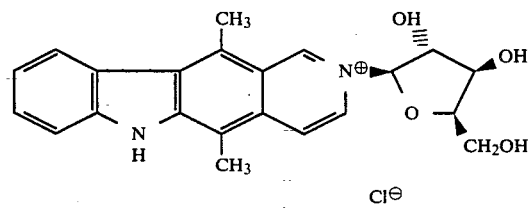

A 55 mg amount of 2-(2,3,5-tri-O-benzoyl-β-D-xylofuranosyl)ellipticinium chloride was dissolved in 9 ml of methanol saturated with gaseous ammonia. The solution was allowed to stand for 15 hours at room temperature. After concentrating, the product was precipitated from a mixture of methanol and ethyl acetate and separated. Thus, 20.2 mg of the desired compound was obtained.

The results are shown in Table 1.

Similarly, when 2-(2,3,5-tri-O-benzoyl-β-L-xylofuranosyl)ellipticinium chloride was used, 2-β-L-xylofuranosylellipticinium chloride was obtained.

EXAMPLE 15

Preparation of 2-(2,3,4,6-tetra-O-acetyl-β-D-galactopyranosyl)-9-methoxyellipticinium bromide

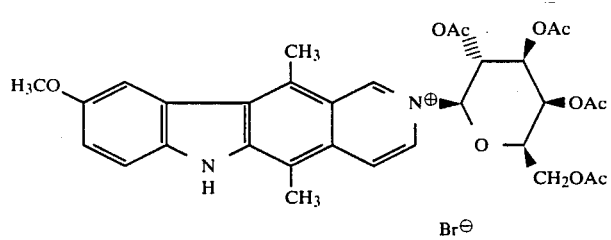

A 100 mg amount of 9-methoxyellipticine, 377 mg (3 equivalent) of α-bromoaceto-D-galactose, and 130 mg of cadmium carbonate were suspended in 15 ml of nitromethane and the mixture was heated under reflux for 15 minutes.

The insoluble matter was filtered and the resultant solution was concentrated to obtain the crystalline residue. The residue was dissolved in methanol and then, was purified with Sephadex LH-20 column (diameter: 4.6 cm, height: 30 cm, methanol as an eluent). Thus, 219 mg of the desired compound was obtained.

The results are shown in Table 1.

EXAMPLE 16

Preparation of 2-β-D-galactopyranosyl-9-methoxyellipticinium bromide

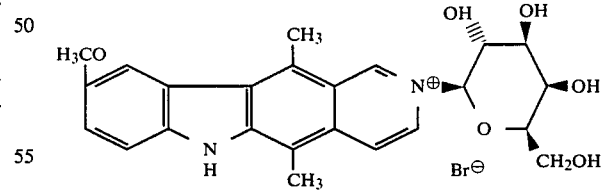

A 19 ml amount of methanol saturated with gaseous ammonia was added to 187 mg of the ellipticinium tetraacetate derivative obtained in Example 15 and the mixture was allowed to stand at a temperature of 0° C. for 15 hours. The insoluble matter was filtered and the resultant solution was concentrated to obtain the crystalline residue. The residue thus obtained was recrystallized from a mixture of methanol and ethyl acetate. Thus, 30 mg of the desired compound in the form of yellow crystal was obtained.

The results are shown in Table 1.

EXAMPLES 17 to 26

The following ellipticine derivatives were prepared in the same manner as in Examples 15 and 16.

Example 17: 2-(2,3,5-tri-O-benzoyl-β-D-ribofuranosyl)-9-methoxyellipticinium bromide.
Example 18: 2-β-D-ribofuranosyl-9-methoxyellipticinium bromide.
Example 19: 2-(2,3,4,6-tetra-O-acetyl-β-D-glucopyranosyl)-9-methoxyellipticinium bromide.
Example 20: 2-β-D-glucopyranosyl-9-methoxyellipticinium bromide.
Example 21: 2-(2,3,4-tri-O-acetyl-β-D-fucopyranosyl)-9-methoxyellipticinium bromide.
Example 22: 2-β-D-fucopyranosyl-9-methoxyellipticinium bromide.
Example 23: 2-(2,3,4-tri-O-acetyl-β-L-fucopyranosyl)-9-methoxyellipticinium bromide.
Example 24: 2-β-L-fucopyranosyl-9-methoxyellipticinium bromide.
Example 25: 2-(2,3,4-tri-O-acetyl-α-L-rhamnopyranosyl)-9-methoxyellipticinium bromide.
EXample 26: 2-α-L-rhamnopyranosyl-9-methoxyellipticinium bromide.

The results are shown in Table 1.

EXAMPLE 27

Preparation of 2-(2,3,5-tri-O-benzoyl-β-D-xylofuranosyl)-9-methoxyellipticinium chloride

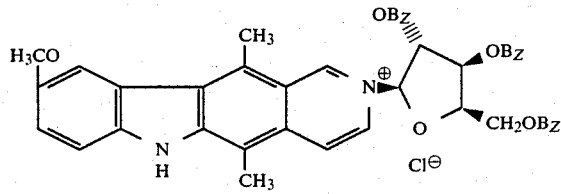

A 70 mg amount of 9-methoxyellipticine, 70 mg of cadmium carbonate, and 230 mg of 2,3,5-tri-O-benzoyl-α-D-xylofuranosyl chloride were suspended in 7 ml of nitromethane and the suspension was heated under reflux for 10 minutes. The insoluble matter was filtered and the resultant solution was concentrated. The residue thus obtained was subjected to silicagel column chromatography (Kieselgel 60, 50 ml) and the column was eluted by a solvent mixture of methylene chloride and methanol (90:10). The resultant product was then purified by gel filtration chromatography (Sephadex LH-20, 2.0 cmφ×20 cm, methanol). Thus, 65 mg of the desired product was obtained.

The results are shown in Table 1.

When 2,3,5-tri-O-benzoyl-α-L-xylofuranosyl chloride was used, 2-(2,3,5-tri-O-benzoyl-β-L-xylofuranosyl)-9-methoxyellipticinium chloride was obtained.

EXAMPLE 28

Preparation of 2-β-D-xylofuranosyl-9-methoxyellipticinium chloride

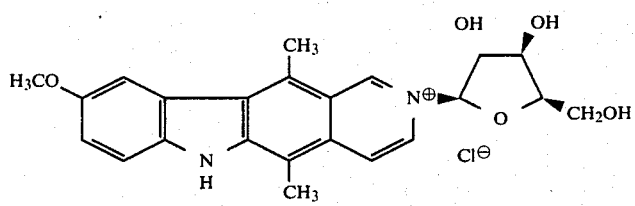

A 51 mg amount of 2-(2,3,5-tri-O-benzoyl-β-D-xylofuranosyl)-9-methoxyellipticinium chloride was dissolved in 8 ml of methanol saturated with gaseous ammonia. The solution was allowed to stand for 15 hours at room temperature. After concentrating, the residue was dissolved in methanol and the product was precipitated from methanol solution with ethyl acetate. Thus, 24 mg of the desired compound was obtained.

The results are shown in Table 1.

Similarly, when 2-(2,3,5-tri-O-benzoyl-β-L-xylofuranosyl)-9-methoxyellipticinium chloride was used, 2-β-L-xylofuranosyl-9-methoxyellipticinium chloride was obtained.

EXAMPLE 29

Preparation of 9-acetoxy-2-(2,3-di-O-benzoyl-β-D-erythrofuranosyl)ellipticinium chloride

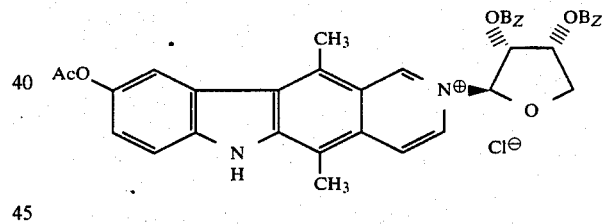

A 172 mg amount of 9-acetoxyellipticine, 170 mg of cadmium carbonate, and 309 mg of 2,3-di-O-benzoyl-D-erythrofuranosyl chloride were added to 17 ml of nitromethane methane and the mixture was heated under reflux for 10 minutes. The insoluble matter was filtered and washed with nitromethane. The nitromethane solution was concentrated to obtain the oily residue.

The oily residue obtained above was subjected to column chromatography using 200 ml of silicagel (Kieselgel 60) and was eluted with a mixture of chloroform and methanol (91:9-87:13) to obtain the yellowish brown compound. The yellowish brown compound was dissolved in 30 ml of methanol. The resultant solution was subjected to column chromatography using Sephadex LH-20 (42 cm×2.5 cmφ) and was eluted with methanol.

The resultant yellowish brown layer was concentrated to obtain 128 mg (35% yield) of the desired compound. The results are shown in Table 1.

When 2,3-di-O-benzoyl-L-erythrofuranosyl chloride was used instead of 2,3-di-O-benzoyl-D-erythrofuranosyl chloride, 9-acetoxy-2-(2,3-di-O-benzoyl-β-L-erythrofuranosyl)ellipticinium chloride was obtained.

EXAMPLE 30

Preparation of
9-acetoxy-2-(2,3-di-O-benzoyl-5-deoxy-β-D-ribofuranosyl)ellipticinium chloride

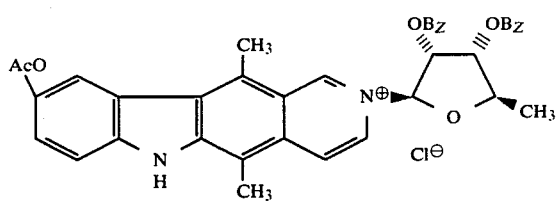

A 300 mg amount of 9-acetoxyellipticine, 708 mg of 2,3-di-O-benzoyl-5-deoxy-D-ribofuranosyl chloride, and 339 mg of cadmium carbonate were suspended in 30 ml of nitromethane and the mixture was heated under reflux for 15 minutes. The insoluble matter was separated by filtration and the solvent was distilled off in vacuo. Thus, 820 mg of the residue was obtained. The residue was dissolved in a 3% methanol-chloroform solvent. The solution was subjected to column chromatography using 600 ml of silicagel and was eluted with a solvent mixture of methanol and chloroform (8:92). Thus, 289 mg of the product was obtained.

A 192 mg amount of the product was then purified by dissolving the product in methanol, followed by subjected to column chromatography using Sephadex LH-20 (5 cmφ×28 cm). 151 mg of the desired compound in the form of yellowish brown powder was obtained by elution with methanol.

The results are shown in Table 1.

EXAMPLES 31 AND 32

The following ellipticine derivatives were prepared in the same manner as in Example 30.

Example 31: 9-Acetoxy-2-(2,3-di-O-benzoyl-5-deoxy-α-L-arabinofuranosyl)ellipticinium chloride Example 32: 9-Acetoxy-2-(3,5-di-O-p-toluoyl-2-deoxy-β-D-ribofuranosyl)ellipticinium chloride The results are shown in Table 1.

EXAMPLE 33

Preparation of
9-acetoxy-2-(2,3-di-O-benzyl-5-deoxy-β-L-arabinofuranosyl)ellipticinium chloride

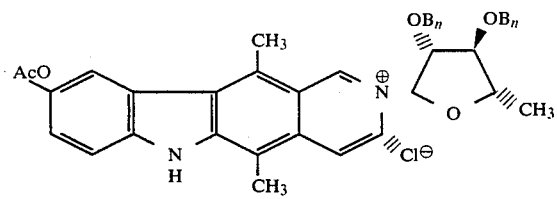

A 242 mg amount of 9-acetoxyellipticine, 394 mg of 2,3-di-O-benzyl-5-deoxy-α-L-arabinofuranosyl chloride, and 242 mg of cadmium carbonate were suspended in 25 ml of nitromethane and the mixture was heated under reflux for 10 minutes. After removing the precipitate, the resultant solution was concentrated. The residue thus obtained was subjected to column chromatography using silicagel (Kieselgel 60, 300 ml) and was eluted with a solvent mixture of methylene chloride and methanol (93:7–91:9). The eluted fraction was then subjected to gel filtration column chromatography using Sephadex LH-20 (4.5 cmφ×22 cm) and was eluted with methanol.

As a result, 310 mg (61% yield) of the desired compound was obtained in the form of orange powder.

The results are shown in Table 1.

EXAMPLE 34

Preparation of
9-acetoxy-2-(2,3,5-tri-O-benzoyl-D-lyxofuranosyl)ellipticinium chloride

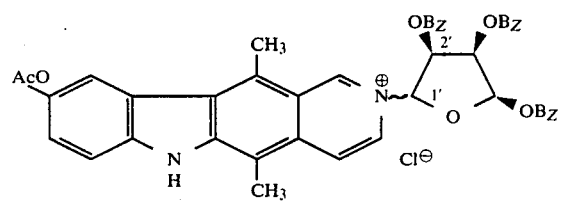

A 324 mg amount of 9-acetoxyellipticine, 320 mg of cadmium carbonate and 870 mg of 2,3,5-tri-O-benzoyl-D-lyxofuranosyl chloride were suspended in 32 ml of nitromethane and the mixture was heated under reflux for 7 minutes. After the precipitate was removed by filtration, the resultant residue was subjected to column chromatography using silicagel (Kieselgel 60, 400 ml) and was eluted with 3.5 liters of a solvent mixture of methylene chloride and methanol (94:6–90:10). The eluted fraction was concentrated and the resultant concentrate was then subjected to gel filtration column chromatography using Sephadex LH 20 (4.5 cmφ×44 cm) and was eluted with methanol.

As a result, 677 mg of the desired compound was obtained.

The product thus obtained had two stereoisomers (i.e., 1',2'-trans-isomer and 1',2'-cis-isomer) to the 1-position of the sugar. The ratio of 1',2'-trans/1', 2'-cis was 6/1 when determined by NMR spectrum of the hydrogen atom in the 1-position of the sugar.

When 2,3,5-tri-O-benzoyl-L-lyxofuranosyl chloride was used instead of the D-lyxofuranosyl chloride, 9-acetoxy-2-(2,3,5-tri-O-benzoyl-L-lyxofuranosyl)ellipticinium chloride was obtained.

EXAMPLE 35

Preparation of
9-acetoxy-2-(2,3,5-tri-O-benzoyl-β-D-xylofuranosyl)ellipticinium chloride

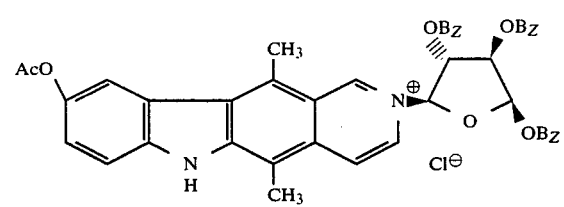

A 215 mg amount of 9-acetoxyellipticine, 713 mg of 2,3,5-tri-O-benzoyl-α-D-xylofuranosyl chloride, and 243 mg of cadmium carbonate were suspended in 22 ml of nitromethane. The suspension was treated in the same manner as in Example 34 by using silicagel column chromatography (600 ml, 3% methanol-chloroform) and gel filtration column chromatography (Sephadex LH-20, 4.2 cmφ×37 cm, methanol).

As a result, 304 mg of the desired compound was obtained. The results are shown in Table 1.

When 2,3,5-tri-O-benzoyl-α-L-xylofuranosyl chloride was used instead of the D-xylofuranosyl chloride, 9-acetoxy-2-(2,3,5-tri-O-benzoyl-β-L-xylofuranosyl)ellipticinium chloride was obtained.

EXAMPLE 36 TO 39

The following ellipticine derivatives were prepared in the same manner as in Example 35.

Example 36:
9-Acetoxy-2-(2,3,5-tri-O-benzoyl-α-D-arabinofuranosyl)ellipticinium bromide.
9-Acetoxy-2-(2,3,5-tri-O-benzoyl-α-L-arabinofuranosyl)ellipticinium bromide.

Example 37: 9-Acetoxy-2-(2,3,5-tri-O-benzoyl-β-L-ribofuranosyl)ellipticinium bromide.

Example 38: 9-Acetoxy-2-(2,3,5-tri-O-benzoyl-β-D-xylofuranosyl)ellipticinium bromide.

Example 39*:
9-Acetoxy-2-(2,3,5-tri-O-benzyl-β-D-arabinofuranosyl)ellipticinium bromide.
9-Acetoxy-2-(2,3,5-tri-O-benzyl-β-L-arabinofuranosyl)ellipticinium bromide.

* 1', 2'-cis-isomer of Example 39 was obtained in the same manner as in Example 33.

The results are shown in Table 1.

EXAMPLE 40

Preparation of 9-acetoxy-2-(2,3,4-tri-O-acetyl-D-xylopyranosyl)ellipticinium bromide

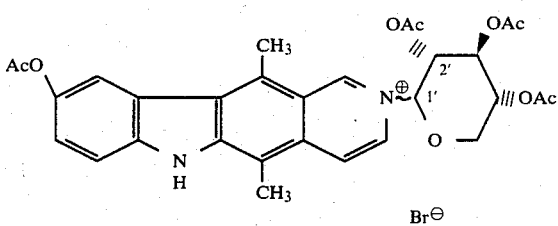

A 150 mg amount of 9-acetoxyellipticine, 335 mg of 2,3,4-tri-O-acetyl-α-D-xylopyranosyl bromide, and 169 mg of cadmium carbonate were suspended in 15 ml of nitromethane and the mixture was heated under reflux for 15 minutes. The mixture was then treated with silicagel column chromatography 180 g, elution solvent: 4–8% methanol-chloroform) and gel filtration column chromatography (Sephadex LH-20, 150 g, methanol) in the same manner as mentioned above. Thus, 188 mg of the desired compound was obtained.

The resultant compound had two types of stereoisomers against the 1-position of the sugar in the ratio of 1',2'-trans (β-form)/1',2'-cis(α-form) of 2.5/1.0. In Table 1, NMR data of the main product (i.e, β-form) are shown and the other data represent those of the mixture of the α- and β-form. The NMR spectra of the α-form are as follows:

1.97, 2.19, 2.27 (each 3H,s), 3.87 (2H,m) 4.84 (1H,m), 5.21 (1H,m), 5.39 (1H,brs) 6.60 (1H,brs), 8.27 (1H,d,J=2 Hz), 10.12(1H,s).

EXAMPLE 41

Preparation of 9acetoxy-2-(2,3,4-tri-O-acetyl-L-xylopyranosyl)ellipticinium bromide

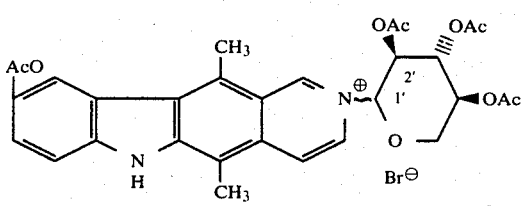

The desired compound was prepared by using 2,3,4-tri-O-acetyl-α-L-xylopyranosyl bromide in the same manner as in Example 40. This compound also had two types of stereoisomers on the 1-position of the sugar at a ratio of 1',2'-trans (β-form)/1', 2'-cis(α-form)=6.8/1.

EXAMPLE 42

Preparation of 9-acetoxy-2-(2,3,4-tri-O-acetyl-α-D-arabinopyranosyl)ellipticinium bromide

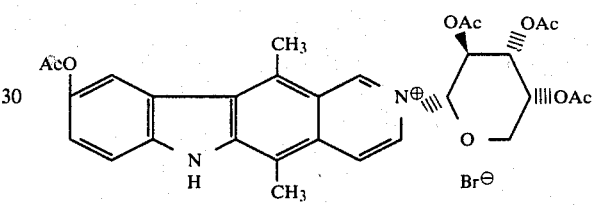

A 200 mg amount of 9-acetoxyellipticine, 446 mg of 2,3,4-tri-O-acetyl-β-D-arabinopyranosyl bromide, and 226 mg of cadmium carbonate were suspended in 20 ml of nitromethane and the mixture was heated under reflux for 15 minutes. After removing the insoluble matter, the reaction mixture was concentrated. A small amount of methanol was added to the residue obtained above to crystallize the product. The crystal was filtered and, after washing with chloroform, was dissolved in methanol. The methanol solution thus obtained was subjected to gel filtration column chromatography (Sephadex LH-20, 3.5 cmφ×40 cm) and was eluted with methanol. Thus, 254 mg of the desired compound was obtained in the form of red powder.

The results are shown in Table 1.

Similarly, when 2,3,4-tri-O-acetyl-β-L-arabinopyranosyl bromide was used, 9-acetoxy-2-(2,3,4-tri-O-acetyl-α-L-arabinopyranosyl)ellipticinium bromide was obtained.

EXAMPLES 43 AND 44

The following ellipticine derivatives were prepared in the same manner as in Example 42.

Example 43:
9-Acetoxy-2-(2,3,4-tri-O-acetyl-β-D-ribopyranosyl)ellipticinium bromide.
9-Acetoxy-2-(2,3,4-tri-O-acetyl-β-L-ribopyranosyl)ellipticinium bromide.

Example 44:
9-Acetoxy-2-(2,3,4-tri-O-acetyl-α-D-lyxopyranosyl)ellipticinium chloride.
9-Acetoxy-2-(2,3,4-tri-O-acetyl-α-L-lyxopyranosyl)ellipticinium chloride.

The results are shown in Table 1.

EXAMPLE 45

Preparation of
9-acetoxy-2-(2,3,4,6-tetra-O-acetyl-α-D-mannopyranosyl)ellipticinium bromide

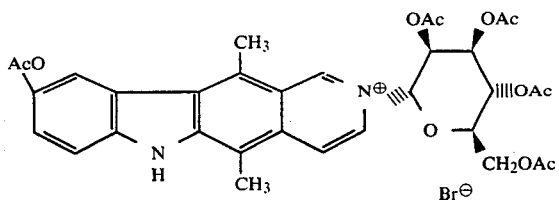

The desired compound 197 mg was prepared from 150 mg of 9-acetoxyellipticine, 600 mg of 2,3,4,6-tetra-O-acetyl-D-mannopyranosyl bromide, and 165 mg of cadmium carbonate in the same manner as mentioned above.

The results are shown in Table 1.

Similarly, 9-acetoxy-2-(2,3,4,6-tetra-O-acetyl-α-L-mannopyranosyl)ellipticinium bromide was obtained from 2,3,4,6-tetra-O-acetyl-L-mannopyranosyl bromide.

EXAMPLE 46 TO 49

The following ellipticine derivatives were prepared in the same manner as in Example 45. The results are shown in Table 1.

Example 46:
9-Acetoxy-2-(2,3,4,6-tetra-O-acetyl-β-D-allopyranosyl)ellipticinium bromide.
9-Acetoxy-2-(2,3,4,6-tetra-O-acetyl-β-L-talopyranosyl)ellipticinium bromide.
Example 47:
9-Acetoxy-2-(2,3,4,6-tetra-O-acetyl-α-D-talopyranosyl)ellipticinium bromide.
9-Acetoxy-2-(2,3,4,6-tetra-O-acetyl-α-L-talopyranosyl)ellipticinium bromide.
Example 48: 9-Acetoxy-2-(2,3,4,6-tetra-O-acetyl-β-L-galactopyranosyl)ellipticinium bromide.
Example 49: 9-Acetoxy-2-(2,3,4,6-tetra-O-acetyl-β-L-glucopyranosyl)ellipticinium bromide.

EXAMPLE 50

Preparation of
9-acetoxy-2-(2-acetamido-3,4,6-tri-O-acetyl-2-deoxy-β-D-glucopyranosyl)ellipticinium chloride

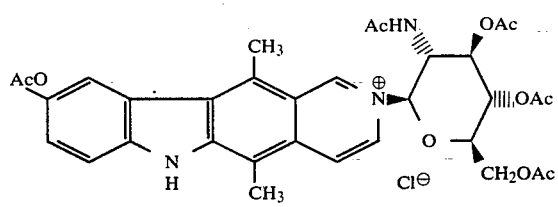

A 300 mg amount of 9-acetoxyellipticine, 300 mg of cadmium carbonate, and 917 mg of 2-acetamido-3,4,6-tri-O-acetyl-2-deoxy-α-D-glucopyranosyl chloride were suspended in 30 ml of nitromethane and the mixture was heated under reflux for 10 minutes. After removing the precipitate by filtration, the resultant residue was dissolved in methanol. The methanol solution was subjected to gel filtration column chromatography (Sephadex LH-20, 4,0 cmφ×35 cm), and was eluted with methanol. Thus, 219 mg (33% yield) of the desired compound was obtained.

The results are shown in Table 1.

EXAMPLE 51

Preparation of
9-acetoxy-2-(2-acetamido-3,4,6-tri-O-acetyl-2-deoxy-β-D-galactopyranosyl)ellipticinium bromide The desired compound was prepared in the same manner as in Example 50.

EXAMPLE 52

Preparation of 9-acetoxy-2-(methyl 2,3,4-tri-O-acetyl-β-D-glucuronopyranosyl)ellipticinium bromide

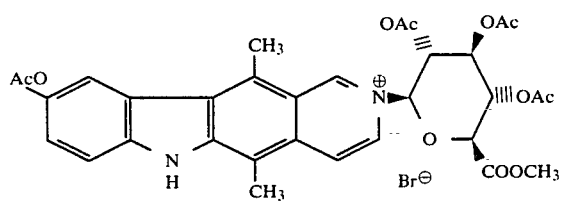

A 300 mg amount of 9-acetoxyellipticine, 762 mg of methyl (tri-O-acetyl-α-D-glucopyranosyl bromide)uronate, and 339 mg of cadmium carbonate were suspended in 30 ml of nitromethane and the suspension was heated under reflux for 15 minutes. The precipitate was removed by filtration. The resultant solution was subjected to silicagel column chromatography (silicagel: 600 ml) and was eluted with 8% methanol-chloroform solvent. The product was then subjected to gel filtration chromatography (Sephadex LH-20, 4.0 cmφ×38 cm) and was eluted with methanol.

Thus, 254 mg of the desired compound was obtained. The results are shown in Table 1.

EXAMPLE 53

Preparation of
2-(2,3,4-tri-O-acetyl-α-L-rhamnopyranosyl)-9-hydroxyellipticinium bromide

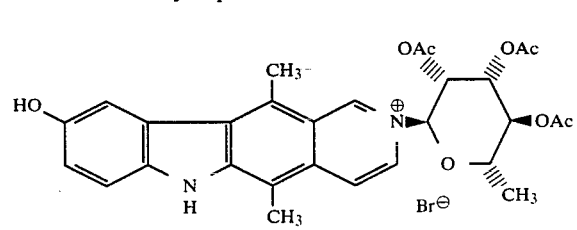

A 500 mg amount of 9-hydroxyellipticine, 650 mg of cadmium carbonate, and 1.35 g of α-bromoaceto-L-rhamnose were suspended in 55 ml of nitromethane and the resultant suspension was heated under reflux for 15 minutes.

After cooling, the insoluble matter was removed by filtration and the resultant solution was concentrated to obtain 1.4 g of the residue.

The residue was subjected to silicagel column chromatography (elution solvent: 5% methanol-chloroform) to obtain 380 mg of the desired compound. The compound was futher purified by Sephadex LH-20 column. Thus, 235 mg of the purified desired compound was obtained.

EXAMPLE 54

Preparation of 2-(2,3,5,-tri-O-benzoyl-β-D-xylofuranosyl)-9-hydroxyellipticinium chloride

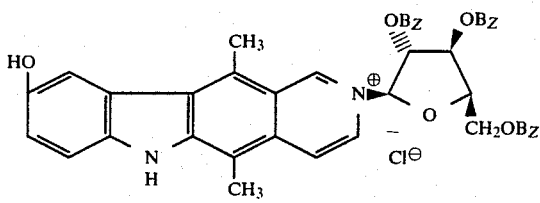

A 70 mg amount of 9-hydroxyellipticine, 70 mg of cadmium carbonate, and 208 mg of 2,3,5-tri-O-benzoyl-α-D-xylofuranosyl chloride were suspended in 7 ml of nitromethane and the mixture was heated under reflux for 10 minutes. After removing the precipitate matter by filtration, the residue obtained by concentration was subjected to silicagel column chromatography (Kieselgel 60, 50 ml) and then, gel filtration chromatography (Sephadex LH-20, 2.0 cm$\phi$×18 cm). The desired compound was obtained in an amount of 10.4 mg by elution with methanol.

The results are shown in Table 1.

Similarly, 2-(2,3,5-tri-O-benzoyl-β-L-xylofuranosyl)-9-hydroxyellipticinium chloride was obtained from 2,3,5-tri-O-benzoyl-α-L-xylofuranosyl chloride.

EXAMPLES 55 TO 61

The following ellipticine derivatives were prepared in the same manner as in Examples 53 and 54. The results are shown in Table 1.

Example 55: 2-(2,3,4-tri-O-benzoyl-α-D-arabinopyranosyl)-9-hydroyellipticinium bromide.

Example 56: 2-(2,3,5-tri-O-benzoyl-β-D-ribofuranosyl)-9- hydroxyellipticinium bromide.

Example 57: 2-(2,3,4,6-tetra-O-acetyl-β-D-glucopyranosyl)-9-hydroxyellipticinium bromide.

Example 58: 2-(2,3,4,6-tetra-O-acetyl-β-D-galactopyranosyl)-9-hydroxyellipticinium bromide.

Example 59: 2-(2,3,4-tri-O-benzoyl-α-L-arabinopyranosyl)-9-hydroxyellipticinium bromide.

Example 60: 2-(2,3,4-tri-O-acetyl-β-D-fucopyranosyl)-9-hydroxyellipticinium bromide.

Example 61: 2-(2,3,4,-tri-O-acetyl-β-L-fucopyranosyl)-9-hydroxyellipticinium bromide.

Example 62

Preparation of 2-β-D-galactopyranosyl-9-hydroxyellipticinium bromide

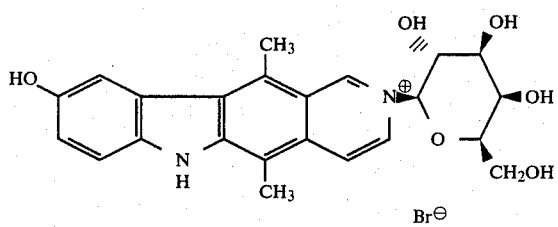

A 199 mg amount of the tetraacetyl derivative obtained in Example 58 was dissolved in 20 ml of methanol saturated with gaseous ammonia and was allowed to stand at a temperature of 0° C. for 16 hours. After removing the insoluble matter by filtration, methanol was distilled off in vacuo. The resultant residue was dissolved in 20 ml of methanol and 20 ml of ethyl acetate was added thereto. Thus, 23.4 mg of the desired compound was precipitated.

The results are shown in Table 1.

EXAMPLE 63

Preparation of 2-α-L-arabinofuranosyl-9-hydroxyellipticinium bromide

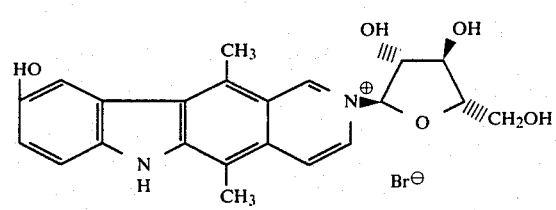

A 238 mg amount of 9-acetoxy-2-(2,3,5-tri-O-benzoyl-α-L-arabinofuranosyl)ellipticinium bromide was dissolved in 25 ml of methanol saturated with gaseous ammonia. The resultant solution was allowed to stand at a temperature of 0° C. to 10° C. for 15 hours. After concentrating, the residue was dissolved in methanol and ethyl acetate was added thereto. Thus, 107 mg of the desired compound was obtained by filtration.

The results are shown in Table 1.

EXAMPLE 64

Similarly in Example 63, 2-α-D-arabinofuranosyl-9-hydroxyellipticinium bromide was obtained from the tri-O-benzoyl-α-D-arabinofuranosyl compound.

EXAMPLES 66 TO 70

The following ellipticinium derivatives were prepared in the same manner as in Examples 62 and 63. The results are shown in Table 1.

Example 66:

2-α-D-Mannopyranosyl-9-hydroxyellipticinium bromide,

2-α-L-Mannopyranosyl-9-hydroxyellipticinium bromide.

Example 67:

2-α-D-Talopyranosyl-9-hydroxyellipticinium bromide.

2-α-L-Talopyranosyl-9-hydroxyellipticinium bromide.

Example 68: 2-β-L-Galactopyranosyl-9-hydroxyellipticinium bromide.

Example 69:

2-β-D-Allopyranosyl-9-hydroxyellipticinium bromide.

2-β-L-Allopyranosyl-9-hydroxyellipticinium bromide.

Example 70: 2-β-L-Glucopyranosyl-9-hydroxyellipticinium bromide.

EXAMPLE 71

Preparation of
2-α-L-rhamnopyranosyl-9hydroxyellipticinium bromide

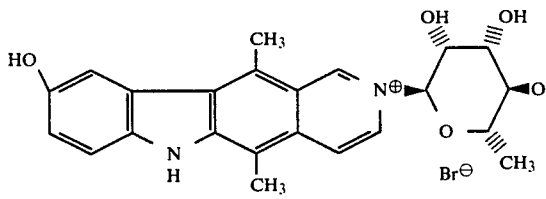

A 80 mg amount of 2-(2,3,4-tri-O-acetyl -α-L-rhamnopyranosyl)-9-hydroxyellipticinium bromide was dissolved in 8 ml of methanol saturated with gaseous ammonia. The resultant solution was allowed to stand in a refrigerator for 15 hours. After concentrating, the resultant concentrate was precipitated with methanolethyl acetate. Thus, 50 mg 80% yield) of the desired compound was obtained.

The results are shown in Table 1.

EXAMPLE 72

Preparation of
2-(2-deoxy-β-D-ribofuranosyl)-9-hydroxyellipticinium chloride

A 92 mg amount of the compound obtained in Example 32 was dissolved in 9.2 ml of methanol saturated with gaseous ammonia. The resultant solution was allowed to stand at a temperature of 0° C. to 4° C. overnight. After distilling off the solvent in vacuo, the resultant residue was dissolved in a small amount of methanol and, then was precipitated with ethyl acetate. Thus, 42 mg of the desired compound was obtained in the form of red powder.

The results are shown in Table 1.

EXAMPLE 73 TO 76

The following ellipticine derivatives were prepared in the same manner as in Examples 71 and 72. The results are shown in Table 1.

Example 73: 2-(5- deoxy-β-D-ribofuranosyl)-9-hydroxyellipticinium chloride.

Example 74: 2-(5-deoxy-α-L-arabinofuranosyl)-9-hydroxyellipticinium chloride.

Example 75: 2-β-D-fucopyranosyl-9-hydroxyellipticinium bromide.

Example 76: 2-β-L-fucopyranosyl-9-hydroxyellipticinium bromide.

EXAMPLE 77

Preparation of
2-β-D-xylofuranosyl-9-hydroxyellipticinium chloride

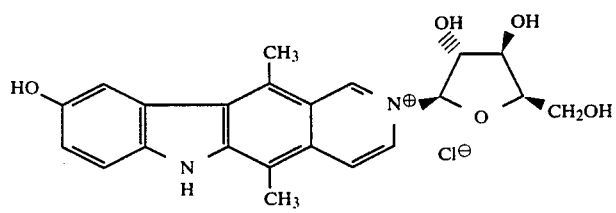

A 275 mg amount of 9-acetoxy-2-(2,3,5-tri-O-benzoyl-β-D-xylofuranosyl)ellipticinium chloride was dissolved in 30 ml of methanol saturated with gaseous ammonia. The resultant solution was allowed to stand at room temperature for 15 hours. After concentrating, the resultant residue was dissolved in a small amount of hot methanol and was precipitated with ethyl acetate. Thus, 142 mg (89% yield) of the desired compound was obtained. Similarly, when 2-(2,3,5-tri-O-benzoyl-β-L-xylofuranosyl) ellipticinium chloride as used, 2-β-L-xylofuranosyl-9-hydroxyellipticinium chloride was obtained.

The results are shown in Table 1.

EXAMPLE 78

2-β-D-xylofuranosyl-9-hydroxyellipticinium bromide was obtained in the same manner as in Example 77.

EXAMPLE 79

Preparation of
2-β-D-erythrofuranosyl-9-hydroxyellipticinium chloride

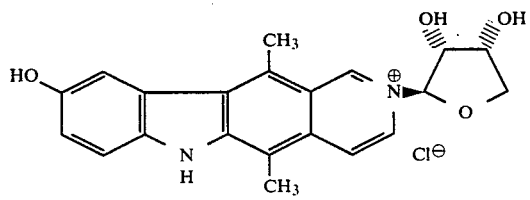

A 118 mg amount of the compound obtained in Example 29 was dissolved in 15 ml of methanol saturated with gaseous ammonia. The resultant solution was allowed to stand at a temperature of 0° C. to 5° C. for 12 hours. After distilling off the solvent in vacuo, the resultant residue was dissolved in methanol while heating and was precipitated with ethyl acetate. Thus, 61 mg (84% yield) of the desired compound was obtained in the form of reddish orange powder. The results are shown in Table 1.

At the same time, 7 mg of 2-α-D-erythrofuranosyl-9-hydroxyellipticinium chloride was obtained. This α-compound was identified by the NMR spectrum of the 1-position of the sugar.

δ6.45 ppm, d, J=6.5 Hz.

The other signals of NMR spectrum, IR spectrum, and Mass spectrum were the same as those of the β-compound.

Similarly, 2-β-L-erythrofuranosyl-9-hydroxyellipticinium chloride was obtained from 9-acetoxy-2-(2,3-di-O-benzoyl-β-L-erythrofuranosyl)ellipticinium chloride.

EXAMPLE 80

Preparation of 2-β-L-ribopyranosyl-9-hydroxyellipticinium bromide

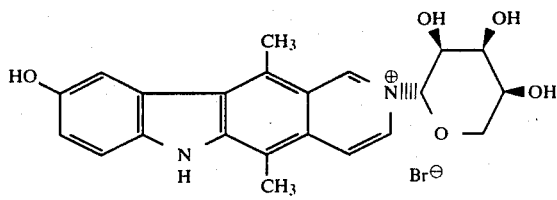

A 110 mg amount of 9-acetoxy-2-(2,3,4-tri-O-acetyl-β-L-ribopyranosyl)ellipticinium bromide was allowed to stand in 15 ml of methanol saturated with gaseous ammonia overnight in a refrigerator. The powder was precipitated with methanol-ethyl acetate. Thus, 71 mg of the desired compound was obtained.

The results are shown in Table 1.

EXAMPLE 81

2-β-D-ribopyranosyl-9-hydroxyellipticinium bromide was prepared in the same manner as in Example 80.

The results are shown in Table 1.

EXAMPLE 82

Preparation of 2-β-L-ribofuranosyl-9-hydroxyellipticinium bromide

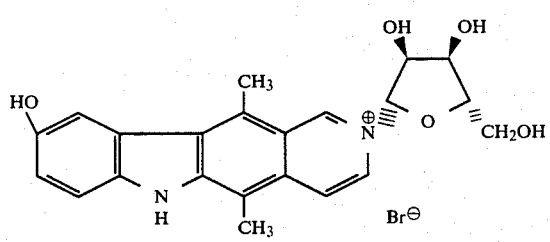

A 370 mg amount of the compound obtained in Example 37 was dissolved in 50 ml of methanol saturated with gaseous ammonia. The resultant solution was allowed to stand at a temperature of 0° C. to 5° C. for 15 hours. After concentrating, 170 mg of the desired compound was obtained in the form of red powder by using methanol-ethyl acetate.

The results are shown in Table 1.

EXAMPLE 83

2-β-D-ribofuranosyl-9-hydroxyellipticinium bromide was obtained in the same manner as in Example 82.

The results are shown in Table 1.

EXAMPLE 84

Preparation of 2-α-D-arabinopyranosyl-9-hydroxyellipticinium bromide

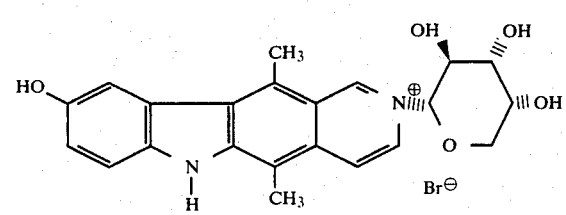

A 239 mg amount of 2-(2,3,4-tri-O-benzoyl-α-D-arabinopyranosyl)-9-hydroxyellipticinium bromide was allowed to stand in 23 ml of methanol saturated with gaseous ammonia to obtain 119 mg of the desired compound in the same manner as mentioned above.

The results are shown in Table 1.

EXAMPLE 85

2-α-L-arabinopyranosyl-9-hydroxyellipticinium bromide was prepared in the same manner as in Example 84.

EXAMPLE 86

Preparation of 2-α-D-lyxofuranosyl-9-hydroxyellipticinium chloride

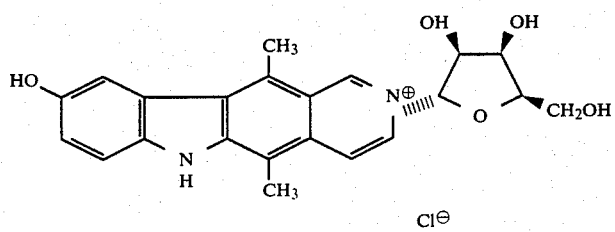

A 225 mg amount of the compound prepared in Example 34 was allowed to stand in 30 ml of methanol saturated with gaseous ammonia at a temperature of 0° C. to 10° C. for 15 hours. The solvent was removed in vacuo and the resultant residue was dissolved in a small amount of methanol. From this solution, powder was precipitated with ethyl acetate (about 200 ml in total).

Thus, 112 mg of the desired compound in the form of reddish orange powder. The results are shown in Table 1.

At the same time, 19 mg of 2-β-D-lyxofuranosyl-9-hydroxyellipticinium chloride having the following formula was obtained:

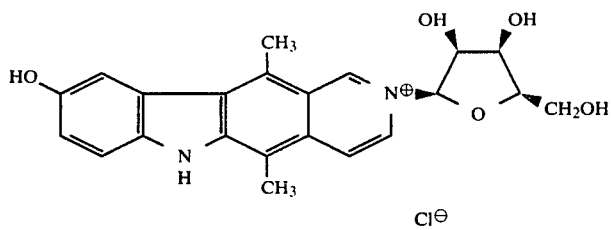

The NMR spectrum of the hydrogen atom of β-form in the 1-position of the sugar was as follows:
δ6.42 ppm, doublet, J=6.5 Hz.

EXAMPLE 87

2-α-L-lyxofuranosyl-9-hydroxyellipticinium chloride was prepared from 9-acetoxy-2-(2,3,5-tri-O-benzoyl-L-lyxofuranosyl)ellipticinium chloride α-form/β-form=6/1 in the same manner as in Example 86.

EXAMPLE 88

Preparation of 2-α-L-lyxopyranosyl-9-hydroxyellipticinium chloride

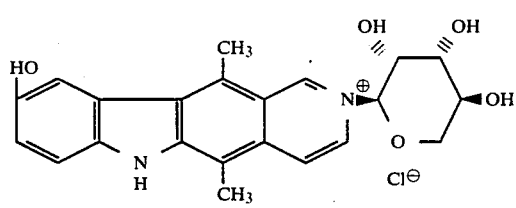

A 169 mg amount of 9-acetoxy-2-(2,3,4-tri-O-acetyl-α-L-lyxopyranosyl)ellipticinium chloride was treated with 17 ml of methanol saturated with gaseous ammonia in the same manner as mentioned above. Thus, 88 mg of the desired compound was obtained.

The results are shown in Table 1.

EXAMPLE 89

2-α-D-lyxopyranosyl-9-hydroxyellipticinium chloride was prepared in the same manner as in Example 88.
The results are shown in Table 1.

EXAMPLE 90

Preparation of 2-(2-acetamido-2-deoxy-β-D-glucopyranosyl)-9-hydroxyellipticinium chloride

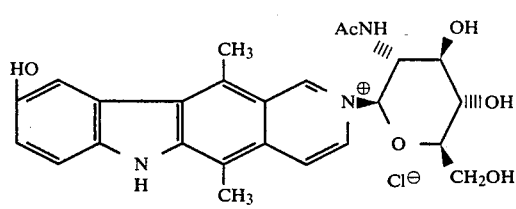

A 198 mg amount of 9-acetoxy-2-(2-acetamido-3,4,6-tri-O-acetyl-2-deoxy-β-D-glucopyranosyl)ellipticinium chloride was dissolved in 24 ml methanol saturated with gaseous ammonia and, then, the solution was allowed to stand at a temperature of 0° C. to 5° C. for 15 hours. Thus, 107 mg (72% yield) of the desired compound was obtained.

The results are shown in Table 1.

EXAMPLE 91

2-(2-acetamido-2-deoxy-β-D-galactopyranosyl)-9-hydroxyellipticinium chloride was prepared in the same manner as in Example 90.
The results are shown in Table 1.

EXAMPLE 92

Preparation of 2-β-D-glucuronamidopyranosyl-9-hydroxyellipticinium bromide

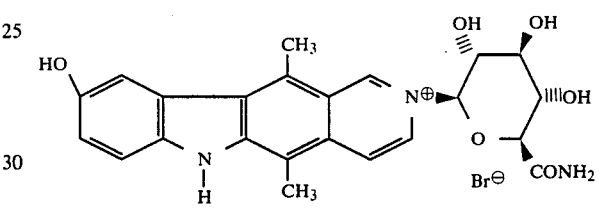

A 100 mg amount of 9-acetoxy-2-(methyl 2,3,4-tri-O-acetyl-β-D-glucuronopyranosyl)ellipticinium bromide was dissolved in 10 ml of methanol saturated with gaseous ammonia and, then, the solution was allowed to stand at a temperature of 0° C. to 5° C. for 15 hours. The residue was treated with methanol-ethyl acetate. Thus, 65 mg of the desired compound was obtained.
The results are shown in Table 1.

EXAMPLE 93

Preparation of 2-D-xylopyranosyl-9-hydroxyellipticinium bromide

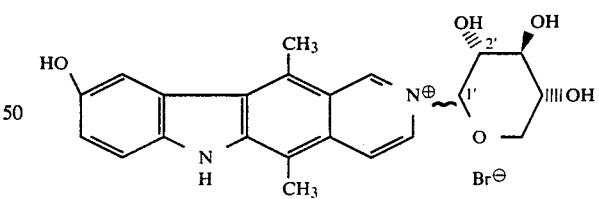

A 163 mg amount of the compound obtained in Example 40 was treated with 20 ml of methanol saturated with gaseous ammonia in the same manner as mentioned above. Thus, 79 mg of the desired compound (1',2'-trans-isomer and 1',2'-cis-isomer) was obtained.

The proportion ratio of the isomers was determined in the following two methods.

(1) Ratio determined by high pressure liquid chromatography
Column: Radial pack C-18 (available from Water's Co.).
Mobile phase:
(A) 100 mM ammonium acetate-30 mM Acetic acid.
(B) Methanol.
(C) Acetonitrile: A:B:C=2:0.4:0.6.

Flow rate: 3 ml/min.
Detection: 318 nm UV meter.

| Product | Retention time (min) | % |
|---|---|---|
| Main product | 3.74 | 74.6 |
| Another product | 5.13 | 25.2 |

(2) Ratio determined by integrated value of NMR spectrum of the 1-position of the sugar (360 MHz, DMSO-$d_6$)

Main product (1',2'-trans or β-form) δ:5.80 ppm, d, J=9 Hz.
Another product (1',2'-cis or α-form) δ:6.34 ppm, s
Ratio of 1',2'-trans/1',2'-cis=2.5/1.

The data in Table 1 represent the values of the main product in NMR spectrum and the values of the mixture in the other items.

The NMR spectrum of the α-isomer was as follows:
3.92 (1H,brs), 5.42 (1H,brs), 5.61 (1H,brs), 5.88 (1H,d) 6.34 (1H,s,1'-H), 7.54 (1H,d,J=9 Hz), 8.44 (1H,d,J=7.5 Hz) 9.99 (1H,s).

EXAMPLE 94

Preparation of 2-L-xylopyranosyl-9-hydroxyellipticinium bromide

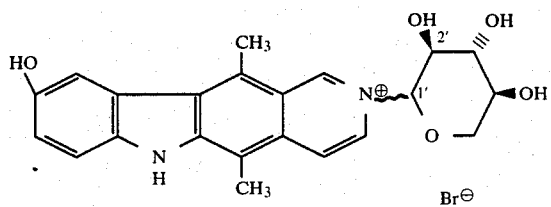

The desired compound was prepared from the compound obtained in Example 41 in the same manner as in Example 93.

This compound also had two isomers on the 1-position of the sugar.

(1) Ratio of the isomers by HPLC

| Product | Ratio | Retention time (min) |
|---|---|---|
| Main product (1',2'-trans or β-form) | 84.2 | 3.73 |
| Another product (1',2'-cis or α-form) | 15.6 | 5.14 |

(2) Ratio of the isomers by NMR spectrum (360 MHz, DMSO-$d_6$, H in 1-position of the sugar)

| Product | Ratio |
|---|---|
| Main product (δ: 5.79 ppm, d, J = 9.0 Hz) | 6.8 |
| Another product (δ: 6.34 ppm, s) | 1 |

The data in Table 1 represent the values of the main product in NMR spectrum and the values of the mixture in the other items.

EXAMPLE 95

Preparation of 2-α-L-rhamnopyranosyl-9-hydroxyellipticinium acetate

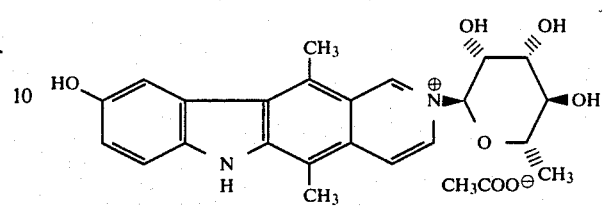

A 190 mg amount of 2-α-L-rhamnopyranosyl-9-hydroxyellipticinium bromide was dissolved in 40 ml of water and the resultant aqueous solution was passed through ion-exchange column (BIO-RAD, AG1-X8, acetate type, 1.5 cmφ×15 cm). The column was eluted with water. After concentrating, the resultant residue was treated with methanol-ethyl acetate to precipitate the powder. By filtration, 156 mg of the desired compound was obtained.

The results are shown in Table 1.

EXAMPLE 96

Preparation of 2-β-D-arabinofuranosyl-9-hydroxyellipticinium acetate

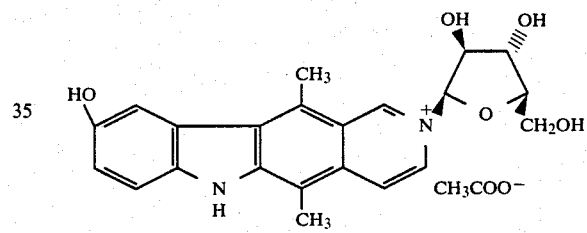

A 76 mg amount of 2-β-D-arabinofuranosyl-9-hydroxyellipticinium bromide was dissolved in water and the resultant aqueous solution was passed through ion-exchange column (BIO-RAD, AG1-X8, acetate type, 1.2 cmφ×11 cm).

Thus, 58 mg of the desired compound was obtained. The results are shown in Table 1.

Similarly, 2-β-L-arabinofuranosyl-9-hydroxyellipticinium acetate was prepared from 2-β-L-arabinofuranosyl-9-hydroxyellipticinium bromide.

EXAMPLES 97 to 104

The following ellipticine derivatives were prepared in the same manner as in Examples 95 and 96. The results are shown in Table 1.

Example 97: 2-(5-Deoxy-β-L-arabinofuranosyl)-9-hydroxyellipticinium acetate.

Example 98:
2-β-D-Ribopyranosyl-9-hydroxyellipticinium acetate.
2-β-L-Ribopyranosyl-9-hydroxyellipticinium acetate.

Example 99:
2-α-D-Lyxofuranosyl-9-hydroxyellipticinium acetate.
2-α-L-Lyxofuranosyl-9-hydroxyellipticinium acetate.

Example 100:
2-β-L-Fucopyranosyl-9-hydroxyellipticinium acetate.
2-β-D-Fucopyranosyl-9-hydroxyellipticinium acetate.

Example 101:

2-α-D-Arabinopyranosyl-9-hydroxyellipticinium acetate.
2-α-L-Arabinopyranosyl-9-hydroxyellipticinium acetate.
Example 102:
2-β-L-Galactopyranosyl-9-hydroxyellipticinium acetate.
2-β-D-Galactopyranosyl-9-hydroxyellipticinium acetate.
Example 103:
2-α-D-Lyxopyranosyl-9-hydroxyellipticinium acetate.
2-α-L-Lyxopyranosyl-9-hydroxyellipticinium acetate.
Example 104:
2-β-D-Xylofuranosyl-9-hydroxyellipticinium acetate.

EXAMPLE 105

Preparation of 2-(2,3,4,6-tetra-O-acetyl-β-D-glucopyranosyl)-9-hydroxyellipticinium acetate

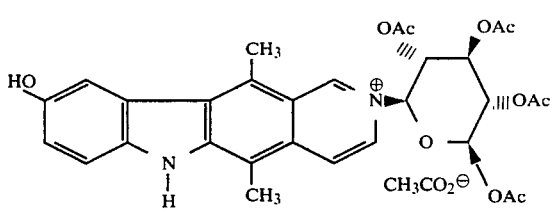

A 257 mg amount of 2-(2,3,4,6-tetra-O-acetyl-β-D-glucopyranosyl)-9-hydroxyellipticinium bromide (Example 57) was treated in ion-exchange column (BIO-RAD, AG1-X8, acetate type).

Thus, 214 mg of the desired compound was obtained.

EXAMPLE 106

Preparation of 2-L-xylopyranosyl-9-hydroxyellipticinium acetate

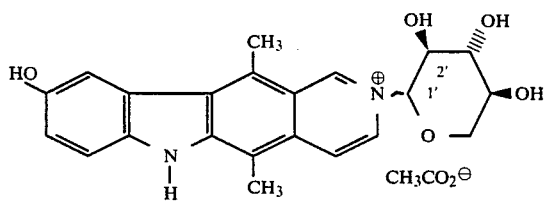

A 18 mg amount of the desired compound was obtained by treating 32.5 mg of the compound obtained in Example 94. The results are shown in Table 1.

The resultant compound had two isomers on the hydrogen atom in the 1-position of the sugar. The ratio was 6.8:1.

The NMR spectrum of the main product (i.e., 1',2'-trans or β-form) was as follows (360 MHz, DMSO-d$_6$, δ2.50 ppm, CD$_2$HSOCD$_3$ as internal standard):

1.66(3H,s), 2.69(3H,s), 3.08(3H,s), 3.68(3H,m), 4.06(1H,m) 5.67(1H,d,J=9 Hz,1'-H), 7.00(1H,dd,J=2,9 Hz) 7.50(1H, d,J=9 Hz), 7.75(1H, d,J=2 Hz), 8.11(1H,d,J=7.5 Hz) 8.27(1H, d.J=7.5 Hz), 9.64(1H,s).

2-D-xylopyranosyl-9-hydroxyellipticinium acetate was prepared from the compound obtained in Example 93 by the ion-exchange treatment in the same manner as mentioned above.

This compound had two isomers on the hydrogen atom in the 1-position of the sugar. The NMR spectrum of the main product (i.e., 1',2'-trans or β-form) was identical to that of 2-β-L-xylopyranosyl-9-hydroxyellipticinium acetate. The ratio of the two isomers was also identical to that of Example 93.

EXAMPLE 107

Preparation of 2-(2,3,4-tri-O-acetyl-α-L-rhamnopyranosyl)-9-hydroxyellipticinium bromide

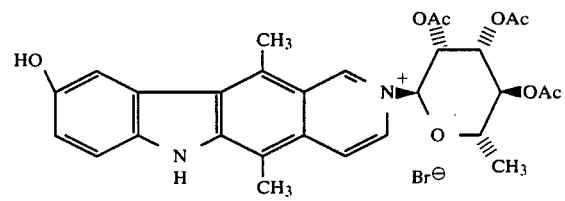

A 50 mg amount of 2-(2,3,4-tri-O-acetyl-α-L-rhamnopyranosyl)-9-methoxyellipticinium bromide (Example 25) was dissolved in 2.5 ml of dry methylene chloride and, then, 20 drops of iodotrimethylsilane were added thereto. The mixture was allowed to stand for 3 days to form a precipitate. The resultant precipitate was recovered by filtration. Thus, 42 mg (86% yield) of the desired compound was obtained.

The physical properties are shown in Example 53.

EXAMPLE 108

Preparation of 2-(2,3,5-tri-O-benzoyl-β-D-xylofuranosyl)-9-hydroxyellipticinium chloride

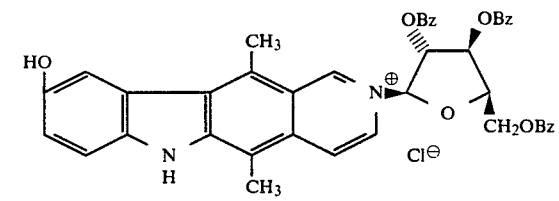

A 50 mg amount of 2-(2,3,5-tri-O-benzoyl-β-D-xylofuranosyl)-9-methoxyellipticinium chloride (Example 27) was dissolved in 2.5 ml of dry methylene chloride and, then, 20 drops of iodotrimethylsilane were added thereto. The mixture was allowed to stand for 3 days to form precipitate. The resultant precipitate was recovered by filtration. Thus, 44 mg (90% yield) of the desired compound was obtained.

The physical properties are shown in Example 54.

EXAMPLE 109

Preparation of 2-(5-deoxy-β-L-arabinofuranosyl)-9-hydroxyellipticinium chloride

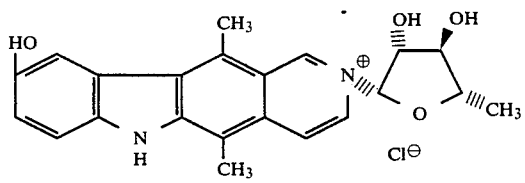

A 289 mg amount of 9-acetoxy-2-(2,3-di-O-benzyl-5-deoxy-β-L-arabinofuranosyl)ellipticinium chloride was dissolved in 19 ml of dry methylene chloride and, then, 109 drops of iodotrimethylsilane were added thereto. The mixture was allowed to stand at a temperature of 0° C. to 5° C. for 15 hours. The precipitate thus formed was recovered and was then dissolved in 40 ml of methanol saturated with gaseous ammonia. The solution was allowed to stand at a temperature of 0° C. to 5° C. for 4 hours. After concentrating, the desired compound was obtained in the form of powder by treating the residue with methanol-ethyl acetate. The yield was 150 mg (81%).

The results are shown in Table 1.

EXAMPLES AND 110 AND 111

The following ellipticine derivatives were prepared in the same manner as in Example 109. The results are shown in Table 1.

Example 110: 2-β-D-Arabinofuranosyl-9-hydroxyellipticinium bromide.

Example 111: 2-β-L-Arabinofuranosyl-9-hydroxyellipticinium bromide

EXAMPLE 112

Preparation of 2-β-D-glucopyranosyl-9-hydroxyellipticinium acetate

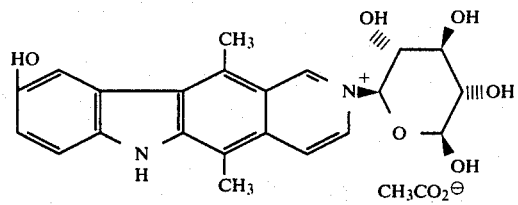

A 63.7 g amount of the tetraacetyl derivative obtained in Example 105 was dissolved in 8.5 ml of methanol saturated with gaseous ammonia. The solution was allowed to stand at a temperature of 0° C. overnight. The resultant dark red precipitate was removed by filtration and the filtrate was concentrated to obtain the powder product.

The powder product was then subjected to Sephadex LH-20 column (solvent: methanol). Thus, 20 mg of the purified product was obtained. The physical properties are shown in Table 1.

TABLE 1

| Example No. | 1 | 2 | 3 | 4 |
|---|---|---|---|---|
| R | AcO, OAc, OAc, OAc structure (pyranose with OAc at 2',3',4' and CH$_2$OAc at 6') | HO, OH, OH, OH structure (pyranose with OH at 2',3',4' and CH$_2$OH at 6') | BzO, OBz, OBz structure (furanose with OBz at 2',3' and CH$_2$OBz at 5') | HO, OH, OH structure (furanose with OH at 2',3' and CH$_2$OH at 5') |
| X$^-$ | Br$^-$ | Br$^-$ | Br$^-$ | Br$^-$ |
| Crystalline form Specific rotatory power [α]$_D$ | Amorphous orange powder −18° (C = 0.17, EtOH) | Amorphous orange powder +53° (C = 0.12, EtOH) | Amorphous orange powder −180° (C = 0.19, MeOH) | Amorphous orange powder −150° (C = 0.24, MeOH) |
| Infrared absorption (KBr, cm$^{-1}$) | 1750, 1590, 1430, 1370, 1240 | 3300, 1635, 1590, 1420, 1235 | 1729, 1606, 1450, 1425, 1261, 1113, 711 | 3238, 1598, 1425, 1384, 1253, 1105, 753 |
| Ultraviolet absorption (λ$_{max}^{EtOH}$, nm) | 244 (ε21000) 250 (ε20000) 286 (ε21000) 317 (ε58000) | 244 (ε20000) 251 (ε19000) 313 (ε62000) | 230 (ε49000) 245 (ε22000) 313 (ε63000) | 204 (ε19000) 245 (ε22000) 313 (ε63000) |
| Mass spectrum (SIMS, m/z) | 577 | 409 | 619 | 379 |
| Proton NMR (DMSO-d$_6$, δ in ppm, CD$_2$HSOCD$_3$ proton chemical shift (δ 2.50) was used as internal standard. Intensity of NMR magnetic field was indicated in each compound) | [C$_{31}$H$_{33}$O$_9$N$_2$]$^+$ 1.81, 1.98, 2.01, 2.30, (each 3H,s) 2.91 (3H,s) 3.38 (3H,s) 4.25 (2H,m) 4.76 (1H,t) 5.56 (3H,m) 6.45 (1H,d,J=8.5Hz, 1'-H) 7.46 (1H,ddd,J=8, 7, 2Hz) 7.74 (2H,m) 8.54 (1H,d, J=8Hz) 8.58 (2H,s) 10.14 (1H, s) 12.46 (1H,brs) (360MHz) | [C$_{23}$H$_{25}$O$_5$N$_2$]$^+$ 2.83, (3H,s) 3.70 (3H,s) 3.89 (3H,s) 4.88 (1H,t) 4.98, 5.24, 5.62 (each 1H,d) 5.87 (1H,d,J =9Hz) 7.41 (1H,dt,J =2.6Hz) 7.67 (2H,m) 8.43 (1H,d, J=7.5Hz) 8.53 (2H,m) 10.07 (1H,s) 12.28 (1H,brs) (360MHz) | [C$_{43}$H$_{35}$O$_7$N$_2$]$^+$ 2.90 (3H,s) 4.98 (2H,m) 5.18 (1H,q) 6.12 (1H,t) 6.19 (1H, t) 7.05 (1H,d,J=5Hz, 1'-H) 8.48 (1H,d,J=8Hz) 8.54 (1H, d,J=7.5Hz) 8.77 (1H,d,J=7.5Hz) 10.25 (1H,s) 12.44 (1H,brs) (300MHz) | [C$_{23}$H$_{23}$O$_4$N$_2$]$^+$ 2.90 (3H,s) 3.80, 3.93, (each 1H) 4.26 (2H,brs), 4.37 (1H, brs) 5.57, 5.65, 6.00 (each 1H,brs) 6.30 (1H,d,J=5Hz,1'-H) 7.43 (1H,dd,J=8,7Hz) 7.71 (2H, m) 8.51 (1H,d,J=8Hz) 8.58 (1H, d,J=7.5Hz) 8.71 (1H,d,J=7.5Hz) 10.32 (1H,s) 12.15 (1H,brs) (300MHz) |
| Elementary analysis Molecular formula Calc. (C, H, N) % Found (C, H, N) % | C$_{31}$H$_{33}$N$_2$O$_9$Br 56.62, 5.06, 4.26 56.69, 5.24, 4.06 | C$_{23}$H$_{25}$N$_2$O$_5$Br 56.45, 5.15, 5.73 56.18, 5.32, 5.61 | C$_{43}$H$_{35}$N$_2$O$_7$Br 66.93, 4.57, 3.63 67.15, 4.60, 3.52 | C$_{22}$H$_{23}$N$_2$O$_4$Br 57.52, 5.05, 6.10 57.24, 4.96, 5.85 |

| Example No. | 5 | 6 | 7 | 8 |
|---|---|---|---|---|
| R | AcO, OAc, OAc structure (pyranose with OAc at 2',3',4' and CH$_3$ at 5') | HO, OH, OH structure (pyranose with OH at 2',3',4' and CH$_3$ at 5') | AcO, OAc, OAc structure (pyranose with OAc at 2',3',4' and CH$_3$ at 5') | HO, OH, OH structure (pyranose with OH at 2',3',4' and CH$_3$ at 5') |
| X$^-$ | Br$^-$ | CH$_3$CO$_2^-$ | Br$^-$ | Br$^-$ |
| Crystalline form Specific rotatory power [α]$_D$ | Amorphous orange powder −63° (C = 0.21, EtOH) | Amorphous orange powder +43° (C = 0.24, EtOH) | Amorphous orange powder −4.7° (C = 0.17, MeOH) | Amorphous orange powder −170° (C = 0.15, H$_2$O) |
| Infrared absorption | 1750, 1600, 1420, 1380, 1370 | 3200, 1640, 1600, 1580, 1420 | 1754, 1647, 1598, 1434, 1376, | 3345, 1639, 1598, 1434, 1253, |

TABLE 1-continued

| | | | | | |
|---|---|---|---|---|---|
| Infrared absorption (KBr, cm$^{-1}$) | 1240 | | 1240 | | 1163, 1105 |
| Ultraviolet absorption ($\lambda_{max}^{EtOH}$, nm) | 229 ($\epsilon$18000) 243 ($\epsilon$24000) 252 ($\epsilon$23000) 286 ($\epsilon$24000) 317 ($\epsilon$61000) | | 207 ($\epsilon$24000) 244 ($\epsilon$23000) 251 ($\epsilon$23000) 313 ($\epsilon$70000) | | 1253, 1220 230 ($\epsilon$17000) 245 ($\epsilon$23000) 252 ($\epsilon$22000) 286 ($\epsilon$23000) 316 ($\epsilon$62000) |
| Mass spectrum (SIMS, m/z) | 577 | | 409 | | 519 |
| Proton NMR (DMSO-d$_6$, δ in ppm, CD$_3$SOCD$_3$ proton chemical shift (δ 2.50) was used as internal standard, Intensity of NMR magnetic field was indicated in each compound) | [C$_{31}$H$_{33}$O$_9$N$_2$]$^+$ 1.81, 2.02, 2.07, 2.10, (each 3H,s) 2.90 (3H,s) 3.42 (3H,s) 4.27 (2H,m) 4.45 (1H,m) 5.59 (2H,m) 5.94 (1H,t) 6.43 (1H,d, J=9Hz,1'-H) 7.46 (1H,dt,J=2,6Hz) 7.73 (2H,m) 8.54 (2H,m) 8.73 (1H,d,J=7.5Hz) 10.21 (1H, s) 12.42 (1H,brs) (360MHz) | | [C$_{25}$H$_{28}$N$_2$O$_7$]$^+$ 1.70, (3H,s) 2.80 (3H,m) 3.23 (3H,s) 5.87 (1H,d,J=8.5Hz, 1'-H) 7.37 (1H,t,J=7Hz) 7.63 (1H,t,J=7Hz) 7.69 (1H,d,J=7Hz) 8.34 (1H,d,J=7.5Hz) 8.38 (1H, d,J=7.5Hz) 8.53 (1H,d,J=7Hz) 9.98 (1H,s) (360MHz) | | [C$_{23}$H$_{25}$O$_5$N$_2$]$^+$ 1.26 (3H,d,J=6.5Hz) 1.80 (3H,s) 2.00, 2.31 (each 3H,s) 2.88 (3H,s) 3.38 (3H,s) 4.57 (1H,q) 5.39 (1H,d,) 5.50 (2H,m) 6.44 (1H,t,J=8Hz,1'-H)7.46 (1H, ddd,J=8,7,2Hz) 7.74 (2H,m) 8.53 (1H,d,J=8Hz) 8.57 (2H,s) 10.15 (1H,s) 12.46 (1H,brs) (300MHz) |
| Elementary analysis Molecular formula | C$_{31}$H$_{33}$N$_2$O$_9$Br | | C$_{25}$H$_{28}$N$_2$O$_7$ | | C$_{29}$H$_{31}$N$_2$O$_7$Br |
| Calc. (C, H, N) % | 56.62, 5.06, 4.26 | | 64.09, 6.02, 5.98 | | 58.10, 5.21, 4.67 |
| Found (C, H, N) % | 56.49, 5.21, 3.99 | | 64.05, 6.33, 6.21 | | 58.32, 5.03, 4.51 |

| Example No. | 9 | 10 | 11 | 12 |
|---|---|---|---|---|
| R | AcO, OAc, CH$_3$ structure with OAc substituent | HO, OH, CH$_3$ structure with OH substituent | AcO, OAc, CH$_3$ structure with OAc substituent | HO, OH, CH$_3$ structure with OH substituent |
| X$^-$ | Br$^-$ | Br$^-$ | Br$^-$ | Br$^-$ |
| Crystalline form | Amorphous orange powder | Amorphous orange powder | Amorphous orange powder | Amorphous orange powder |
| Specific rotatory power [α]$_D$ | −6.2° (C = 0.21, MeOH) | +180° (C = 0.11, H$_2$O) | −13° (C = 0.19, EtOH) | −20° (C = 0.11, EtOH) |
| Infrared absorption (KBr, cm$^{-1}$) | 1754, 1647, 1598, 1434, 1376 1235, 1220 | 3345, 1639, 1598, 1434, 1253 1163, 1105 | 1750, 1600, 1430, 1370, 1240, | 3200, 1640, 1600, 1420, 1240, |
| Ultraviolet absorption ($\lambda_{max}^{EtOH}$, nm) | Same as in compound 7 | Same as in compound 8 | 230 ($\epsilon$16000) 244 ($\epsilon$22000) 252 ($\epsilon$21000) 286 ($\epsilon$21000) 316 ($\epsilon$61000) | 204 ($\epsilon$19000) 244 ($\epsilon$23000) 250 ($\epsilon$23000) 312 ($\epsilon$74000) |
| Mass spectrum (SIMS, m/z) | 519 | 393 | 519 | 393 |
| Proton NMR (DMSO-d$_6$, δ in ppm, CD$_3$SOCD$_3$ proton chemical shift (δ 2.50) was used as internal standard, Intensity of NMR | [C$_{29}$H$_{31}$O$_7$N$_2$]$^+$ Same as in compound 7 | [C$_{23}$H$_{25}$O$_4$N$_2$]$^+$ Same as in compound 8 | [C$_{29}$H$_{31}$O$_7$N$_2$]$^+$ 1.54 (3H,d,J=6.5Hz) 1.86, 2.18, 2.24 (each 3H,s) 2.90 (3H,s) 3.43 (3H,s) 4.53 (1H,m) 4.98 (1H,t) 5.52 (1H,t) 5.81 (1H,dd,J=3, 8.5Hz) 6.69 (1H,d, J=8.5Hz,1'-H) 7.46 (1H,ddd, J=8,7,2Hz) 7.73 (2H,m) 8.55 | [C$_{23}$H$_{25}$O$_4$N$_2$]$^+$ 1.54 (3H,d,J=6Hz) 2.90 (3H,s) 3.37 (3H,s) 3.71, 4.00, 4.11, 4.33 (each 1H,m) 5.41, 5.47, 5.65 (each 1H,d) 6.26 (1H,d, J=9Hz,1'-H) 7.43 (1H,ddd,J=8, 7.2Hz) 7.73 (2H,m) 8.50 (1H,d, J=8Hz) 8.54 (1H,d,J=7.5Hz) 8.63 |

TABLE 1-continued

| | | | | | |
|---|---|---|---|---|---|
| magnetic field was indicated in each compound) | | | | (2H,m) 8.66 (1H,d,J=7.5Hz) 10.17 (1H,s) 12.44 (1H,brs) (360MHz) | (1H,d,J=7.5Hz) 10.14 (1H,s) 12.34 (1H,brs) (360MHz) |
| Elementary analysis Molecular formula | C$_{29}$H$_{31}$N$_2$O$_7$Br | C$_{23}$H$_{25}$N$_2$O$_4$Br | | C$_{29}$H$_{31}$N$_2$O$_7$Br | C$_{23}$H$_{25}$N$_2$O$_4$Br |
| Calc. (C, H, N) % | 58.10; 5.21, 4.67 | 58.35, 5.32, 5.92 | | 58.10; 5.21, 4.67 | 58.35, 5.32, 5.92 |
| Found (C, H, N) % | 58.12, 5.25, 4.81 | 58.25, 5.41, 5.72 | | 57.89, 5.33, 4.70 | 58.41, 5.49, 5.85 |
| Example No. | 13 | | | 14 | 14 |
| R | (structure: furanose with OBz at 2', 3' and CH$_2$OBz at 5') | (structure: furanose with OBz at 2', 3' and CH$_2$OBz at 5') | | (structure: furanose with OH at 2', 3' and OH at 5') | (structure: furanose with OH at 3', 4' and OH at 5') |
| X$^-$ | Cl$^-$ | Cl$^-$ | | Cl$^-$ | Cl$^-$ |
| Crystalline form Specific rotatory power [α]$_D$ | Amorphous yellow powder −76° (C = 0.23, MeOH) | Amorphous yellow powder +80° (C = 0.19, MeOH) | | Amorphous yellow powder −39° (C = 0.19, 1(v/v %) CF$_3$CO$_2$H/H$_2$O) | Amorphous yellow powder +40° (C = 0.21, 1% CF$_3$COOH/H$_2$O) |
| Infrared absorption (KBr, cm$^{-1}$) | 1730, 1720, 1650, 1600, 1460, 1430, 1250, 1100, 710 | Same as in the left | | 3200, 1640, 1595, 1575, 1420, 1240, 1090, 750 | Same as in the left |
| Ultraviolet absorption (λ$_{max}^{EtOH}$, nm) | 232 (ε55000) 286 (ε25000) 316 (ε70000) | | | 207 (ε21000) 244 (ε24000) 311 (ε(74000) | |
| Mass spectrum (SIMS, m/z) | 691 [C$_{43}$H$_{35}$N$_2$O$_7$]$^+$ | | | 379 [C$_{32}$H$_{23}$N$_2$O$_4$]$^+$ | |
| Proton NMR (DMSO-d$_6$, δ in ppm, CD$_3$SOCD$_3$ proton chemical shift (δ 2.50) was used as internal standard, Intensity of NMR magnetic field was indicated in each compound) | 2.90 (3H,s) 4.96 (1H,dd) 5.14 (1H,dd) 5.42 (1H, quintet) 6.12 (2H,m) 7.05 (1H,s,1'-H) 7.33–8.25 (18H,m) 8.47 (1H,d,J=8Hz) 8.56 (1H,d, J=7.5Hz) 8.80 (1H,d,J=7.5Hz) 10.16 (1H,s) 12.49 (1H,brs) | (1H,dt,J=1.5,6.0Hz) 7.66 | | 2.83 (3H,s) 3.27 (3H,s) 3.98 (2H,m) 4.16 (1H,s) 4.35 (1H,s) 4.50 (1H,m) 5.12 (1H,t) 5.74 (1H,brs) 6.50 1H,brs) 6.35 (1H,s,1'-H) 7.38 (2H,m) 8.42 (1H,md,J=8.0Hz, 10-H) 8.48 (1H,d,J=7.5Hz) 8.66 (1H,d,J=7.5Hz) 10.15 (1H,s) 12.28 (1H,brs) | |
| Elementary analysis Molecular formula Calc. (C, H, N) % Found (C, H, N) % | — | — | | — | — |
| Example No. | 15 | 16 | | 17 | 18 |
| R | (structure: pyranose with OAc at 2', 3', 4', 5' and OAc at 6') | (structure: pyranose with OH at 2', 3', 4', 5' and OH at 6') | | (structure: furanose with BzO at 2', OBz at 3', 4' and OBz at 5') | (structure: furanose with HO at 2', OH at 3', 4' and OH at 5') |
| X$^-$ | Br$^-$ | Br$^-$ | | Br$^-$ | Br$^-$ |

TABLE 1-continued

| | Example No. 19 | Example No. 20 | Example No. 21 | Example No. 22 |
|---|---|---|---|---|
| R | AcO, OAc, OAc structure (6'-CH₃, positions 2',3',4',5') | HO, OH structure (positions 2',3',4',5',6'-CH₃) | AcO, OAc structure (positions 2',3',4',5'-CH₃) | HO, OH structure (positions 2',3',4',5'-CH₃) |
| X⁻ | Br⁻ | Br⁻ | Br⁻ | Br⁻ |
| Crystalline form | Amorphous yellow powder | Amorphous yellow powder | Amorphous red powder | Amorphous red powder |
| Specific rotatory power [α]$_D$ | +5.7° (C = 0.23, MeOH) | +45° (C = 0.11, MeOH) | −180° (C = 0.29, MeOH) | −180° (C = 0.083, H₂O) |
| Infrared absorption (KBr, cm⁻¹) | 1754, 1639, 1598, 1491, 1434, 1376, 1229 | 3386, 1647, 1598, 1483, 1417, 1311, 1261, 1220, 1097 | 1729, 1647, 1598, 1483, 1270, 1106, 712 | 3394, 1638, 1598, 1483, 1425, 1302, 1261, 1220, 1106 |
| Ultraviolet absorption (λ$_{max}$ EtOH, nm) | 226 (ε16000) 249 (ε24000) 256 (ε24000) 268 (ε23000) 326 (ε51000) | 226 (ε14000) 255 (ε22000) 265 (ε21000) 280 (ε20000) 321 (ε49000) | 230 (ε49000) 269 (ε25000) 324 (ε50000) | 226 (ε16000) 254 (ε24000) 265 (ε24000) 280 (ε21000) 321 (ε54000) |
| Mass spectrum (SIMS, m/z) | 607 | 439 | 721 | 409 |
| Proton NMR (DMSO-d₆, δ in ppm, CD₂HSOCD₃ proton chemical shift (δ 2.50) was used as internal standard Intensity of NMR magnetic field was indicated in each compound) | [C₃₂H₃₅O₁₀N₂]⁺ 1.81, 1.98, 2.01, 2.30, (each 3H,s) 2.87 (3H,s) 3.96 (3H,s) 4.24 (2H,m) 4.75 (1H,t) 5.56 (3H,m) 6.44 (1H,d,J=8.5H,1'-H) 7.37 (1H,dd,J=2,9Hz) 7.67 (1H, d,J=9Hz) 7.98 (1H,d,J=2Hz) 8.54 (2H,s) 10.13 (1H,s) 12.25 (1H,brs) (300MHz) | [C₂₄H₂₇O₆N₂]⁺ 2.87 (3H,s) 3.95 (3H,s) 4.85 (1H,t) 4.97, 5.25, 5.62 (each 1H,d) 5.83 (1H,dd,J=2,9Hz) 7.35 (1H,m) 6.44 (1H,d,J=9Hz,1'-H) 7.35 (1H,dd,J=2,9Hz) 7.65 (1H, d,J=9Hz) 7.97 (1H,d,J=2Hz) 8.54 (2H,s) 10.11 (1H,s) (300MHz) | [C₄₄H₃₇O₈N₂]⁺ 2.86 (3H,s) 3.27 (3H,s) 3.94 (3H,s) 4.98 (2H,m) 5.18 (1H,m) 6.11 (1H,t) 6.19 (1H,t) 7.05 (1H,d,J=5Hz,1'-H) 7.34 (1H,dd, J=2,9Hz) 8.49 (1H,d,J=7.5Hz) 8.73 (1H,d,J=2,9Hz) 10.23 (1H, s) 12.28 (1H,brs) (300MHz) | [C₂₃H₂₅O₅N₂]⁺ 2.86 (3H,s) 3.95 (2H,s) 4.26 (2H,m) 4.35 (1H,brs) 5.50, 5.86 (each 1H,d) 5.63 (1H,t) 6.29 (1H,d,J=5Hz,1'-H) 7.33 (1H,dd,J=2,9Hz) 7.63 (1H,d, J=9Hz) 7.94 (1H,d,J=2Hz) 8.54 (1H,d,J=7.5Hz) 8.67 (1H,d, J=7.5Hz)10.28 (1H,s) 12.14 (1H,brs) (300MHz) |
| Elementary analysis Molecular formula | C₃₂H₃₅N₂O₁₀Br | C₂₄H₂₇N₂O₆Br | C₄₄H₃₇N₂O₈Br | C₂₃H₂₅N₂O₅Br |
| Calc. (C, H, N) % Found (C, H, N) % | 55.90, 5.13, 4.07 55.85, 5.25, 4.18 | 55.50, 5.24, 5.39 55.46, 5.29, 5.18 | 65.92, 4.65, 3.49 66.13, 4.59, 3.52 | 56.45, 5.15, 5.73 56.36, 5.17, 5.65 |

| | Example No. 21 | Example No. 22 |
|---|---|---|
| R | AcO, OAc structure | HO, OH structure |
| X⁻ | Br⁻ | Br⁻ |
| Crystalline form | Amorphous red powder | Amorphous red powder |
| Specific rotatory power [α]$_D$ | +22° (C = 0.25, MeOH) | +46° (C = 0.19, MeOH) |
| Infrared absorption (KBr, cm⁻¹) | 1754, 1647, 1598, 1491, 1425, 1376, 1220 | 3402, 1639, 1598, 1483, 1417, 1311, 1261, 1220, 1155 |
| Ultraviolet absorption (λ$_{max}$ EtOH, nm) | 227 (ε15000) 256 (ε23000) 326 (ε49000) 250 (ε23000) 267 (ε23000) | 227 (ε15000) 266 (ε24000) 321 (ε52000) 255 (ε23000) 279 (ε21000) |
| Mass spectrum (SIMS, m/z) | 549 | 423 |
| Proton NMR | [C₃₀H₃₃O₈N₂]⁺ 1.26 (3H,d,J=6.5Hz) 1.80, 2.00, 2.30 (each 3H,s) 2.86 (3H,s) 3.33 (3H,s) 3.96 (3H,s) | [C₂₄H₂₇O₅N₂]⁺ 1.30 (3H,d,J=6.5Hz) 2.85 (3H, s) 3.32 (3H,s) 3.66 (2H,m) 3.88 (1H,m) 4.04 (1H,q) 3.96 |

TABLE 1-continued

| | | | | |
|---|---|---|---|---|
| chemical shift (δ 2.50) was used as internal standard, Intensity of NMR magnetic field was indicated in each compound) | (1H,m) 5.58 (2H,m) 5.94 (1H,t) 6.41 (1H,dd,J=2,9Hz) 7.66 (1H,d, J=9Hz) 7.98 (1H,brs) 8.50 (1H, d,J=7.5Hz) 8.70 (1H,d,J=7.5Hz) 10.18 (1H,s) 12.30 (1H,brs) (300MHz) | J=9Hz,1'-H) 7.33 (1H,dd,J=2, 9Hz) 7.62 (1H,d,J=9Hz) 7.92 (1H,brs) 8.46 (1H,d,J=7.5Hz) 8.59 (1H,d,J=7.5Hz) 10.07 (1H, s) 12.16 (1H,brs) (300MHz) | 4.55 (1H,q) 5.39 (1H,d) 5.48 (2H,m) 6.42 (1H,d,J=8.5Hz,1'-H) 7.36 (1H,dd,J=2,9Hz) 7.66 (1H, d,J=9Hz) 7.97 (1H,d,J=2Hz) 8.52 (2H,s) 10.13 (1H,s) 12.33 (1H,brs) (300MHz) | (3H,s) 4.97, 5.21, 5.56 (each 1H,d) 5.82 (1H,d,J=8.5Hz,1'-H) 7.34 (1H,dd,J=2,9Hz) 7.64 (1H, d,J=9Hz) 7.95 (1H,d,J=2Hz) 8.53 (2H,s) 10.08 (1H,s) 12.14 (1H,brs) (300MHz) |
| Elementary analysis Molecular formula | C37H35N2O10Br | C24H27N2O6Br | C30H33N2O8Br | C24H27N2O5Br |
| Calc. (C, H, N) % | 55.90, 5.13, 4.07 | 55.50, 5.24, 5.39 | 57.24, 5.28, 4.45 | 57.26, 5.41, 5.57 |
| Found (C, H, N) % | 56.11, 4.98, 4.26 | 55.48, 5.29, 5.61 | 57.09, 5.12, 4.60 | 57.51, 5.24, 5.65 |
| Example No. | 23 | 24 | 25 | 26 |
| R | AcO, OAc, ⫼OAc, CH3 structure | HO, OH, ⫼OH, CH3 structure | AcO, OAc, ⫼OAc, CH3 structure | HO, OH, ⫼OH, CH3 structure |
| X⁻ | Br⁻ | Br⁻ | Br⁻ | Br⁻ |
| Crystalline form | Amorphous red powder | Amorphous red powder | Amorphous red powder | Amorphous red powder |
| Specific rotatory power [α]D | −19° (C = 0.15, MeOH) | −50° (C = 0.21, MeOH) | −47° (C = 0.24, MeOH) | −7.5° (C = 0.20, MeOH) |
| Infrared absorption (KBr, cm⁻¹) | 1754, 1647, 1598, 1491, 1425, 1376, 1220 | 3402, 1639, 1598, 1483, 1417, 1311, 1261, 1220, 1155 | 1754, 1639, 1598, 1483, 1425, 1376, 1220 | 3361, 1647, 1598, 1483, 1417, 1311, 1261, 1212, 1138 |
| Ultraviolet absorbtion (λmax^EtOH, nm) | Same as in compound 21 | Same as in compound 22 | 226 (ε16000) 249 (ε23000) 256 (ε23000) 267 (ε23000) 324 (ε49000) | 226 (ε16000) 255 (ε24000) 266 (ε24000) 279 (ε22000) 321 (ε55000) |
| Mass spectrum (SIMS, m/z) | 549 [C30H33O8N2]⁺ | 423 [C24H27O5N2]⁺ | 549 [C30H33O8N2]⁺ | 423 [C24H27O5N2]⁺ |
| Proton NMR (DMSO—d6, δ in ppm, CD2HSOCD3 proton chemical shift (δ 2.50) was used as internal standard, Intensity of NMR magnetic field was indicated in each compound) | Same as in compound 21 | Same as in compound 22 | 1.53 (3H,d,J=7Hz) 1.86, 2.18, 2.23 (each 3H,s) 2.87 (3H,s) 3.96 (3H,s) 4.50 (1H,m) 4.98 (1H,t) 5.51 (1H,t) 5.80 (1H,dd, J=3,8Hz) 6.66 (1H,d,J=8Hz, 1'-H) 7.36 (1H,dd,J=2,9Hz) 7.66 (1H,d,J=9Hz) 7.99 (1H,brs) 8.51 (1H,d,J=7.5Hz) 8.62 (1H,d, J=7.5Hz) 10.13 (1H,s) 12.15 (1H,brs) (300MHz) | 1.53 (3H,d,J=7Hz) 2.87 (3H,s) 3.70, 3.98, 4.08, 4.32 (each 1H,m) 3.96 (3H,s) 5.40, 5.47, 5.67 (each 1H,d) 6.24 (1H,dd, J=9Hz,1'-H) 7.35 (1H,dd, J=2,9Hz) 7.66 (1H,d,J=9Hz) 7.98 (1H,d,J=2Hz) 8.53 (1H,d, J=7.5Hz) 8.59 (1H,d,J=7.5Hz) 10.14 (1H,s) (300MHz) |
| Elementary analysis Molecular formula | C30H33N2O8Br | C24H27N2O5Br | C30H33N2O8Br | C24H27N2O5Br |
| Calc. (C, H, N) % | 57.24, 5.28, 4.45 | 57.26, 5.41, 5.57 | 57.24, 5.28, 4.45 | 57.26, 5.41, 5.57 |
| Found (C, H, N) % | 57.28, 5.02, 4.63 | 57.31, 5.27, 5.57 | 57.100, 5.28, 4.49 | 57.15, 5.26, 5.68 |
| Example No. | 27 | 27 | 28 | 28 |

TABLE 1-continued

| R | ![structure OBz,OBz,OBz] | ![structure OBz,OBz,OBz] | ![structure OH,OH,OH] | ![structure OH,OH,OH] |
|---|---|---|---|---|
| X⁻ | Cl⁻ | Cl⁻ | Cl⁻ | Cl⁻ |
| Crystalline form Specific rotatory power [α]_D | Amorphous red powder −90° (C = 0.30, MeOH) | Amorphous red powder +90° (C = 0.35, MeOH) | Amorphous orange powder −130° (C = 0.15, DMSO) | Amorphous orange powder +120° (C = 0.12, DMSO) |
| Infrared absorption (KBr, cm⁻¹) | 1720, 1640, 1590, 1480, 1250 1090, 1060, 1020, 800, 700 | Same as in the left | 3250, 1640, 1595, 1480, 1420, 1380, 1300, 1250, 1220, 1090, 1030, 970, 805 | Same as in the left |
| Ultraviolet absorption (λ_max^EtOH, nm) | 231 (ε58000) 268 (ε30000) 324 (ε60000) | | 208 (ε19000) 226 (ε14000) 256 (ε21000) 266 (ε21000) 279 (ε20000) 320 (ε20000) | |
| Mass spectrum (SIMS, m/z) | 721 | | 409 | |
| Proton NMR (DMSO—d₆, δ in ppm, CD₂HSOCD₃ proton chemical shift (δ 2.50) was used as internal standard, Intensity of NMR magnetic field was indicated in each compound) | [C₄₄H₃₇N₂O₈]⁺ 2.86 (3H,s) 3.94 (3H,s) 4.95 (1H,dd) 5.14 (1H,dd) 5.42 (1H, quintet) 6.10 (2H,brs) 7.03 (1H,s,1'-H) 7.32—8.25 (18H,m) 8.53 (1H,d,J=7.5Hz) 8.76 (1H, 2J=7.5Hz) 10.16 (1H,s) 12.35 (1H,brs) | | [C₂₁H₂₅N₂O₅]⁺ 2.80 (3H,s) 3.25 (3H,s) 3.92 (3H,s) 3.97 (2H,m) 4.16 (1H, brs) 4.34 (1H,s) 4.49 (1H,m) 5.10 (1H,t) 5.73 (1H,brs) 6.38 (1H,brs) 6.33 (1H,s,1'-H) 7.28 (1H,dd,J=2.9Hz) 7.57 (1H,d, J=9Hz) 7.83 (1H,d,J=2Hz) 8.43 (1H,d,J=7.5Hz) 8.62 (1H,d, J=7.5Hz) 10.12 (1H,s) 12.12 (1H,brs) | |
| Elementary analysis Molecular formula Calc. (C, H, N) % Found (C, H, N) % | | | | |

| Example No. | 29 | 29 | 30 | 31 |
|---|---|---|---|---|
| R | ![structure OBz,OBz (D-Ery)] | ![structure OBz,OBz (L-Ery)] | ![structure BzO,OBz,CH₃ (D-5d Rib)] | ![structure BzO,OBz,CH₃ (L-5d Ara)] |
| X⁻ | Cl | Cl | Cl | Cl |
| Crystalline form Specific rotatory power [α]_D | Amorphous orange powder −180° (C = 0.13) | Amorphous orange powder +170° (C = 0.21) | Amorphous orange powder −130° (C = 0.20) | Amorphous orange powder −290° (C = 0.15) |
| Infrared absorption (KBr, cm⁻¹) | 1730, 1600, 1470, 1420, 1280, 1100, 710 | 1730, 1600, 1470, 1420, 1100, 710, 1280 | 1730, 1600, 1470, 1280, 1100, 720 | 1730, 1640, 1600, 1480, 1460, 1420, 1260, 1210, 1100, 1060, |

TABLE 1-continued

| Example No. | 32 | 33 | 35 | 35 | |
|---|---|---|---|---|---|
| R | (structure with two 4-methylphenyl ester groups on tetrahydrofuran with CH2OC(=O)-tolyl) | BnO, OBn, CH3 (L-5d Ara) | BzO, OBz, CH2OBz (D-Xyl) | BzO, OBz, CH2OBz (L-Xyl) | |
| X⁻ | Cl | Cl | Cl | Cl | |
| Crystalline form Specific rotatory power [α]D | Amorphous orange powder −240° (C = 0.2) | Amorphous orange powder +11° (C = 0.30) | Amorphous orange powder −75° (C = 0.19) | Amorphous orange powder +80° (C = 0.14) | |
| Infrared absorption (KBr, cm⁻¹) | 1720, 1610, 1470, 1270, 1180, 1100, 750 | 1760, 1600, 1480, 1420, 1370, 1200, 1090, 920, 820, 740, 700 | 1730, 1600, 1470, 1450, 1420, 1260, 1100, 1070, 1020, 710 | 1730, 1600, 1470, 1450, 1420, 1260, 1100, 1070, 1020, 710 | |
| Ultraviolet absorption ($\lambda_{max}^{EtOH}$, nm) | 243 (ε46000) 284 (ε20000) 314 (ε59000) | 204 (ε34000) 252 (ε24000) 314 (ε69000) | 233 (ε52000) 282 (ε22000) 315 (ε67000) | 233 (ε55000) 276 (ε24000) 284 (ε24000) 316 (ε72000) | |
| Mass spectrum (SIMS, m/z) | 657 | 601 | 749 | 749 | |
| Proton NMR (DMSO-d₆, δ in ppm, CD₂HSOCD₃ proton chemical shift (δ 2.50) was used as internal standard, Intensity of NMR | [C₄₀H₃₇N₂O₇]⁺ 2.19 (3H,s) 2.36 (3H,s) 2.44 (3H,s) 2.86 (3H,s) 3.05 (1H,m) 3.26 (2H,m) 4.75 (1H,d,J=6.5Hz) 4.85 (1H,dd) 4.96 (1H,m) 5.78 (1H,m) 6.98 (1H,t,J=6.5Hz,1'-H) 7.10 (2H,d,J=8Hz) 7.43 (2H,d, J=8Hz) 7.68 (2H,d,J=8Hz) 8.00 | [C₃₈H₃₇N₂O₅]⁺ 1.60 (3H,d,J=6.5Hz) 2.37 (3H, s) 2.88 (3H,s) 3.23 (3H,s) 4.22 (2H,m) 4.50 (2H,m) 4.68 (3H,m) 6.80 (3H,m) 7.00 (3H,m) 7.32–7.44 (4H,m) 7.46 (1H,dd, J=2,9Hz) 7.73 (1H,d,J=9Hz) 8.23 (1H,d,J=2Hz) 8.48 (2H,s) | [C₄₅H₃₇N₂O₉]⁺ 2.37 (3H,s) 2.90 (3H,s) 3.30 (3H,s) 4.95 (1H,dd) 5.14 (1H, dd) 5.43 (1H, quintet) 6.11 (1H,d) 6.14 (1H,s) 7.33–8.25 (18H,m) 8.56 (1H,d,J=7.5Hz) 8.81 (1H,d, | [C₄₅H₃₇N₂O₉]⁺ 2.37 (3H,s) 2.90 (3H,s) 3.30 (3H,s) 4.95 (1H,dd) 5.14 (1H, dd) 5.43 (1H, quintet) 6.11 (1H,d) 6.14 (1H,s) 7.04 (1H,s,1'-H) (1H,d,J=7.5Hz) 8.81 (1H,d, | |

| | | | | | |
|---|---|---|---|---|---|
| Ultraviolet absorption ($\lambda_{max}^{EtOH}$, nm) | 231 (ε36000) 284 (ε21000) 315 (ε63000) | 231 (ε36000) 284 (ε21000) 315 (ε63000) | 231 (ε38000) 285 (ε23000) 315 (ε68000) | 231 (ε42000) 285 (ε22000) 315 (ε66000) | |
| Mass spectrum (SIMS, m/z) | 615 | 615 | 629 | 629 | |
| Proton NMR (DMSO-d₆, δ in ppm, CD₂HSOCD₃ proton chemical shift (δ 2.50) was used as internal standard, Intensity of NMR magnetic field was indicated in each compound | [C₃₇H₃₁N₂O₇]⁺ 2.36 (3H,s) 2.91 (3H,s) 4.60 (1H,dd,J=10.5Hz) 5.21 (1H, J=4.0,10.5Hz) 6.07 (1H,t, J=3.5Hz) 6.27 (1H,dd,J=3,5.4Hz) 7.01 (1H,d,J=6.5Hz,1'-H) 7.24 (1H,m) 7.42 (m) 7.61 (m) 7.75 (m) 7.85 (2H,d) 8.08 (2H,d) 8.23 (1H,d, J=2.5Hz) 8.60 (1H,d,J=7.5Hz) 8.83 (1H,d,J=7.5Hz) 10.28 (1H, s) 12.55 (1H,brs) | [C₃₇H₃₁N₂O₇]⁺ same as in the left | [C₃₈H₃₃N₂O₇]⁺ 1.76 (3H,d,J=6.5Hz) 2.37 (3H, s) 2.93 (3H,s) 4.83 (1H,m) 5.75 (1H,dd) 6.15 (1H,t) 6.94 (1H,d,J=5Hz,1'-H) 7.44–8.03 (12H,m) 8.26 (1H,d,J=2Hz) 8.62 (1H,d,J=7.5Hz) 8.78 (1H,d, J=7.5Hz) 10.27 (1H,s) 12.55 (1H, brs) | [C₃₈H₃₃N₂O₁₁]⁺ 1.68 (3H,d,J=6.5Hz) 2.37 (3H, s) 2.73 (3H,s) 3.30 (3H,s) 5.44 (1H,m) 5.60 (1H,s) 6.13 (1H,m) 7.14 (1H,s,1'-H) 7.19–8.17 (12H,m) 8.24 (1H,d J=2Hz) 8.24 (1H,d,J=2Hz) 8.62 (1H,d,J=7.5Hz) 8.75 (1H,d, J=7.5Hz) 10.07 (1H,s) 12.45 (1H,brs) | |
| Elementary analysis Molecular formula Calc. (C, H, N) % Found (C, H, N) % | — | — | — | — | |

TABLE 1-continued

| | | | | |
|---|---|---|---|---|
| magnetic field was indicated in each compound | (2H,d,J=8Hz) 7.47 (1H,dd, J=2.9Hz) 7.73 (1H,d,J=9Hz) 8.25 (1H,d,J=2Hz) 8.46 (1H,d, J=7.5Hz) 8.59 (1H,d,J=7.5Hz) 10.08 (1H,s) 12.39 (1H,brs) | 10.03 (1H,s) 12.51 (1H,brs) | J=7.5Hz) 10.20 (1H,s) 12.58 (1H,brs) | J=7.5Hz) 10.20 (1H,s) 12.58 (1H,brs) |
| Elementary analysis Molecular formula | | | $C_{45}H_{37}N_2O_9Cl.3H_2O$ | $C_{45}H_{37}N_2O_9Cl.3H_2O$ |
| Calc. (C, H, N) % | | | 64.40, 5.16, 3.34 | 64.40, 5.16, 3.34 |
| Found (C, H, N) % | | | 64.38, 4.92, 3.53 | 64.69, 4.90, 3.62 |
| Example No. | 35 | 36 | 37 | 38 |

| | | | | |
|---|---|---|---|---|
| R | BzO, OBz, CH₂OBz (D-Ara) | BzO, OBz, CH₂OBz (L-Ara) | BzO, OBz, CH₂OBz (L-Rib) | BzO, OBz, CH₂OBz (D-Xyl) |
| X⁻ | Br | Br | Br | Br |
| Crystalline form | Amorphous red powder | Amorphous orange powder | Amorphous orange powder | Amorphous orange powder |
| Specific rotatory power [α]D | +180° (C = 0.11) | −190° (C = 0.11) | +200° (C = 0.22) | −86° (C = 0.10) |
| Infrared absorption (KBr, cm⁻¹) | 1730, 1600, 1480, 1460, 1420, 1280, 1210, 1100, 1080, 1030, 720 | 1730, 1600, 1480, 1460, 1420, 1280, 1210, 1100, 1080, 1030, 720 | 1720, 1640, 1590, 1440, 1260, 1100, 700 | 1720, 1600, 1470, 1450, 1420, 1260, 1200, 1100, 1060, 1020, 710 |
| Ultraviolet absorption ($\lambda_{max}^{EtOH}$, nm) | 233 (ε54000) 276 (ε23000) 284 (ε23000) 316 (ε70000) | 232 (ε52000) 281 (ε23000) 315 (ε67000) | 231 (ε50000) 276 (ε23000) 284 (ε23000) 316 (ε67000) | 233 (ε56000) 276 (ε23000) 284 (ε23000) 316 (ε71000) |
| Mass spectrum (SIMS, m/z) | 749 | 749 | 749 | 749 |
| | $[C_{45}H_{37}N_2O_9]^+$ | $[C_{45}H_{37}N_2O_9]^+$ | $[C_{45}H_{37}N_2O_9]^+$ | $[C_{45}H_{37}N_2O_9]^+$ |
| Proton NMR (DMSO-d₆, δ in ppm, CD₂HSOOCD₃ proton 2.50) was used as internal standard. Intensity of NMR magnetic field was indicated in each compound | 2.36 (3H,s) 2.94 (3H,s) 4.86 (2H,m) 5.74 (1H,m) 6.02 (1H,t) 6.24 (1H,t) 7.20 (1H,d,J=1.5Hz,1'-H) 7.30–8.15 (17H, m) 8.26 (1H,d,J=2Hz) 8.63 (1H, d,J=7.5Hz) 8.84 (1H,d,J=7.5Hz) 10.16 (1H,s) 12.44 (1H,brs) | Same as in the left | 2.36 (3H,s) 2.90 (3H,s) 3.26 (3H,s) 4.97 (2H,t) 5.18 (1H,q) 6.12 (1H,t) 6.20 (1H,t) 7.04 (1H,d,J=5Hz,1'-H) 7.44–8.05 (17H,m) 8.23 (1H,d,J=2Hz) 8.54 (1H,d,J=7.5Hz) 8.76 (1H,d, J=7.54Hz) 10.25 (1H,s) 12.43 (1H,brs) | 2.37 (3H,s) 2.91 (3H,s) 4.95 (1H,dd) 5.13 (1H,dd) 5.42 (1H, quintet) 6.10 (1H,d) 6.13 (1H,s) 7.02 (1H,s,1'-H) 7.33–8.25 (18H,m) 8.57 (1H,d,J=7.5Hz) 8.81 (1H,d,J=7.5Hz) 10.18 (1H, s) 12.50 (1H,brs) |
| Elementary analysis Molecular formula Calc. (C, H, N) % Found (C, H, N) % | — | — | — | — |
| Example No. | 39 | 40 | 41 | |

TABLE 1-continued

| R | ![structure](BnO, OBn, CH₂OBn furanose) | ![structure](BnO, OBn, CH₂OBn furanose) | ![structure](AcO, OAc, OAc pyranose) | ![structure](AcO, OAc, OAc pyranose) |
|---|---|---|---|---|
| | (D-Ara) | (L-Ara) | (D-Xyl) | (L-Xyl) |
| X− | Br | Br | Br | Br |
| Crystalline form | Amorphous orange powder | Amorphous orange powder | Amorphous red powder | Amorphous red powder |
| Specific rotatory power $[\alpha]_D$ | +38° (C = 0.16) | −40° (C = 0.24) | −87° (C = 0.15) | +71° (C = 0.09) |
| Infrared absorption (KBr, cm$^{-1}$) | 1760, 1600, 1470, 1410, 1360, 1200, 1190, 910, 730, 690 | 1760, 1600, 1470, 1410, 1360, 1200, 1190, 910, 730, 690 | 1760, 1600, 1470, 1420, 1380, 1220, 1060, 810 | 1220, 1060, 810 |
| Ultraviolet absorption ($\lambda_{max}^{EtOH}$, nm) | 252 (ε25000) 315 (ε71000) | 252 (ε25000) 315 (ε71000) | 246 (ε25000) 252 (ε25000) 285 (ε21000) 316 (ε66000) | 250 (ε18000) 286 (ε15000) 316 (ε46000) |
| Mass spectrum (SIMS, m/z) | 707 [C₄₅H₄₃N₂O₆]⁺ | 707 [C₄₅H₄₃N₂O₆]⁺ same as in the left | 563 [C₃₀H₃₁N₂O₉]⁺ | 563 [C₃₀H₃₁N₂O₉]⁺ Same as in the left (1′,2′-Trans form) |
| Proton NMR (DMSO−d₆, δ in ppm, CD₂HSOCD₃ proton chemical shift (δ 2.50) was used as internal standard, Intensity of NMR magnetic field was indicated in each compound) | 2.37 (3H,s) 2.85 (3H,s) 3.21 (3H,s) 3.90 (2H,m) 4.34-4.80 (10H,m) 6.85 (3H,m) 7.03 (3H,m) 7.32-7.44 (9H,m) 7.47 (1H, dd,J=2.9Hz) 7.73 (1H,d,J=9Hz) 8.23 (1H,d,J=2H) 8.25 (1H,d, J=7.5Hz) 8.61 (1H,d,J=7.5Hz) 10.06 (1H,s) 12.36 (1H,brs) | | 1.78, 2.04, 2.08 (each 3H,s) 2.36 (3H,s) 2.89 (3H,s) 3.88 (1H,m) 4.37 (1H,m) 5.52 (2H,m) 5.92 (1H,t) 6.31 (1H,d,J=9Hz,1′-H) 7.48 (1H,dd,J=2.9Hz) 7.74 (1H,d,J=9Hz) 8.29 (1H,d, J=2Hz) 8.56 (1H,d,J=7.5Hz) 8.72 (1H,d,J=7.5Hz) 10.23 (1H,s) 12.55 (1H,brs) ¹H−NMR exhibits the value of 1′, 2′-trans form. | |
| Elementary analysis Molecular formula· Calc. (C, H, N) % Found (C, H, N)% | C₄₅H₄₃N₂O₆Br·½H₂O 67.83, 5.57, 3.52 67.71, 5.63, 3.24 | C₄₅H₄₃N₂O₆Br·½H₂O 67.83, 5.57, 3.52 67.90, 5.50, 3.51 | | |
| Example No. | 42 | 42 | 43 | 43 |

| R | ![structure](AcO, OAc, OAc pyranose) | ![structure](AcO, OAc, OAc pyranose) | ![structure](AcO, OAc, OAc pyranose) | ![structure](AcO, OAc, OAc pyranose) |
|---|---|---|---|---|
| | (D-Ara) | (L-Ara) | (D-Rib) | (L-Rib) |
| X− | Br | Br | Br | Br |
| Crystalline form | Amorphous red powder | Amorphous red powder | Amorphous orange powder | Amorphous orange powder |
| Specific rotatory power $[\alpha]_D$ | −48° (C = 0.16) | +39° (C = 0.20) | +7.0° (C = 0.20) | −9.2° (C = 0.12) |
| Infrared absorption (KBr, cm$^{-1}$) | 1750, 1640, 1600, 1480, 1420, 1370, 1220, 1060, 940, 810 | 1750, 1640, 1600, 1480, 1420, 1370, 1220, 1060, 940, 810 | 1760, 1640, 1600, 1480, 1420, 1380, 1220, 1100, 1040, 920, 810 | 1760, 1640, 1600, 1480, 1420, 1380, 1220, 1100, 1040, 920, |

TABLE 1-continued

| | | | | |
|---|---|---|---|---|
| Ultraviolet absorption ($\lambda_{max}^{EtOH}$, nm) | 247 (ε15000) 285 (ε13000) 316 (ε39000) | 253 (ε22000) 386 (ε19000) 317 (ε57000) | 253 (ε22000) 285 (ε19000) 316 (ε57000) | 820 250 (ε35000) 285 (ε29000) 316 (ε81000) | 820 246 (ε26000) 253 (ε26000) 285 (ε22000) 316 (ε68000) |
| Mass spectrum (SIMS, m/z) | 563 | 563 | | 563 | 563 |
| | [C$_{30}$H$_{31}$N$_2$O$_9$]$^+$ | [C$_{30}$H$_{31}$N$_2$O$_9$]$^+$ | | [C$_{30}$H$_{31}$N$_2$O$_9$]$^+$ | [C$_{30}$H$_{31}$N$_2$O$_9$]$^+$ |
| Proton NMR (DMSO-d$_6$, δ in ppm, CD$_2$HSOCD$_3$ proton chemical shift (δ 2.50) was used as internal standard, Intensity of NMR magnetic field was indicated in each compound) | 1.80, 2.00, 2.27 (each 3H,s) 2.37 (3H,s) 2.89 (3H,s) 3.35 (3H,s) 4.33 (2H,s) 5.43 (1H,s) 5.51 (2H,portion AB in ABX, J$_{2',3'}$=10Hz,J$_{1',3'}$=4Hz) 6.35 (1H, portion X in ABX, J$_{1',2'}$=8Hz,1'-H) 7.48 (1H,dd, J=2,9Hz) 7.74 (1H,d,J=2Hz) 8.29 (1H,d,J=9Hz) 8.57 (2H, AB quartet) 10.16 (1H,s) 12.48 (1H,brs) | Same as in the left | | 1.76, 2.06, 2.31 (each 3H,s) 2.37 (3H,s) 2.90 (3H,s) 3.32 (3H,s) 4.07 (1H,t) 4.26 (1H,q) 5.54 (1H,m) 5.79 (1H,t) 5.93 (1H,dd) 6.47 (1H,d,J=9Hz,1'-H) 7.47 (1H,dd,J=2,9Hx) 7.74 (1H, d,J=9Hz) 8.28 (1H,d,J=2Hz) 8.58 (1H,d,J=7.5Hz) 8.78 (1H, d,J=7.5Hz) 10.28 (1H,s) 12.50 (1H,brs) | Same as in the left |
| Elementary analysis Molecular formula Calc. (C, H, N) % Found (C, H, N) % | — | — | | C$_{30}$H$_{31}$N$_2$O$_9$Br·2.5H$_2$O 52.33, 5.27, 4.07 52.36, 5.15, 4.00 | C$_{30}$H$_{31}$N$_2$O$_9$Br·2.5H$_2$O 52.33, 5.27, 4.07 52.27, 5.03, 4.17 |
| Example No. | 44 | 44 | | 45 | 45 |

| | | | |
|---|---|---|---|
| R | (D-Lyx) structure with AcO, OAc, IIIOAc | (L-Lyx) structure with AcO, IIIOAc, OAc | (D-Man) structure with AcO, OAc, OAc, CH$_2$OAc | (L-Man) structure with AcO, OAc, OAc, CH$_2$OAc |
| X$^-$ | Cl | Cl | Br | Br |
| Crystalline form Specific rotatory power [α]$_D$ | Amorphous orange powder −110° (C = 0.13) | Amorphous orange powder +100° (C = 0.30) | Amorphous red powder +24° (C = 0.16) | Amorphous red powder −24° (C = 0.11) |
| Infrared absorption (KBr, cm$^{-1}$) | 1760, 1640, 1600, 1480, 1420, 1380, 1220, 1060, 920, 820 | 1760, 1640, 1600, 1480, 1420, 1380, 1220, 1060, 920, 820 | 1740, 1640, 1600, 1480, 1420, 1370, 1220, 1120, 1050, 820 | 1740, 1640, 1600, 1480, 1420, 1370, 1220, 1120, 1050, 820, |
| Ultraviolet absorption ($\lambda_{max}^{EtOH}$, nm) | 209 (ε19000) 251 (ε22000) 285 (ε19000) 316 (ε57000) | 209 (ε19000) 253 (ε23000) 286 (ε20000) 316 (ε62000) | 252 (ε23000) 286 (ε20000) 316 (ε62000) | 246 (ε24000) 252 (ε22000) 286 (ε21000) 316 (ε61000) |
| Mass spectrum (SIMS, m/z) | 563 [C$_{30}$H$_{31}$N$_2$O$_9$]$^+$ | 563 [C$_{30}$H$_{31}$N$_2$O$_9$]$^+$ Same as in the left | 635 [C$_{33}$H$_{35}$N$_2$O$_{11}$]$^+$ | 635 [C$_{33}$H$_{35}$N$_2$O$_{11}$]$^+$ Same as in the left |
| Proton NMR (DMSO-d$_6$, δ in ppm, CD$_2$HSOCD$_3$ proton chemical shift (δ 2.50) was used as internal standard | 1.77, 2.27, 2.29 (each 3H,s) 2.37 (3H,s) 2.91 (3H,s) 3.37 (3H,s) 4.26, 4.33, (each 1H, AB quartet,J=13Hz) 5.05 (1H,d) 5.55 (2H,m) 6.56 (1H,d,J=9Hz, 1'-H) | | 1.86, 2.05, 2.20, 2.24 (each 3H,s) 2.37 (3H,s) 2.92 (3H,s) 3.38 (3H,s) 4.48 (1H,dd) 4.64 (2H,m) 5.18 (1H,t) 5.55 (1H,t) 5.83 (1H,dd) 6.74 (1H,d,J=8.5Hz,1'-H) | |

TABLE 1-continued

| | Example No. | 46 | 46 | 47 | 47 |
|---|---|---|---|---|---|
| R | | (D-All) | (L-All) | (D-Tal) | (L-Tal) |
| X— | | Br | Br | Br | Br |
| Crystalline form Specific rotatory power $[\alpha]_D$ | | Amorphous orange powder $-22°$ (C = 0.26) | Amorphous orange powder $+20°$ (C = 0.19) | Amorphous orange powder $+100°$ (C = 0.22) | Amorphous orange powder $-95°$ (C = 0.31) |
| Infrared absorption (KBr, cm$^{-1}$) | | 1760, 1640, 1600, 1480, 1420, 1370, 1220, 1040, 910, 820 | 1760, 1640, 1600, 1480, 1420, 1370, 1220, 1040, 910, 820 | 1750, 1640, 1600, 1480, 1380, 1220, 1100, 1040, 920, 820 | 1750, 1640, 1600, 1480, 1380, 1220, 1100, 1040, 920, 820 |
| Ultraviolet absorption ($\lambda_{max}^{EtOH}$, nm) | | 206 ($\epsilon$20000) 246 ($\epsilon$25000) 252 ($\epsilon$25000) 286 ($\epsilon$21000) 316 ($\epsilon$66000) | 206 ($\epsilon$20000) 246 ($\epsilon$25000) 252 ($\epsilon$25000) 286 ($\epsilon$21000) 316 ($\epsilon$66000) | 246 ($\epsilon$28000) 252 ($\epsilon$27000) 286 ($\epsilon$23000) 316 ($\epsilon$74000) | 246 ($\epsilon$28000) 252 ($\epsilon$27000) 286 ($\epsilon$23000) 316 ($\epsilon$74000) |
| Mass spectrum (SIMS, m/z) | | 635 [C$_{33}$H$_{35}$N$_2$O$_{11}$]+ | 635 [C$_{33}$H$_{35}$N$_2$O$_{11}$]+ | 635 [C$_{33}$H$_{35}$N$_2$O$_{11}$]+ | 635 [C$_{33}$H$_{35}$N$_2$O$_{11}$]+ |
| Proton NMR (DMSO-d$_6$, $\delta$ in ppm, CD$_2$HSOCD$_3$ proton chemical shift ($\delta$ 2.50) was used as internal standard, Intensity of NMR magnetic field was indicated in each compound) | | 1.79, 2.06, 2.08, 2.30 (each 3H,s) 2.37 (3H,s) 2.90 (3H,s) 3.35 (3H,s) 4.23 (1H,dd) 4.41 (1H,dd) 4.51 (1H,m) 5.45 (1H, dd) 5.80 (1H,t) 5.93 (1H,dd) 6.59 (1H,d,J=9.5Hz,1'-H) 7.47 (1H,dd,J=2.9Hz) 7.72 (1H,d, J=9Hz) 8.27 (1H,d,J=2Hz) 8.57 (1H,d,J=7.5Hz) 8.77 (1H,d, J=7.5Hz) 10.26 (1H,s) 12.48 (1H,brs) | Same as in the left | 1.77, 2.02, 2.11, 2.29 (each 3H,s) 2.37 (3H,s) 2.90 (3H,s) 3.37 (3H,s) 4.47 (1H,d) 4.70 (1H,t) 4.88 (1H,dd) 5.74 (2H,m) 5.91 (1H,dd) 6.69 (1H,d,J=9Hz,1'-H) 7.47 (1H,dd,J=2, 9Hz) 7.72 (1H,d,J=9Hz) 8.28 (1H,d,J=2Hz) 8.62 (1H,d, J=7.5Hz) 8.82 (1H,d,J=7.5Hz) 10.29 (1H,s) 12.48 (1H,brs) | Same as in the left |
| Elementary analysis Molecular formula Calc. (C, H, N) % Found (C, H, N) % | | — | — | — | — |
| Example No. | | 48 | 49 | 50 | 51 |

| | Intensity of NMR magnetic field was indicated in each compound) | Elementary analysis Molecular formula Calc. (C, H, N) % Found (C, H, N) % |
|---|---|---|
| | 7.48 (1H,dd,J=2.9Hz) 7.74 (1H,d,J=9Hz) 8.28 (1H,d, J=2Hz) 8.54 (1H,d,J=7.5Hz) 8.66 (1H,d,J=7.5Hz) 10.27 (1H,s) 12.55 (1H,brs) | — |
| | 7.47 (1H,dd, J=2,9Hz) 7.74 (1H,d,J=9Hz) 8.29 (1H,d,J=2Hz) 8.57 (1H,d, J=7.5Hz) 8.66 (1H,d,J=7.5Hz) 10.15 (1H,s) 12.42 (1H,brs) | — |

TABLE 1-continued

| R | (L-Gal) | (L-Glc) | (D-Glc NAc) | (D-Gal NAc) |
|---|---|---|---|---|
| X⁻ | Br | Br | Cl | Cl |
| Crystalline form Specific rotatory power [α]$_D$ | Amorphous orange powder +3.7° (C = 0.30) | Amorphous red powder +75° (C = 0.19) | Amorphous orange powder −110° (C = 0.19) | Amorphous orange powder −41° (C = 0.19) |
| Infrared absorption (KBr, cm$^{-1}$) | 1760, 1640, 1600, 1480, 1420, 1380, 1220, 1060, 940 | 1760, 1640, 1600, 1480, 1420, 1390, 1220, 1040 | 1760, 1600, 1480, 1420, 1370, 1220, 1050, 940, 920, 820 | 1750, 1660, 1600, 1470, 1420, 1370, 1220, 910, 810 |
| Ultraviolet absorption ($\lambda_{max}^{EtOH}$, nm) | 246 (ε27000) 253 (ε26000) 286 (ε23000) 318 (ε67000) | 246 (ε25000) 253 (ε21000) 286 (ε21000) 317 (ε66000) | 207 (ε18000) 253 (ε23000) 286 (ε20000) 317 (ε63000) | 208 (ε18000) 253 (ε24000) 285 (ε20000) 317 (ε65000) |
| Mass spectrum (SIMS, m/z) | 635 | 635 | 634 | 634 |
| Proton NMR (DMSO-d$_6$, δ in ppm, CD$_2$HSOCD$_3$ proton chemical shift (δ 2.50) was used as internal standard, Intensity of NMR magnetic field was indicated in each compound) | [C$_{33}$H$_{35}$N$_2$O$_{11}$]+ 1.80, 1.99, 2.01, 2.28 (each 3H,s) 2.37 (3H,s) 2.90 (3H,s) 3.35 (3H,s) 4.25 (2H,m) 4.76 (1H,m) 5.54 (3H,m) 6.46 (1H,d,J=9Hz,1'-H) 7.47 (1H,dd,J=1.5, 9Hz) 7.72 (1H,dd,1.5,9Hz) 8.27 (1H,t,1.5Hz) 8.57 (2H,s) 10.16 (1H,s) 12.55 (1H,brs) | [C$_{33}$H$_{35}$N$_2$O$_{11}$]+ 1.79, 2.02, 2.06, 2.09 (each 3H,s) 2.37 (3H,s) 2.89 (3H,s) 3.37 (3H,s) 4.26 (2H,m) 4.44 (1H,m) 5.58 (2H,m) 5.95 (1H,t) 6.41 (1H,d,J=9Hz,1'-H) 7.48 (1H,dd,J=2,9Hz) 7.74 (1H,d, J=9Hz) 8.28 (1H,d,J=2Hz) 8.55 (1H,d,J=7.5Hz) 8.74 (1H,d, J=7.5Hz) 10.23 (1H,s) 12.52 (1H,brs) | [C$_{33}$H$_{36}$N$_3$O$_{10}$]+ 1.50 (3H,s) 1.98, 2.06, 2.08 (each 3H,s) 2.37 (3H,s) 2.87 (3H,s) 3.34 (3H,s) 4.28 (2H,m) 4.33 (1H,m) 4.93 (1H,q, J=9.5Hz) 5.35 (1H,t,J=9.5Hz) 5.44 (1H,t,J=9.5Hz) 6.26 (1H,d,J=9.5Hz,1'-H) 7.46 (1H,dd, J=2,9Hz) 7.73 (1H,d,J=9Hz) 8.26 (1H,d,J=2Hz) 8.42 (1H,d, J=9.5Hz) 8.53 (1H,d,J=7.5Hz) 8.64 (1H,d,J=7.5Hz) 10.14 (1H, s) 12.55 (1H,brs) | [C$_{33}$H$_{36}$N$_3$O$_{10}$]+ 1.50 (3H,s) 1.96, 2.02, 2.27 (each 3H,s) 2.37 (3H,s) 2.89 (3H,s) 4.25 (2H,m) 4.54 (1H,m) 4.65 (1H,t) 5.33 (1H,dd) 5.54 (1H,d) 6.23 (1H,d,J=9.5Hz 1'-H) 7.47 (1H,dd,J=2,9Hz) 7.74 (1H,d,J=9Hz) 8.27 (1H,d, J=2Hz) 8.44 (1H,d,J=8Hz) 8.50 (1H,d,J=7.5Hz) 8.55 (1H,d, J=7.5Hz) 10.04 (1H,s) 12.45 (1H,brs) |
| Elementary analysis Molecular formula Calc. (C, H, N) % Found (C, H, N) % | — | — | — | — |

| Example No. | 52 | 53 | 54 | 54 |
|---|---|---|---|---|
| R | (D-Glc UA) | | | |
| X⁻ | Br | | Cl⁻ | Cl⁻ |

TABLE 1-continued

| | Example No. 55 | Example No. 56 | Example No. 57 | Example No. 58 |
|---|---|---|---|---|
| Crystalline form Specific rotatory power [α]D | Amorphous red powder −79° (C = 0.09) | Amorphous red powder +59° (C = 0.11,EtOH) | Amorphous red powder −120° (C = 0.13,MeOH) | Amorphous red powder +120° (C = 0.15, CH3OH) |
| Infrared absorption (KBr, cm$^{-1}$) | 1760, 1640, 1600, 1480, 1420, 1370, 1220, 1040 | 1760, 1750, 1640, 1590, 1475, 1425, 1380, 1370, 1220 | 3350, 3150, 1750, 1640, 1595, 1585, 1470, 1450, 1425, 1260, 1090, 810, 700 | Same as in the left |
| Ultraviolet absorption ($\lambda_{max}^{EtOH}$, nm) | 206 (ε21000) 246 (ε25000) 286 (ε21000) 318 (ε64000) | 226 (ε15000) 251 (ε22000) 269 (ε23000) 326 (ε45000) | 231 (ε50000) 271 (ε27000) 326 (ε48000) | |
| Mass spectrum (SIMS, m/z) | 621 | 535 | 707 | |
| Proton NMR (DMSO-d6, δ in ppm, CD3HSOCD3 proton chemical shift (δ 2.50) was used as internal standard, Intensity of NMR magnetic field was indicated in each compound) | [C32H33N2O11]+ 1.79, 2.04, 2.09 (each 3H,s) 2.37 (3H,s) 2.88 (3H,s) 3.70 (3H,s) 4.90 (1H,d,J=9.5Hz) 5.66 (1H,t,J=9.5Hz) 5.71 (1H, t,J=9.5Hz) 6.06 (1H,t,J=9.5Hz) 6.47 (1H,d,J=9.5Hz,1'-H) 7.47 (1H,dd,J=2,9Hz) 7.74 (1H,d, J=9Hz) 8.27 (1H,d,J=2Hz) 8.54 (1H,d,J=7.5Hz) 8.78 (1H,d, J=7.5Hz) 10.26 (1H,s) 12.55 (1H,brs) | [C29H31N2O8]+ 1.85, 2.20, 2.25 (each 3H,s) 2.86 (3H,s) 3.35 (3H,s) 4.52 (1H,m) 4.98 (1H,t,J=9.5Hz) 5.50 (1H,t) 5.77 (1H, dd,J=3,8.5Hz) 6.67 (1H,d, J=8.5Hz,1'-H) 7.20 (1H,dd, J=2.9Hz) 7.56 (1H,d,J=9Hz) 7.87 (1H,d,J=2Hz) 8.48 (1H,d, J=7.5Hz) 8.60 (1H,d,J=7.5Hz) 9.50 (1H,s) 10.12 (1H,s) 12.23 (1H,brs) (360MHz) | [C45H35N2O8]+ 2.85 (3H,s) 3.27 (3H,s) 4.96 (1H,dd) 5.12 (1H,dd) 5.40 (1H, quintet) 6.10 (2H,brs) 7.01 (1H,s,1'-H) 7.20 (1H,dd,J=2, 9Hz) 7.33-8.24 (17H,m) 8.51 (1H,d,J=7.5Hz) 8.75 (1H,d, J=7.5Hz) 9.54 (1H,s) 10.10 (1H,s) 12.23 (1H,brs) | |
| Elementary analysis Molecular formula Calc. (C, H, N) % Found (C, H, N) % | — | C29H31N2O8Br 56.59, 5.08, 4.55 56.41, 5.29, 4.37 | — | — |

| Example No. | 55 | 56 | 57 | 58 |
|---|---|---|---|---|
| R | (structure with OBz, OBz, OBz groups) | (structure with BzO, OBz, OBz groups) | (structure with AcO, OAc, OAc groups) | (structure with AcO, OAc, OAc groups) |
| X− | Br− | Br− | Br− | Br− |
| Crystalline form Specific rotatory power [α]D | Amorphous red powder −99° (C = 0.15, MeOH) | Amorphous red powder −170° (C = 0.23, EtOH) | Amorphous red powder −63° (C = 0.073, EtOH) | Amorphous red powder +13° (C = 0.10, MeOH) |
| Infrared absorption (KBr, cm$^{-1}$) | 3400, 3100, 1725, 1640, 1600, 1590, 1475, 1450, 1430, 1250 | 3400, 3100, 1725, 1640, 1595, 1585, 1470, 1450, 1420, 1260 | 3350, 3100, 1750, 1640, 1585, 1470, 1425, 1365, 1215 | 3435, 3238, 1745, 1655, 1598, 1483, 1434, 1376, 1229 |
| Ultraviolet absorption ($\lambda_{max}^{EtOH}$, nm) | 231 (ε51000) 271 (ε27000) 328 (ε48000) | 231 (ε46000) 271 (ε20000) 327 (ε46000) | 249 (ε26000) 255 (ε26000) 261 (ε26000) 270 (ε26000) 328 (ε47000) | 226 (ε14000) 250 (ε21000) 271 (ε22000) 328 (ε42000) |
| Mass spectrum (SIMS, m/z) | 707 | 707 | 593 | 593 |
| Proton NMR | [C45H35N2O8]+ 2.82 (3H,s) 3.14 (3H,s) 4.64 | [C45H35N2O8]+ 2.85 (3H,s) 3.20 (3H,s) 4.97 | [C31H33O10N2]+ 1.80, 2.00, 2.05, 2.10 (each | [C31H33O10N2]+ 1.81, 1.99, 2.02, 2.30 (each |

TABLE 1-continued

| | Example No. | 59 | 60 | 61 | 62 |
|---|---|---|---|---|---|
| R | | ![structure with OBz groups] | ![structure with AcO groups] | ![structure with AcO/OAc groups] | ![structure with OH groups] |
| X⁻ | | Br⁻ | Br⁻ | Br⁻ | Br⁻ |
| Crystalline form | | Amorphous red powder | Amorphous red powder | Amorphous red powder | Amorphous red powder |
| Specific rotatory power [α]$_D$ | | +95° (C = 0.18, MeOH) | +17° (C = 0.15, MeOH) | −21° (C = 0.21 MeOH) | −290° (C = 0.16 1% CF$_3$COOH/H$_2$O) |
| Infrared absorption (KBr, cm⁻¹) | | 3400, 3100, 1725, 1640, 1600, 1590, 1475, 1450, 1430, 1250 | 3427, 3189, 1754, 1639, 1598, 1483, 1434, 1393, 1229 | 3427, 3189, 1754, 1639, 1598, 1483, 1434, 1393, 1229 | 3370, 1647, 1606, 1483, 1425, 1229, 1204, 1097 |
| Ultraviolet absorption ($\lambda_{max}^{EtOH}$, nm) | | Same as in compound 55 | 226 (ε15000) 251 (ε19000) 269 (ε25000) 327 (ε47000) | Same as in the left | 208 (ε19000) 227 (ε13000) 267 (ε22000) 280 (ε19000) 324 (ε42000) |
| Mass spectrum (SIMS, m/z) | | 707 [C$_{43}$H$_{35}$O$_8$N$_2$]⁺ | 535 [C$_{29}$H$_{31}$O$_8$N$_2$]⁺ | 535 [C$_{29}$H$_{31}$O$_8$N$_2$]⁺ | 425 [C$_{23}$H$_{25}$O$_6$N$_2$]⁺ |
| Proton NMR (DMSO-d$_6$, δ in ppm, CD$_2$HSOCD$_3$ proton chemical shift (δ 2.50) was used as internal standard, Intensity of NMR magnetic field was indicated in each compound) | | Same as in compound 55 (2H,m) 6.04 (3H,m) 6.74 (1H,d, J=8.5Hz,1'-H) 7.01 (1H,dd,J=2, 9Hz) 8.53 (1H,d,J=7.5Hz) 8.35 (1H,d,J=7.5Hz) 9.51 (1H,s) 10.23 (1H,s) 12.19 (1H,brs) (360MHz) | 1.26 (3H,d,J=6.5Hz) 1.81, 2.00, 2.32 (each 3H,s) 2.86 (3H,s) 3.35 (3H,s) 4.55 (1H,q) 5.38 (1H,d) 5.50 (1H,m) 6.38 (1H,dd, J=8Hz,1'-H) 7.21 (1H,dd, J=2,9Hz) 7.57 (1H,d,J=9Hz) 7.87 (1H,d,J=2Hz) 8.50 (2H,s) 9.52 (1H,s) 10.08 (1H,s) 12.20 (1H,brs) (300MHz) | (2H,m) 5.16 (1H,m) 6.11 (1H,t) 6.17 (1H,t) 7.01 (1H,d,J=5Hz) 7.18 (1H,dd,J=2,9Hz) 7.45–7.74 and 7.92–8.07 (15H, m) 8.48 (1H,d,J=7.5Hz) 7.80 81H,dd,J=2Hz) 8.70 (1H, d,J=7.5Hz) 9.46 (1H,s) 10.17 (1H,s) 12.14 (1H,s) (360MHz) | 2.85 (3H,s) 3.34 (3H,s) 4.85 (1H,t) 4.96, 5.25, 5.61 (each 1H,d) 5.82 (1H,dd,J=8.5Hz,1'-H) 7.20 (1H,dd,J=2.9Hz) 7.56 (1H, d,J=9Hz) 7.87 (1H,d,J=2Hz) 8.53 (2H,s) 9.48 (1H,s) 10.07 (1H,s) (300MHz) |
| | | (2H,m) 6.04 (3H,m) 6.74 (1H,d, J=8.5Hz,1'-H) 7.01 (1H,dd,J=2, 9Hz) 8.53 (1H,d,J=7.5Hz) 8.35 (1H,d,J=7.5Hz) 9.51 (1H,s) 10.23 (1H,s) 12.19 (1H,brs) (360MHz) | | (2H,m) 5.93 (1H,t) 6.38 (1H,d, J=9Hz,1'-H) 7.20 (1H,dd,J=2, 9Hz) 7.56 (1H,d,J=9Hz) 7.87 (1H,d,J=2Hz) 8.48 (1H, d,J=7.5Hz) 8.67 (1H,d,J=7.5Hz) 9.48 (1H,s) 10.15 (1H,s) 12.20(1H,brs) (360MHz) | 3H,s) 2.85 (3H,s) 3.27 (3H,s) 4.24 (2H,m) 4.74 (1H,m) 5.54 (3H,m) 6.42 (1H, d,J=8.5Hz,1'-H) 7.20 (1H,dd, J=2,9Hz) 7.56 (1H,d,J=9Hz) 7.87 (1H,d,J=2Hz) 8.51 (2H,s) 9.50 (1H,s) 10.06 (1H,s) 12.23 (1H,brs) (360MHz) |
| Elementary analysis Molecular formula | | C$_{43}$H$_{35}$N$_2$O$_8$Br | C$_{43}$H$_{35}$N$_2$O$_8$Br C$_{29}$H$_{31}$N$_2$O$_8$Br | C$_{43}$H$_{35}$N$_2$O$_8$Br C$_{29}$H$_{31}$N$_2$O$_8$Br | C$_{31}$H$_{33}$N$_2$O$_{10}$Br C$_{31}$H$_{33}$N$_2$O$_{10}$Br C$_{23}$H$_{25}$N$_2$O$_6$Br |
| Calc. (C, H, N) % | | 65.57, 4.48, 3.56 | 65.57, 4.48, 3.56 / 56.59, 5.08, 4.55 | 65.57, 4.48, 3.56 / 56.59, 5.08, 4.55 | 55.28, 4.79, 4.16 / 55.28, 4.79, 4.16 / 54.66, 5.00, 5.54 |
| Found (C, H, N) % | | 65.60, 4.42, 3.31 | 65.37, 4.65, 3.41 / 56.71, 4.98, 4.32 | 65.32, 4.59, 3.60 / 56.72, 5.15, 4.32 | 55.15, 5.12, 4.26 / 55.25, 4.91, 4.32 / 54.41, 5.05, 5.73 |

TABLE 1-continued

| Example No. | 63 | 64 | 65 | 66 |
|---|---|---|---|---|
| R | (L-Ara) | (D-Ara) | (D-Man) | (L-Man) |
| X⁻ | Br⁻ | Br⁻ | Br⁻ | Br⁻ |
| Crystalline form | Amorphous orange powder | Amorphous red powder | Amorphous red powder | Amorphous red powder |
| Specific rotatory power $[\alpha]_D$ | −38° (C = 0.11) | +52° (C = 0.22) | +300° C. (C = 0.27) | −300° (C = 0.24) |
| Infrared absorption (KBr, cm⁻¹) | 3200, 1640, 1590, 1460, 1420, 1210, 1050, 800 | 3200, 1640, 1590, 1460, 1420, 1210, 1050, 800 | 3200, 1640, 1600, 1470, 1420, 1220, 1200, 1100, 1040, 800 | 3200, 1640, 1600, 1470, 1420, 1220, 1200, 1100, 1040, 800 |
| Ultraviolet absorption ($\lambda_{max}^{EtOH}$, nm) | 227 (ε16000) 268 (ε25000) 280 (ε22000) 323 (ε50000) | 226 (ε15000) 268 (ε24000) 281 (ε22000) 323 (ε47000) | 209 (ε20000) 227 (ε14000) 267 (ε26000) 280 (ε21000) 324 (ε49000) | 209 (ε20000) 226 (ε14000) 266 (ε25000) 280 (ε23000) 324 (ε51000) |
| Mass spectrum (SIMS, m/z) | (C.I.) 395 [C₂₂H₂₃N₂O₅]⁺ Same as in compound 64 | 395 [C₂₂H₂₃N₂O₅]⁺ | | 425 [C₂₃H₂₅N₂O₆]⁺ Same as in the left |
| Proton NMR (DMSO-d₆, δ in ppm, CD₂HSOCD₃ proton chemical shift (δ 2.50) was used as internal standard, intensity of NMR magnetic field was indicated in each compound) | | 2.86 (3H,s) 3.70 (2H,m) 4.16 (1H,q) 4.36 (1H,q) 4.58 (1H,t) 5.18 (1H,t) 5.68 (1H,d) 6.16 (1H,d) 6.35 (1H,d,J=3Hz 1'-H) 7.18 (1H,dd,J=2,9Hz) 7.54 (1H, d,J=9Hz) 7.86 (1H,d,J=2Hz) 8.50 (1H,d,J=7.5Hz) 8.58 (1H,d,J=7.5Hz) 9.44 (1H,s) 9.97 (1H,s) 12.03 (1H,brs) | | 425 [C₂₃H₂₅N₂O₆]⁺ 2.86 (3H,s) 3.77 (1H,m) 3.95 (1H,m) 4.00 (1H,m) 4.10 (2H,m) 4.91 (1H,t) 5.44 (1H,d) 5.48 (1H,d) 5.64 (1H,d) 6.15 (1H,d,J=8.5Hz,1'-H) 7.18 (1H,dd,J=2,9Hz) 7.55 (1H, d, J=9Hz) 7.86 (1H,d,J=2Hz) 8.51 (1H,d,J=7.5Hz) 8.58 (1H,d, J=7.5Hz) 9.44 (1H,brs) 10.07 (1H,s) 12.06 (1H,brs) |
| Elementary analysis Molecular formula | | C₂₂H₂₃N₂O₅Br·1.5H₂O | | |
| Calc. (C, H, N) % | 52.60, 5.22, 5.58 | 52.60, 5.22, 5.58 | | |
| Found (C, H, N) % | 52.51, 5.23, 5.61 | 52.49, 5.14, 5.41 | | |

| Example No. | 67 | 68 | 69 |
|---|---|---|---|
| R | (D-Tal) | (L-Tal) | (L-Gal) | (D-All) |
| X⁻ | Br | Br | Br |
| Crystalline form | Amorphous reddish orange powder | Amorphous reddish orange powder | Amorphous yellow powder |

TABLE 1-continued

| | Example No. 69 | 70 | 71 | 72 |
|---|---|---|---|---|
| R | (L-All) structure: HO, OH, CH₂OH pyranose | (L-Glc) structure: HO, OH, OH, CH₂OH pyranose | structure with HO, OH, OH, CH₃ (1',2',3',4' labeled) | (D-2d Rib) structure: OH, CH₂OH |
| X⁻ | Br | Br | Br | Cl |
| Crystalline form Specific rotatory power [α]_D | Amorphous yellow powder +390° (C = 0.25) | Amorphous red powder +310° (C = 0.17) | Amorphous red powder −300° (C = 0.12, 1% CF₃COOH/H₂O) | Amorphous red powder −88° (C = 0.20) |
| Infrared absorption (KBr, cm⁻¹) | 3300, 1640, 1600, 1470, 1420, 1220, 1120, 1040, 820 | 3250, 1640, 1600, 1470, 1420, 1220, 1200, 1100, 1060, 810 | 3200, 1640, 1590, 1470, 1420, 1380, 1210, 1190, 810 | 3230, 1600, 1470, 1430, 1220, 1100, 1060, 810 |
| Ultraviolet absorption (λ_max^EtOH, nm) | 207 (ε20000) 226 (ε14000) 268 (ε26000) 280 (ε23000) 324 (ε51000) | 209 (ε21000) 227 (ε14000) 267 (ε30000) 281 (ε22000) 324 (ε50000) | 207 (ε21000) 226 (ε15000) 267 (ε24000) 280 (ε21000) 323 (ε48000) | 207 (ε18000) 227 (ε13000) 249 (ε20000) 267 (ε21000) 280 (ε19000) 321 (ε42000) |
| Mass spectrum (SIMS, m/z) | 425 [C₂₃H₂₅N₂O₆]⁺ | 425 [C₂₃H₂₅N₂O₆]⁺ | 409 [C₂₃H₂₅O₅N₂]⁺ | 379 (C.I.) [C₂₂H₂₃N₃O₄]⁺ |

| | Example No. (continued) | | | |
|---|---|---|---|---|
| Specific rotatory power [α]_D | +410° (C = 0.13) | −400° (C = 0.21) | +320° (C = 0.21) | −380° (C = 0.28) |
| Infrared absorption (KBr, cm⁻¹) | 3250, 1640, 1600, 1480, 1420, 1220, 1200, 1100, 1060, 820 | 3250, 1640, 1600, 1480, 1420, 1220, 1200, 1100, 1060, 820 | 3200, 1640, 1590, 1470, 1420, 1220, 1200, 1090, 810 | 3300, 1640, 1600, 1470, 1420, 1220, 1120, 1040, 820 |
| Ultraviolet absorption (λ_max^EtOH, nm) | 204 (ε22000) 226 (ε15000) 268 (ε25000) 280 (ε23000) 324 (ε50000) | 204 (ε22000) 226 (ε15000) 268 (ε25000) 280 (ε23000) 324 (ε50000) | 206 (ε22000) 226 (ε15000) 268 (ε26000) 281 (ε23000) 324 (ε50000) | 207 (ε20000) 226 (ε14000) 268 (ε26000) 280 (ε23000) 324 (ε51000) |
| Mass spectrum (SIMS, m/z) | 425 [C₂₃H₂₅N₂O₆]⁺ | 425 [C₂₃H₂₅N₂O₆]⁺ | 425 [C₂₃H₂₅N₂O₆]⁺ | 425 [C₂₃H₂₅N₂O₆]⁺ |
| Proton NMR (DMSO-d₆, δ in ppm, CD₂HSOCD₃ proton chemical shift (δ 2.50) was used as internal standard Intensity of NMR magnetic field was indicated in each compound) | 2.83 (3H,s) 3.29 (3H,s) 3.74 (1H,m) 3.90 (1H,m) 4.03 (1H,m) 4.09 (1H,m) 4.20 (2H,m) 4.73 (1H,brs) 5.29 (1H,d) 5.36 (1H,d) 5.57 (1H,d) 6.09 (1H,d,J=9Hz,1'-H) 7.17 (1H,dd,J=2,9Hz) 7.53 (1H,d,J=9Hz) 7.83 (1H,d,J=2Hz) 8.43 (1H,d, J=7.5Hz) 8.57 (1H,d,J=7.5Hz) 9.43 (1H,brs) 10.05 (1H,s) 12.05 (1H,brs) | Same as in the left | 2.83 (3H,s) 3.28 (3H,s) 3.70 (3H,m) 3.90 (3H,m) 4.87 (1H, brs) 4.97 (1H,d) 5.25 (1H,d) 5.62 (1H,brs) 5.82 (1H,d,J=8.5Hz,1'-H) 7.18 (1H,d,J=2,9Hz) 7.54 (1H,dd,J=9Hz) 7.84 (1H,d,J=2Hz) 8.48 (2H,s) 9.46 (1H,brs) 10.03 (1H,s) 12.05 (1H,brs) | 2.83 (3H,s) 3.29 (3H,s) 4.74 (1H,brs) 5.08 (1H,d) 5.40 (1H,brs) 5.52 (1H,d) 6.05 (1H,d,J=9Hz,1'-H) 7.18 (1H,dd,J=2,9Hz) 7.53 (1H,d,J=9Hz) 7.83 (1H,d,J=2Hz) 8.44 (1H,d, J=7.5Hz) 8.58 (1H,d,J=7.5Hz) 9.44 (1H,brs) 10.05 (1H,s) 12.06 (1H,brs) |
| Elementary analysis Molecular formula | C₂₃H₂₅N₂O₆Br.1.5H₂O | C₂₃H₂₅N₂O₆Br.1.5H₂O | — | C₂₃H₂₅N₂O₆Br.H₂O |
| Calc. (C, H, N) % Found (C, H, N) % | 51.88, 5.30, 5.26 51.61, 5.20, 5.26 | 51.88, 5.30, 5.26 51.79, 5.15, 5.23 | | 52.78, 5.20, 5.35 52.76, 5.14, 5.31 |

TABLE 1-continued

| | | | |
|---|---|---|---|
| Proton NMR (DMSO-d6, δ in ppm, CD2HSOCD3 proton chemical shift δ 2.50) was used as internal standard, Intensity of NMR magnetic field was indicated in each compound) | same as in the left | 2.85 (3H,s) 3.46–3.84 (6H,m) 4.79 (1H,t) 5.37 (1H,t) 5.52 (1H,d) 5.71 (1H,d) 5.88 (1H,d,J=9Hz,1'-H) 7.19 (1H,dd,J=2,9Hz) 7.55 (1H,d,J=9Hz) 7.86 (1H,d,J=2Hz) 8.47 (1H,d, J=7.5Hz) 8.58 (1H,d,J=7.5Hz) 9.46 (1H,s) 10.05 (1H,s) 12.11 (1H,brs) | 1.53 (3H,d,J=7Hz) 2.85 (3H,s) 3.30 (3H,s) 3.70, 4.00, 4.10, 4.32 (each 1H,m) 5.38, 5.46, 5.63 (each 1H,d) 6.22 (1H,d, J=8.5Hz,1'-H) 7.17 (1H,dd, J=2,9Hz) 7.54 (1H,d,J=9Hz) 7.86 (1H,d,J=2Hz) 8.47 (1H,d, J=7.5Hz) 8.56 (1H,d,J=7.5Hz) 9.45 (1H,s) 10.08 (1H,s) 12.08 (1H,brs) (360MHz) | 2.67 (1H,s) 2.84 (3H,s) 3.72 (3H,s) 3.77 (1H,m) 3.86 (1H,m) 4.16 (1H,m) 4.48 (1H,m) 5.55 (2H,m) 6.67 (1H,t,J=6Hz,1'-H) 7.16 (1H,dd,J=2,9Hz) 7.53 (1H, d,J=9Hz) 7.83 (1H,d,J=2Hz) 8.47 (1H,d,J=7.5Hz) 8.68 (1H, d,J=7.5Hz) 9.47 (1H,brs) 10.27 (1H,s) 12.08 (1H,brs) |
| Elementary analysis Molecular formula | | C23H25N2O6Br·H2O | C23H25N2O5Br·2H2O | — |
| Calc. (C, H, N) % | | 52.78, 5.20, 5.35 | 52.58, 5.56, 5.33 | |
| Found (C, H, N) % | | 52.59, 5.34, 5.29 | 52.61, 5.21, 5.35 | |

| Example No. | 73 | 74 | 75 | 76 |
|---|---|---|---|---|

[structures shown: Ex. 73 (D-5d Rib); Ex. 74 (L-5d Ara); Ex. 75 and 76 pyranose with OH, OH, CH3]

| R | (D-5d Rib) | (L-5d Ara) | | |
|---|---|---|---|---|
| X⁻ | Cl | Cl | Br | Br |
| Crystalline form Specific rotatory power [α]D | Amorphous orange powder −240° (C = 0.17) | Amorphous red powder −24° (C = 0.19) | Amorphous red powder −210° (C = 0.14 1% CF3COOH/H2O) | Amorphous red powder +190° (C = 0.19 1% CF3COOH/H2O) |
| Infrared absorption (KBr, cm⁻¹) | 3230, 1600, 1470, 1430, 1220, 1100, 1060, 820 | 3220, 1640, 1600, 1480, 1430, 1390, 1220, 1100, 1060, 920, 810 | 3304, 1647, 1600, 1483, 1434, 1220, 1155, 1106 | 3304, 1647, 1600, 1483, 1434, 1220, 1155, 1106 |
| Ultraviolet absorption (λmax EtOH, nm) | 210 (ε19000) 226 (ε14000) 268 (ε23000) 325 (ε46000) | 209 (ε21000) 226 (ε15000) 267 (ε25000) 279 (ε22000) 323 (ε50000) | 226 (ε15000) 267 (ε25000) 280 (ε22000) 324 (ε49000) | Same as in the left |
| Mass spectrum (SIMS, m/z) | (C.I.) 379 [C22H23N2O4]⁺ | (C.I.) 379 [C22H23N2O4]⁺ | 409 [C23H25O5N2]⁺ | 409 [C23H25O5N2]⁺ |
| Proton NMR (DMSO-d6, δ in ppm, CD2HSOCD3 proton chemical shift δ 2.50) was used as internal standard, Intensity of NMR magnetic field was indicated in each compound) | 1.53 (3H,d,J=6.5Hz) 2.86 (3H, s) 3.96 (1H,q) 4.32 (1H,d) 4.39 (1H,t) 5.54 (1H,d) 5.88 (1H,d) 6.28 (1H,d,J=5.5Hz,1'-H) 7.18 (1H,d,J=2,9Hz) 7.54 (1H,d,J=9Hz) 7.84 (1H,d, J=2Hz) 8.43 (1H,d,J=7.5Hz) 8.48 (1H,d,J=7.5Hz) 9.49 (1H,brs) 9.98 (1H,s) 12.08 (1H,brs) | 1.44 (3H,d,J=6.5Hz) 2.86 (3H, s) 3.91 (1H,m) 4.35 (1H,m) 4.71 (1H,m) 5.71 (1H,d) 6.24 (1H,d) 6.39 (1H,d,J=2.5Hz,1'-H) 7.18 (1H,dd,J=2,9Hz) 7.55 (1H,d,J=9Hz) 7.86 (1H,d, J=2Hz) 8.48 (1H,d,J=7.5Hz) 8.57 (1H,d,J=7.5Hz) 9.46 (1H,brs) 9.96 (1H,s) 12.07 (1H,brs) | 1.30 (3H,d,J=6.5Hz) 2.85 (3H, s) 3.65 (2H,m) 3.87 (1H,m) 4.04 (1H,q) 4.96, 5.20, 5.56 (each 1H,d) 5.78 (1H,d,J=9Hz, 1'-H) 7.19 (1H,dd,J=2,9Hz) 7.56 (1H,d,J=9Hz) 7.86 (1H,d, J=2Hz) 8.52 (2H,q) 9.46 (1H,s) 10.04 (1H,s) 12.10 (1H,brs) (300MHz) | same as in the left |
| Elementary analysis Molecular formula | | C22H23N2O4Cl·2H2O | C23H25N2O5Br | C23H25N2O5Br |
| Calc. (C, H, N) % | | 58.59, 6.04, 6.21 | 56.45, 5.15, 5.73 | 56.45, 5.15, 5.73 |

TABLE 1-continued

| Example No. | 77 | 77 | 78 | 79 |
|---|---|---|---|---|
| R | (D-Xyl) | (L-Xyl) | (D-Xyl) | (D-Ery) |
| X⁻ | Cl | Cl | Br | Cl |
| Crystalline form | Amorphous yellow powder | Amorphous yellow powder | Amorphous yellowish orange powder | Amorphous reddish orange powder |
| Specific rotatory power $[\alpha]_D$ | +150° (C = 0.17) | −170° (C = 0.35) | +140° (C = 0.22) | −240° (C = 0.14) |
| Infrared absorption (KBr, cm$^{-1}$) | 3260, 1640, 1590, 1500, 1470, 1420, 1320, 1210, 1090, 1020, 830, 800, 720 | 3260, 1640, 1590, 1500, 1470, 1420, 1320, 1210, 1090, 1020, 830, 800, 720 | 3270, 1650, 1600, 1480, 1430, 1390, 1320, 1220, 1100, 840, 810, 720 | 3220, 1600, 1470, 1430, 1220, 1110, 1060, 820 |
| Ultraviolet absorption ($\lambda_{max}^{EtOH}$, nm) | 210 (ε21000) 226 (ε15000) 268 (ε26000) 280 (ε24000) 322 (ε51000) | 209 (ε22000) 226 (ε16000) 267 (ε26000) 280 (ε24000) 322 (ε52000) | 226 (ε17000) 268 (ε26000) 280 (ε23000) 322 (ε52000) | 210 (ε18000) 226 (ε13000) 267 (ε22000) 324 (ε45000) |
| Mass spectrum (SIMS, m/z) | 395 [C$_{22}$H$_{23}$N$_2$O$_5$]$^+$ | 395 [C$_{22}$H$_{23}$N$_2$O$_5$]$^+$ same as in the left | 395 [C$_{22}$H$_{23}$N$_2$O$_5$]$^+$ | 365 [C$_{21}$H$_{21}$N$_2$O$_4$]$^+$ |
| Proton NMR (DMSO-d$_6$, δ in ppm, CD$_2$HSOCD$_3$ proton chemical shift (δ 2.50) was used as internal standard. Intensity of NMR magnetic field was indicated in each compound) | 2.78 (3H,s) 3.22 (2H,s) 3.97 (2H,m) 4.15 (1H,q) 4.34 (1H,s) 4.49 (1H,q) 5.12 (1H,brs) 5.73 (1H,brs) 6.39 (1H,brs) 6.32 (1H,s,1'-H) 7.16 (1H,dd,J=2,9Hz) 7.50 (1H,d,J=9Hz) 7.78 (1H,d,J=2Hz) 8.44 (1H,d, J=7.5Hz) 8.62 (1H,d,J=7.5Hz) 9.47 (1H,brs) 10.00 (1H,s) 12.05 (1H,brs) | | 2.83 (3H,s) 3.26 (3H,s) 3.96 (2H,m) 4.15 (1H,d) 4.34 (1H,s) 4.49 (1H,q) 5.14 (1H,brs) 5.79 (1H,brs) 6.39 (1H,brs) 6.30 (1H,s,1'-H) 7.17 (1H,dd,J=2,9Hz) 7.53 (1H,d,J=9Hz) 7.83 (1H,d,J=2Hz) 8.48 (1H,d, J=7.5Hz) 8.61 (1H,d,J=7.5Hz) 9.52 (1H,brs) 10.10 (1H,brs) 12.07 (1H,brs) | 2.85 (3H,s) 3.30 (3H,s) 4.09 (1H,d) 4.28 (1H,m) 4.44 (1H,t) 4.72 (1H,dd) 5.58 (1H,d) 5.94 (1H,d) 6.26 (1H,d,J=6.5Hz,1'-H) 7.18 (1H,s,1'-H) 7.53 (1H,d,J=9Hz) 7.84 (1H,d, J=2Hz) 8.47 (1H,d,J=7.5Hz) 8.54 (1H,d,J=2Hz) 9.48 (1H, s) 10.01 (1H,s) 12.15 (1H,brs) |
| Elementary analysis Molecular formula Calc. (C, H, N) % Found (C, H, N) % | C$_{22}$H$_{23}$N$_2$O$_5$Cl·H$_2$O 58.86, 5.61, 6.24 58.77, 5.32, 6.35 | 58.91, 5.64, 6.61 | C$_{22}$H$_{23}$N$_2$O$_5$Br·H$_2$O — 56.63, 5.01, 5.95 | C$_{21}$H$_{21}$N$_2$O$_4$Cl·2H$_2$O — 56.71, 5.01, 5.69 |
| Found (C, H, N) % | | | | |

| Example No. | 79 | 80 | 81 | 82 |
|---|---|---|---|---|
| R | (L-Eryl) | (L-Rib) | (D-Rib) | (L-Rib) |
| X⁻ | Cl | Br | Br | Br |
| Crystalline form | Amorphous reddish orange | Amorphous red powder | Amorphous red powder | Amorphous orange powder |

Found (C, H, N) %: 58.86, 5.61, 6.24 / 58.67, 5.37, 6.27 (Ex. 80); 57.72, 5.77, 6.41 / 57.41, 5.49, 6.42 (Ex. 82)

TABLE 1-continued

| | | | |
|---|---|---|---|
| Specific rotatory power [α]_D | +220° (C = 0.23) | +310° (C = 0.28) | −330° (C = 0.20) | +190° (C = 0.11) |
| Infrared absorption (KBr, cm$^{-1}$) | 3220, 1600, 1470, 1430, 1220, 1110, 1060, 820 | 3200, 1640, 1600, 1430, 1260, 1190, 1100, 1050, 800 | 3250, 1640, 1600, 1480, 1430, 1220, 1180, 1100, 1040, 980, 820 | 3200, 1640, 1580, 1460, 1220, 1100, 800 |
| Ultraviolet absorption (λ$_{max}^{EtOH}$, nm) | 210 (ε18000) 226 (ε13000) 267 (ε22000) 324 (ε45000) | 222 (ε15000) 268 (ε25000) 281 (ε22000) 324 (ε50000) | 209 (ε21000) 226 (ε15000) 268 (ε26000) 281 (ε23000) 324 (ε51000) | 206 (ε20000) 226 (ε15000) 267 (ε25000) 280 (ε22000) 324 (ε48000) |
| Mass spectrum (SIMS, m/z) | 365 [C$_{21}$H$_{21}$N$_2$O$_4$]$^+$ | 395 [C$_{22}$H$_{23}$N$_2$O$_5$]$^+$ | (C.I.) 395 [C$_{22}$H$_{23}$N$_2$O$_5$]$^+$ | 395 [C$_{22}$H$_{23}$N$_2$O$_5$]$^+$ |
| Proton NMR (DMSO-d$_6$, δ in ppm, CD$_2$HSOCD$_3$ proton chemical shift (δ 2.50) was used as internal standard, Intensity of NMR magnetic field was indicated in each compound) | Same as in the left | Same as in compound 81 | 2.86 (3H,s) 3.87 (2H,m) 3.94 (2H,m) 4.08 (1H,m) 5.11 (1H,d) 5.38 (1H,d) 5.47 (1H,d) 5.98 (1H,d,J=9Hz,1'-H) 7.18 (1H,dd,J=2,9Hz) 7.56 (1H,d,J=9Hz) 7.87 (1H,d,J=2Hz) 8.46 (1H,d, J=7.5Hz) 8.56 (1H,d,J=7.5Hz) 9.44 (1H,s) 10.06 (1H,s) 12.09 (1H,brs) | 2.81 (3H,s) 3.33 (3H,s) 3.81, 3.93 (each 1H,m) 4.26 (2H,m) 4.35 (1H,m) 5.47 (1H,d) 5.89 (1H,d) 5.64 (1H,t) 6.28 (1H,d,J=5Hz,1'-H) 7.16 (1H,dd,J=2, 9Hz) 7.50 (1H,d,J=9Hz) 7.79 (1H,d,J=2Hz) 8.46 (1H,d, J=7.5Hz) 8.64 (1H,d,J=7.5Hz) 9.44 (1H,s) 10.23 (1H,s) 12.04 (1H,s) |
| Elementary analysis Molecular formula Calc. (C, H, N)% Found (C, H, N)% | | C$_{21}$H$_{21}$N$_2$O$_4$Cl·2H$_2$O 57.72, 5.77, 6.41 57.80, 5.53, 6.40 | C$_{22}$H$_{23}$N$_2$O$_5$Br·1.5H$_2$O 52.60, 5.22, 5.58 52.80, 5.08, 5.66 | C$_{22}$H$_{23}$N$_2$O$_5$Br·1.5H$_2$O 52.60, 5.22, 5.58 52.97, 5.07, 5.62 | |

| Example No. | 83 | 84 | 85 | 86 |
|---|---|---|---|---|
| R | (structure with 2',3',4',5') ‒OH | (D-Ara) | (L-Ara) | (D-Lyx) |
| X$^-$ | Br$^-$ | Br | Br | Cl |
| Crystalline form | Amorphous orange powder | Amorphous red powder | Amorphous orange powder | Amorphous reddish orange powder |
| Specific rotatory power [α]_D | −180° (C = 0.16, 1(v/v % CF$_3$CO$_2$H/H$_2$O) | +230° (C = 0.20) | −240° (C = 0.19) | +250° (C = 0.42) |
| Infrared absorption (KBr, cm$^{-1}$) | 3222, 1647, 1598, 1483, 1434, 1393, 1294, 1220, 1106 | 3250, 1640, 1590, 1420, 1190, 1140, 1090, 920, 810, 740 | 3250, 1640, 1600, 1480, 1420, 1220, 1200, 1150, 1090, 1060, 810 | 3240, 1600, 1470, 1430, 1220, 1150, 1100, 820 |
| Ultraviolet absorption (λ$_{max}^{EtOH}$, nm) | 226 (ε13000) 268 (ε23000) 281 (ε20000) 323 (ε46000) | 227 (ε14000) 267 (ε25000) 281 (ε22000) 324 (ε48000) | 227 (ε14000) 268 (ε24000) 281 (ε21000) 325 (ε47000) | 209 (ε17000) 227 (ε13000) 267 (ε20000) 323 (ε42000) |
| Mass spectrum (SIMS, m/z) | 395 [C$_{22}$H$_{23}$O$_5$N$_2$]$^+$ | (C.I.) 395 [C$_{22}$H$_{23}$N$_2$O$_5$]$^+$ | 395 [C$_{22}$H$_{23}$N$_2$O$_5$]$^+$ | 395 [C$_{22}$H$_{23}$N$_2$O$_5$]$^+$ |
| Proton NMR | 2.84 (3H,s) 3.35 (3H,s) 3.80, | 2.85 (3H,s) 3.65 (1H,m) 3.90 | Same as in compound 84 | 2.84 (3H,s) 3.26 (3H,s) 3.68 |

TABLE 1-continued

| | | | | | |
|---|---|---|---|---|---|
| (DMSO-d$_6$, δ in ppm, CD$_2$HSOCD$_3$ proton chemical shift (δ 2.50) was used as internal standard, Intensity of NMR magnetic field was indicated in each compound) | 3.92 (each 1H,q) 4.26 (2H,m) 4.34 (1H,m) 5.47, 5.85, (each 1H,d,) 5.62 (1H,t) 6.28 (1H,d, J=5Hz,1'-H) 7.18 (1H,dd,J=2, 9Hz) 7.54 (1H,d,J=9Hz) 7.85 (1H,d,J=2Hz) 8.52 (1H,d, J=7.5Hz) 8.63 (1H,d,J=7.5Hz) 9.45 (1H,s) 10.26 (1H,s) 12.04 (1H,brs) (360MHz) | (3H,m) 4.08 (1H,d) 5.12 (1H,d) 5.24 (1H,d) 5.61 (1H,d) 5.74 (1H,d,J=8.5Hz,1'-H) 7.18 (1H,dd,J=2,9Hz) 7.55 (1H,d,J=9Hz) 7.86 (1h,d,J=2Hz) 8.51 (2H, AB quartet) 9.45 (1H,brs) 10.03 (1H,s) 12.08 (1H,brs) | | | (1H,m) 3.80 (1H,m) 4.23 (1H,m) 4.55 (1H,brs) 4.79 (1H,m) 4.91 4.91 (1H,t) 5.57 (1H,d) 5.94 (1M,brs) 6.27 (1H,d,J=6.5Hz,1'-H) 7.16 (1H,dd,J=2,9Hz) 7.53 (1H,d,J=9Hz) 7.82 (1H, brs) 8.46 (1H,d,J=9Hz) 8.54 (1H,d,J=7.5Hz) 9.48 (1H,brs) 9.99 (1H,s) 12.14 (1H,brs) |
| Elementary analysis Molecular formula Calc. (C, H, N)% Found (C, H, N)% | C$_{22}$H$_{23}$N$_2$O$_5$Br 55.59, 4.88, 5.89 55.41, 4.90, 5.99 | C$_{22}$H$_{23}$N$_2$O$_5$Br.2H$_2$O 51.67, 5.32, 5.48 51.71, 5.06, 5.37 | | C$_{22}$H$_{23}$N$_2$O$_5$Br.2H$_2$O 51.67, 5.32, 5.48 51.57, 5.31, 5.40 | — |
| Example No. | 87 | 88 | 89 | | 90 |
| R | HO、、、\ OH \ /CH$_2$OH O (L-Lyx) | HO、、、\ OH \ O (L-Lyx) | HO、、、\ OH \ O (D-Lyx) | | AcHN OH CH$_2$OH O (D-Glc NAc) |
| X$^-$ | Cl | Cl | Cl | | Cl |
| Crystalline form | Amorphous reddish orange powder | Amorphous orange powder | Amorphous orange powder | | Amorphous reddish orange powder |
| Specific rotatory power [α]$_D$ | −280° (C = 0.14) | −320° (C = 0.19) | +400° (C = 0.09) | | −280° (C = 0.10) |
| Infrared absorption (KBr, cm$^{-1}$) | 3240, 1600, 1470, 1430, 1220, 1150, 1100, 820 | 3250, 1640, 1600, 1480, 1420, 1220, 1180, 1050, 810 | 3250, 1640, 1600, 1480, 1420, 1220, 1180, 1050, 810 | | 3250, 1660, 1590, 1480, 1420, 1290, 1220, 1050, 800 |
| Ultraviolet absorption (λ$_{max}^{EtOH}$, nm) | 208 (ε20000) 226 (ε15000) 267 (ε24000) 324 (ε48000) | 210 (ε20000) 226 (ε14000) 268 (ε24000) 281 (ε22000) 324 (ε49000) | 209 (ε20000) 226 (ε14000) 268 (ε25000) 280 (ε22000) 324 (ε49000) | | 227 (ε15000) 269 (ε25000) 326 (ε47000) |
| Mass spectrum (SIMS m/z) | 395 [C$_{22}$H$_{23}$N$_2$O$_5$]$^+$ same as in compound 86 | 395 [C$_{22}$H$_{23}$N$_2$O$_5$]$^+$ same as in compound 89 | 395 [C$_{22}$H$_{23}$N$_2$O$_5$]$^+$ | | 466 [C$_{25}$H$_{28}$N$_3$O$_6$]$^+$ |
| Proton NMR (DMSO-d$_6$, δ in ppm, CD$_2$HSOCD$_3$ proton chemical shift (δ 2.50) was used as internal standard, Intensity of NMR magnetic field was indicated in each compound) | 9.46 (1H,brs) 10.07 (1H,s) J=9.5Hz) 8.41 (1H,d,J=7.5Hz) | 2.86 (3H,s) 3.74 (1H,m) 4.00 (3H,m) 4.16 (1H,d) 5.38 (1H,d) 5.48 (1H,d) 5.69 (1H,d) 6.02 (1H,d,J=9Hz,1'-H) 7.18 (1H,dd,J=2,9Hz) 7.55 (1H,d,J=9Hz) 7.87 (1H,d,J=2Hz) 8.50 (1H,d, J=7.5Hz) 8.55 (1H,d,J=7.5Hz) 12.13 (1H,brs) | | | 1.52 (3H,s) 2.84 (3H,s) 3.30 (3H,s) 3.63 (4H,m) 3.85 (1H,m) 4.10 (1H,q,J=9.5Hz) 4.48 (1H,t) 5.48 (2H,m) 5.93 (1H,d,J=9.5Hz,1'-H) 7.18 (1H,dd,J=2,9Hz) 7.54 (1H,d,J=2Hz) 7.85 (1H,d,J=2Hz) 8.26 (1H,d, 8.54 (1H,d,J=7.5Hz) 9.49 (1H, s) 9.98 (1H,s) 12.14 (1H,s) |
| Elementary analysis | — | C$_{22}$H$_{23}$N$_2$O$_5$Cl.1.5H$_2$O | C$_{22}$H$_{23}$N$_2$O$_5$Cl.1.5H$_2$O | | — |

TABLE 1-continued

| | | | | |
|---|---|---|---|---|
| Example No. | 91 | 92 | 93 | 94 |
| Molecular formula Calc. (C, H, N)% Found (C, H, N)% | | 57.70, 5.72, 6.12 57.32, 5.33, 5.96 | 57.70, 5.72, 6.12 57.56, 5.49, 6.05 | 57.70, 5.72, 6.12 |
| R | (D-Gal NAc) [AcHN, OH, CH₂OH structure] | (D-Glc UAm) [HO, OH, CONH₂ structure] | (D-Xyl) [HO, OH structure] | (L-Xyl) [HO, OH structure] |
| X⁻ | Cl | Br | Br | Br |
| Crystalline form | Amorphous reddish orange powder | Amorphous orange powder | Amorphous orange powder | Amorphous orange powder |
| Specific rotatory power $[\alpha]_D$ | −190° (C = 0.13) | −220° (C = 0.13) | −230° (C = 0.12) | +260° (C = 0.16) |
| Infrared absorption (KBr, cm⁻¹) | 3230, 1660, 1590, 1470, 1420, 1290, 1220, 1100, 800 | 3300, 1680, 1640, 1600, 1470, 1420, 1200, 1090, 800 | 3250, 1640, 1600, 1480, 1430, 1200, 1100, 1060, 810 | 3250, 1640, 1600, 1480, 1430, 1200, 1100, 1060, 810 |
| Ultraviolet absorption ($\lambda_{max}^{EtOH}$, nm) | 206 (ε19000) 227 (ε13000) 269 (ε22000) 326 (ε43000) | 226 (ε15000) 268 (ε25000) 325 (ε48000) | 226 (ε15000) 268 (ε26000) 325 (ε50000) | 226 (ε13000) 268 (ε24000) 281 (ε21000) 324 (ε47000) |
| Mass spectrum (SIMS, m/z) | 466 $[C_{25}H_{28}N_3O_6]^+$ | 438 $[C_{23}H_{24}N_3O_6]^+$ | 395 $[C_{22}H_{23}N_2O_5]^+$ | (C.I.) 395 $[C_{22}H_{23}N_2O_5]^+$ |
| Proton NMR (DMSO-d₆, δ in ppm, CD₂HSOCD₃ proton chemical shift (δ 2.50) was used as internal standard, Intensity of NMR magnetic field was indicated in each compound) | 1.53 (3H,s) 2.84 (3H,s) 3.67–3.91 (5H,m) 4.41 (1H,q) 4.88 (1H,t) 5.14 (1H,d) 5.18 (1H,d) 5.82 (1H,d,J=9.5Hz,1′-H) 7.19 (1H,dd,J=2,9Hz) 7.56 (1H,d, J=9Hz) 7.87 (1H,d,J=2Hz) 8.14 (1H,d,J=9Hz) 8.48 (2H,ABq type) 9.48 (1H,brs) 9.97 (1H,s) 12.13 (1H,brs) | 2.86 (3H,s) 3.50 (1H,m) 3.75 (2H,m) 3.95 (1H,d) 5.52 (1H,d) 5.65 (1H,d) 5.78 (1H,d) 5.93 (1H,d,J=9Hz,1′-H) 7.18 (1H,dd,J=2,9Hz) 7.41 (1H,s) 7.73 (1H, s) 7.56 (1H,d,J=9Hz) 7.86 (1H, d,J=2Hz) 8.48 (1H,d,J=7.5Hz) 8.55 (1H,d,J=7.5Hz) 9.48 (1H, brs) 10.06 (1H,s) 12.13 (1H,brs) | 2.86 (3H,s) 3.72 (3H,m) 4.10 (1H,q) 5.36 (1H,d) 5.55 (1H,d) 5.72 (1H,d) 5.80 (1H,d,J=9Hz,1′-H) 7.18 (1H,dd,J=2,9Hz) 7.56 (1H,d,J=9Hz) 7.86 (1H,d,J=2Hz) 8.46 (1H,d, J=7.5Hz) 8.56 (1H,d,J=7.5Hz) 9.45 (1H,brs) 10.03 (1H,s) 12.08 (1H,brs) | Same as in compound 93 |
| Elementary analysis Molecular formula Calc. (C, H, N)% Found (C, H, N)% | $C_{25}H_{28}N_3O_6Cl.3.5H_2O$ 53.14, 6.24, 7.44 53.52, 5.96, 7.36 | $C_{23}H_{24}N_3O_6Br.H_2O$ 51.50, 4.89, 7.83 51.21, 4.98, 7.51 | $C_{22}H_{23}N_2O_5Br.H_2O$ 51.67, 5.32, 5.48 51.53, 5.12, 5.29 | $C_{22}H_{23}N_2O_5Br.2H_2O$ 51.67, 5.32, 5.48 51.32, 4.92, 5.21 |
| Example No. | 95 | 96 | 96 | 97 |
| R | [HO, OH, CH₃ structure] | [HO, OH, CH₂OH structure] | [HO, OH, CH₂OH structure] | [HO, OH, CH₃ structure] |

TABLE 1-continued

| R | | (D-Ara) | (L-Ara) | (L-5d Ara) |
|---|---|---|---|---|
| X⁻ | $CH_3CO_2^-$ | AcO | AcO | AcO |
| Crystalline form | Amorphous orange powder | Amorphous dark red powder | Amorphous dark red powder | Amorphous dark red powder |
| Specific rotatory power $[\alpha]_D$ | −360° (C = 0.28, $H_2O$) −280° (C = 0.36 1% $CF_3COOH$/$H_2O$) | −800° ($\lambda$ = 320 nm) −610° ($\lambda$ = 262 nm) +340° ($\lambda$ = 231 nm) | +690° ($\lambda$ = 320 nm) +560° ($\lambda$ = 256 nm) −470° ($\lambda$ = 229 nm) | +590° ($\lambda$ = 314 nm) −720° ($\lambda$ = 227 nm) |
| Infrared absorption (KBr, $cm^{-1}$) | 3238, 1638, 1598, 1565, 1475, 1409, 1220, 1056 | 3200, 1600, 1480, 1400, 1290, 1220, 1120, 1070, 810 | 3180, 1600, 1480, 1400, 1290, 1220, 1120, 1070, 810 | 3170, 1590, 1470, 1400, 1220, 1060, 920, 800 |
| Ultraviolet absorption ($\lambda_{max}^{EtOH}$, nm) | 226 ($\epsilon$13000) 267 ($\epsilon$23000) 281 ($\epsilon$20000) 333 ($\epsilon$47000) | 210 ($\epsilon$19000) 226 ($\epsilon$15000) 266 ($\epsilon$23000) 281 ($\epsilon$21000) 322 ($\epsilon$45000) | 210 ($\epsilon$18000) 227 ($\epsilon$14000) 266 ($\epsilon$23000) 280 ($\epsilon$21000) 322 ($\epsilon$46000) | 208 ($\epsilon$18000) 226 ($\epsilon$15000) 266 ($\epsilon$21000) 280 ($\epsilon$20000) 322 ($\epsilon$37000) |
| Mass spectrum (SIMS, m/z) | 409 | 395 | (C.I.) 379 | |
| Proton NMR (DMSO-$d_6$, δ in ppm $CD_2HSOCD_3$ proton chemical shift (δ 2.50) was used as internal standard. Intensity of NMR magnetic field was indicated in each compound) | $[C_{23}H_{25}O_5N_2]^+$ 1.53 (3H,d,J=7Hz) 1.68 (3H,s) 2.78 (3H,s) 3.23 (3H,s) 3.68, 4.03, 4.07, 4.29 (each 1H,m) 6.24 (1H,d,J=8.5Hz, 1'-H) 7.14 (1H,dd,J=2.9Hz) 7.51 (1H,d,J=9Hz) 7.80 (1H,d,J=2Hz) 8.36 (1H,d,J=7.5Hz) 8.51 (1H,d,J=7.5Hz) 10.03 (1H,s) (300MHz) | $[C_{22}H_{23}N_2O_5]^+$ Broad signal observed in DMSO-$d_6$ | $[C_{22}H_{23}N_2O_5]^+$ Same as in the left | $[C_{22}H_{23}N_2O_4]^+$ DMSO-$d_6$ ($CF_3CO_2H$ 1 drop addition 1.58 (3H,d,J=6.5Hz) 1.90 (3H,s) 2.85 (3H,s) 3.30 (3H,s) 3.88 (1H,t) 4.18 (1H,m) 4.41 (1H,t) 6.59 (1H,d,J=5Hz,1'-H) 7.17 (1H,dd,J=2,9Hz) 7.53 (1H,d,J=9Hz) 7.84 (1H,d,J=2Hz) 8.38 (1H,d,J=7.5Hz) 8.44 (1H,d,J=7.5Hz) 9.90 (1H,s) 12.01 (1H,s) |
| Elementary analysis Molecular formula Calc. (C, H, N)% Found (C, H, N)% | $C_{25}H_{28}N_2O_7$ 64.09, 6.02, 5.98 64.09, 5.93, 5.95 | | | |

| Example No. | 98 | 98 | 99 | 99 |
|---|---|---|---|---|
| R | (D-Rib) | (L-Rib) | (D-Lyx) | (L-Lyx) |
| X⁻ | AcO | AcO | AcO | AcO |
| Crystalline form | Amorphous reddish orange powder | Amorphous reddish orange powder | Amorphous reddish orange powder | Amorphous reddish orange powder |
| Specific rotatory power $[\alpha]_D$ | −300° (C = 0.18) | +300° (C = 0.20) | +300° (C = 0.23) | −310° (C = 0.17) |
| Infrared absorption (KBr, $cm^{-1}$) | 3200, 1640, 1590, 1410, 1180, 1100, 1040, 820 | 3200, 1640, 1590, 1410, 1180, 1100, 1040, 820 | 3200, 1640, 1590, 1400, 1210, 1140, 1100, 1050, 820 | 3200, 1640, 1590, 1400, 1210, 1140, 1100, 1050, 820 |
| Ultraviolet absorption ($\lambda_{max}^{EtOH}$, nm) | 205 ($\epsilon$27000) 225 ($\epsilon$19000) 269 ($\epsilon$28000) 324 ($\epsilon$51000) | 205 ($\epsilon$27000) 225 ($\epsilon$19000) 269 ($\epsilon$28000) 324 ($\epsilon$51000) | 210 ($\epsilon$21000) 226 ($\epsilon$15000) 268 ($\epsilon$25000) 324 ($\epsilon$50000) | 210 ($\epsilon$21000) 226 ($\epsilon$15000) 268 ($\epsilon$25000) 324 ($\epsilon$50000) |

TABLE 1-continued

| Example No. | 100 | 100 | 101 | 101 |
|---|---|---|---|---|
| R | (L-Fuc) | (D-Fuc) | (D-Ara) | (L-Ara) |
| X⁻ | AcO | AcO | AcO | AcO |
| Crystalline form | Amorphous reddish orange powder | Amorphous reddish orange powder | Amorphous brown-dark brown powder | Amorphous brown-dark brown powder |
| Specific rotatory power [α]$_D$ | +210° (C = 0.18) | −200° (C = 0.23) | +300° (C = 0.16) | −290° (C = 0.15) |
| Infrared absorption (KBr, cm⁻¹) | 3200, 1640, 1590, 1480, 1410, 1200, 1150, 1100, 810 | 3200, 1640, 1590, 1480, 1410, 1200, 1150, 1100, 810 | 3200, 1650, 1600, 1460, 1420, 1100, 930, 820 | 3200, 1650, 1600, 1460, 1420, 1100, 930, 820 |
| Ultraviolet absorption (λ$_{max}$$^{EtOH}$, nm) | 210 (ε20000) 226 (ε14000) 267 (ε23000) 281 (ε20000) 325 (ε44000) | 210 (ε20000) 226 (ε14000) 267 (ε23000) 281 (ε20000) 325 (ε44000) | 207 (ε22000) 225 (ε15000) 268 (ε25000) 325 (ε47000) | 207 (ε22000) 225 (ε15000) 268 (ε25000) 325 (ε47000) |
| Mass spectrum (SIMS, m/z) | 409 | 409 | 395 | 395 |
| Proton NMR (DMSO-d$_6$, δ in ppm, CD$_3$SOCD$_3$ proton chemical shift (δ 2.50) was used as internal standard, Intensity of NMR magnetic field was indicated in each compound) | [C$_{23}$H$_{25}$N$_2$O$_5$]⁺ 1.30 (3H,d,J=6.5Hz) 1.68 (3H,s) 2.68 (3H,s) 3.07 (3H,s) 3.67 (2H,m) 3.93 (1H,t) 4.02 (1H,q) 5.76 (1H,d,J=9Hz,1′-H) 7.13 (1H,dd,J=2,9Hz) 7.49 (1H,d,J=9Hz) 7.74 (1H,s) 8.27 (1H,d, J=7.5Hz) 8.38 (1H,d,J=7.5Hz) 9.85 (1H,s) | [C$_{23}$H$_{25}$N$_2$O$_5$]⁺ Same as in the left | [C$_{22}$H$_{23}$N$_2$O$_5$]⁺ 1.68 (3H,s) 2.64 (3H,s) 3.01 (3H,s) 3.67 (1H,m) 3.87 (2H,m) 3.97 (1H,t) 4.04 (1H,m) 5.60 (1H,d,J=8.5Hz,1′-H) 7.09 (1H,dd,J=2,9Hz) 7.48 (1H,d,J=9Hz) 7.70 (1H,d,J=2Hz) 8.12 (1H,d,J=7.5Hz) 8.22 (1H,d, J=7.5Hz) 9.60 (1H,s) | [C$_{22}$H$_{23}$N$_2$O$_5$]⁺ Same as in the left |
| Elementary analysis Molecular formula Calc. (C, H, N) % Found (C, H, N) % | | | | |

| Mass spectrum (SIMS, m/z) | 395 | 395 |
|---|---|---|
| Proton NMR (DMSO-d$_6$, δ in ppm, CD$_3$SOCD$_3$ proton chemical shift (δ 2.50) was used as internal standard, Intensity of NMR magnetic field was indicated in each compound) | [C$_{22}$H$_{23}$N$_2$O$_5$]⁺ 1.71 (3H,s) 2.71 (3H,s) 3.13 (3H,s) 3.88 (4H,m) 4.15 (1H,s) 5.97 (1H,d, J=9Hz,1′-H) 7.12 (1H,dd, J=2,9Hz) 7.47 (1H,d, J=9Hz) 7.74 (1H,d,J=2Hz) 8.24 (1H,d,J=7.5Hz) 8.43 (1H,d,J=7.5Hz) 9.90 (1H,s) | [C$_{22}$H$_{23}$N$_2$O$_5$]⁺ 1.70 (3H,s) 2.72 (3H,s) 3.11 (3H,s) 3.67 (1H,q) 3.81 (1H,q) 4.24 (1H,t) 4.49 (1H,q) 4.75 (1H,m) 6.23 (1H,d,J=7Hz,1′-H) 7.10 (1H,dd,J=2,9Hz) 7.45 (1H,d,J=9Hz) 7.72 (1H,d,J=2Hz) 8.19 (1H,d,J=7.5Hz) 8.33 (1H,d,J=7.5Hz) 9.82 (1H,s) |

TABLE 1-continued

| Example No. | 102 | 102 | 103 | 103 |
|---|---|---|---|---|
| R | (L-Gal) | (D-Gal) | (D-Lyx) | (L-Lyx) |
| X− | AcO | AcO | AcO | AcO |
| Crystalline form | Amorphous brown-dark brown powder | Amorphous brown-dark brown powder | Amorphous reddish orange powder | Amorphous reddish orange powder |
| Specific rotatory power [α]_D | +300° (C = 0.19) | −310° (C = 0.22) | +410° (C = 0.17) | −350° (C = 0.23) |
| Infrared absorption (KBr, cm$^{-1}$) | 3250, 1640, 1580, 1410, 1200, 1090, 880, 800 | 3250, 1640, 1580, 1410, 1200, 1090, 880, 800 | 3200, 1640, 1590, 1420, 1300, 1220, 1180, 1080, 820 | 3200, 1640, 1590, 1420, 1300, 1220, 1180, 1080, 820 |
| Ultraviolet absorption ($\lambda_{max}^{EtOH}$, nm) | 206 (ε23000) 226 (ε16000) 269 (ε26000) 280 (ε23000) 324 (ε49000) | 206 (ε23000) 226 (ε16000) 269 (ε26000) 280 (ε23000) 324 (ε49000) | 208 (ε22000) 226 (ε15000) 267 (ε25000) 281 (ε22000) 324 (ε50000) | 208 (ε22000) 226 (ε15000) 267 (ε25000) 281 (ε22000) 324 (ε50000) |
| Mass spectrum (SIMS, m/z) | 425 | 425 | 395 | 395 |
| Proton NMR (DMSO-d_6, δ in ppm, CD_2HSOCD_3 proton chemical shift (δ 2.50) was used as internal standard, Intensity of NMR magnetic field was indicated in each compound) | [C$_{23}$H$_{25}$N$_2$O$_6$]$^+$ Same as in the right | [C$_{23}$H$_{25}$N$_2$O$_6$]$^+$ 1.70 (3H,s) 2.58 (3H,s) 2.98 (3H,m) 3.68 (3H,m) 3.87 (2H,m) 3.96 (1H,t) 5.74 (1H,d,J=9Hz,1′-H) 7.12 (1H,dd,J=2,9Hz) 7.45 (1H,d,J=9Hz) 7.68 (1H,d,J=2Hz) 8.17 (1H,d,J=7.5Hz) 8.33 (1H,d,J=7.5Hz) 9.76 (1H,s) | [C$_{22}$H$_{23}$N$_2$O$_5$]$^+$ 1.71 (3H,s) 2.71 (3H,s) 3.13 (3H,s) 3.73 (1H,d) 3.93 (1H,d) 4.05 (2H,m) 4.17 (1H,d) 6.02 (1H,d,J=9Hz,1′-H) 7.11 (1H,dd,J=2,9Hz) 7.47 (1H,d,J=9Hz) 7.73 (1H,d,J=2Hz) 8.27 (1H,d,J=7.5Hz) 8.43 (1H,d,J=7.5Hz) 9.90 (1H,s) | [C$_{22}$H$_{23}$N$_2$O$_5$]$^+$ Same as in the left |
| Elementary analysis Molecular formula Calc. (C, H, N) % Found (C, H, N) % | | | | |
| Example No. | 104 | 106 | 106 | 109 |

TABLE 1-continued

| R | (D-Xyl) | (L-Xyl) | (D-Xyl) | (L-5d Ara) |
|---|---|---|---|---|
| X⁻ | AcO | AcO | AcO | Cl |
| Crystalline form | Orange needle crystal (m.p. 225–229° C.) Water-insoluble, (impossible to determine) | Amorphous dark brown powder | Amorphous dark brown powder | Amorphous dark red powder |
| Specific rotatory power $[\alpha]_D$ | | +250° (C = 0.17) | −240° (C = 0.16) | +290° (λ = 321 nm) +180° (λ = 259 nm) −180° (λ = 231 nm) |
| Infrared absorption (KBr, cm⁻¹) | 3150, 1650, 1620, 1590, 1420, 1300, 1220, 1090, 840 | 3300, 1640, 1580, 1410, 1190, 1050, 920, 810 | 3300, 1640, 1580, 1410, 1190, 1050, 920, 810 | 3250, 1590, 1470, 1420, 1210, 1050, 800 |
| Ultraviolet absorption ($\lambda_{max}^{EtOH}$, nm) | 249 (Ethanol-insoluble, 268 impossible to determine) 281 323 | 210 (ε20000) 227 (ε15000) 250 (ε24000) 270 (ε26000) 325 (ε48000) | 210 (ε20000) 227 (ε15000) 250 (ε24000) 270 (ε26000) 325 (ε48000) | 218 (ε24000) 268 (ε18000) 281 (ε17000) 322 (ε27000) |
| Mass spectrum (SIMS, m/z) | (C.I.) 395 [$C_{22}H_{23}N_2O_5$]⁺ | 395 [$C_{22}H_{23}N_2O_5$]⁺ | 395 [$C_{22}H_{23}N_2O_5$]⁺ | 379 [$C_{22}H_{23}N_2O_4$]⁺ |
| Proton NMR (DMSO-$d_6$, δ in ppm, CD$_3$HSOCD$_3$ proton chemical shift (δ 2.50) was used as internal standard, Intensity of NMR magnetic field was indicated in each compound) | Impossible to determine (insoluble in DMSO-$d_6$) | | | 1.58 (3H,d,J=6.5Hz) 2.85 (3H,s) 3.30 (3H,s) 3.88 (1H,m) 4.18 (1H,m) 4.41 (1H,m) 5.74 (1H,d) 5.84 (1H,d) 6.60 (1H,d,J=5Hz,1'-H) 7.18 (1H,dd,J=2,9Hz) 7.54 (1H,d,J=9Hz) 7.85 (1H,d,J=2Hz) 8.39 (1H, d,J=7.5Hz) 8.45 (1H,d, 7.5Hz) 9.43 (1H,s) 9.91 (1H,s) 12.01 (1H,s) |
| Elementary analysis Molecular formula | $C_{24}H_{26}N_2O_7 \cdot H_2O$ | | | |
| Calc. (C, H, N) % Found (C, H, N) % | 61.01, 5.97, 5.93 61.32, 5.68, 5.97 | | | |
| Example No. | 110 | 111 | 112 | |

| R | (D-Ara) | (L-Ara) | | |
|---|---|---|---|---|
| X⁻ | Br | Br | $CH_3CO_2^-$ | |

TABLE 1-continued

| | | |
|---|---|---|
| Crystalline form | Amorphous dark red powder | Amorphous red powder |
| Specific rotatory power [α]D | −820 (λ = 319 nm)<br>−610 (λ = 262 nm)<br>+360 (λ = 230 nm) | +740 (λ = 319 nm)<br>+560 (λ = 256 nm)<br>−580 (λ = 218 nm) | −240° (C = 0.11 1% CF$_3$COOH/H$_2$O) |
| Infrared absorption (KBr, cm$^{-1}$) | 3270, 1600, 1480, 1420, 1290, 1220, 1120, 1060, 820 | 3270, 1600, 1480, 1420, 1290, 1220, 1120, 1060, 820 | 3200, 1635, 1590, 1560, 1470, 1400, 1210, 1190 |
| Ultraviolet absorption (λ$_{max}^{EtOH}$, nm) | 212 (ε24000)<br>251 (ε20000)<br>266 (ε21000)<br>281 (ε19000)<br>322 (ε42000) | 212 (ε24000)<br>261 (ε20000)<br>266 (ε21000)<br>281 (ε19000)<br>322 (ε42000) | 207 (ε20000)<br>226 (ε13000)<br>268 (ε22000)<br>280 (ε20000)<br>324 (ε45000) |
| Mass spectrum (SIMS, m/z) | 395<br>[C$_{22}$H$_{23}$N$_2$O$_5$]$^+$ | 395<br>[C$_{22}$H$_{23}$N$_2$O$_5$]$^+$ | 425<br>[C$_{23}$H$_{25}$O$_6$N$_2$]$^+$ |
| Proton NMR (DMSO-d$_6$, δ in ppm, CD$_2$HSOCD$_3$ proton chemical shift (δ 2.50) was used as internal standard, Intensity of NMR magnetic field was indicated in each compound) | 2.85 (3H,s) 3.30 (3H,s)<br>3.84 (1H,m) 3.95 (1H,m)<br>4.04 (1H,m) 4.16 (1H,m)<br>4.53 (1H,m) 5.69 (2H,m)<br>5.93 (1H,d)<br>6.55 (1H,d,J=6Hz,1'-H)<br>7.17 (1H,dd,J=2,9Hz)<br>7.54 (1H,d,J=9Hz)<br>7.84 (1H,d,J=2Hz)<br>8.46 (1H,d,J=7.5Hz)<br>8.54 (1H,d,J=7.5Hz)<br>9.43 (1H,s) 10.20 (1H,s)<br>11.98 (1H,s) | Same as in left | 1.68 (3H,s) 2.80 (3H,s) 3.24 (3H,s) 5.85 (1H,d,J=8.5Hz 1'-H) 7.16 (1H,dd,J=2.9Hz) 7.53 (1H,d,J=9Hz) 7.82 (1H,d, J=2Hz) 8.36 (1H,d,J=7.5Hz) 8.51 (1H,d,J=7.5Hz) 9.97 (1H,s)<br>(360MHz) |
| Elementary analysis Molecular formula Calc. (C, H, N) % Found (C, H, N) % | | C$_{25}$H$_{28}$N$_2$O$_8$<br>61.97, 5.83, 5.78<br>62.03, 5.73, 5.59 |

TABLE 2

| Example No. | 113 | 114 | 115 |
|---|---|---|---|
| $R^2$ | (sugar structure with OBz, OBz, OBz) | (sugar structure with OBz, OBz, OBz) | (sugar structure with OBz, OBz, OBz) |
| $R^1$ | OAc | OAc | OAc |
| $R^3$ | $CH_3$ | $CH_3$ | $CH_3$ |
| $X^-$ | $Cl^-$ | $Br^-$ | $Br^-$ |
| Crystalline form Specific rotatory $[\alpha]_D$ power | Amorphous orange powder (27° C.) $-71°$ (C=0.14,MeOH) | Amorphous red powder (27° C.) $-196°$ )C=0.15,MeOH) | Amorphous orange powder (27° C.) $+184°$ (C=0.12,MeOH) |
| Infrared absorption (KBr, cm$^{-1}$) | 1730, 1635, 1600, 1590, 1560, 1470, 1400, 1250, 1200, 1090, 701 | 1740, 1645, 1610, 1600, 1595, 1480, 1460, 1410, 1380, 1280, 1210, 1110, 1080, 810 | 1720, 1630, 1580, 1560, 1460, 1390, 1260, 1190, 1090, 800, 705 |
| Ultraviolet absorption ($\lambda_{max}$ EtOH, nm) | 233 ($\epsilon$52000) 320 ($\epsilon$63000) 258 ($\epsilon$26000) 278 ($\epsilon$24000) | 201 ($\epsilon$60000) 278 ($\epsilon$26000) 230 ($\epsilon$59000) 320 ($\epsilon$61000) 258 ($\epsilon$28000) | 201 ($\epsilon$56000) 280 ($\epsilon$28000) 232 ($\epsilon$57000) 319 ($\epsilon$72000) 257 ($\epsilon$31000) |
| Mass spectrum (SIMS, m/z) | 763 [$C_{46}H_{39}N_2O_9$]$^+$ | 763 [$C_{46}H_{39}N_2O_9$]$^+$ | 763 [$C_{46}H_{39}N_2O_9$]$^+$ |
| Proton NMR (DMSO—$d_6$, $\delta$ in ppm, $CD_2HSOCD_3$ proton chemical shift ($\delta$ 2.50) was used as internal standard, Intensity of NMR magnetic field was indicated in each compound) | 2.36 (3H,S) 3.15 (3H,S) 4.31 (3H,S) 4.95 (1H,dd) 5.13 (1H,dd) 5.42 (1H,quintet) 6.10 (1H,dd) 6.14 (1H,S) 7.05 (1H,S,1'-H) 7.32–8.25 (18H,m) 8.68 (1H,d,J=7.5Hz) 8.82 (1H,d,J=7.5Hz) 10.21 (1H,S) (270 MHz) | 2.36 (3H,S) 3.16 (3H,S) 3.24 (3H,S) 4.33 (3H,S) 4.97 (2H,brd) 5.18 (1H,q,J=5Hz) 6.11 (1H,t,J=5Hz) 6.20 (1H,t,J=5Hz) 7.05 (1H,d,J=5Hz,1'-H) 7.44–8.03 (17H,m) 8.24 (1H,d,J=2Hz) 8.65 (1H,d,J=8Hz) 8.77 (1H,d,J=8Hz) 10.26 (1H,S) (270 MHz) | 2.36 (3H,S) 3.20 (3H,S) 3.28 (3H,S) 4.34 (3H,S) 4.86 (2H,m) 5.74 (1H,m) 6.01 (1H,t) 6.25 (1H,t) 7.21 (1H,d,J=1.5Hz,1'-H) 7.30–8.15 (17H,m) 8.26 (1H,d,J=2Hz) 8.72 (1H,d,J=7.5Hz) 8.83 (1H,d,J=7.5Hz) 10.16 (1H,S) (360) MHz) |

Elementary analysis

| | 113 | 114 | 115 |
|---|---|---|---|
| Molecular formula | $C_{46}H_{39}N_2O_9Cl\cdot3H_2O$ | Same as in the left | — |
| Calc. (C, H, N) % | 64.75, 5.32, 3.28 | | |
| Found (C, H, N) % | 64.51, 5.21, 3.35 | | |

| Example No. | 116 | 117 | 118 |
|---|---|---|---|
| $R^2$ | (sugar structure with OBz, OBz, $CH_3$) | (sugar structure with OBz, OBz) | (sugar structure with OBz, OBz, $CH_3$) |
| $R^1$ | OAc | OAc | OAc |
| $R^3$ | $CH_3$ | $CH_3$ | $CH_3$ |
| $X^-$ | $Br^-$ | $Cl$ | $Cl^-$ |
| Crystalline form Specific rotatory $[\alpha]_D$ | Amorphous orange powder (28° C.) $-298°$ (C=0.10,MeOH) | Amorphous orange powder $-224°$ (C=0.16, CH$_3$OH) | Amorphous red powder $-105°$ (C=0.11, CH$_3$OH) |
| Molecular formula | $C_{46}H_{39}N_2O_9Cl\cdot3H_2O$ | $C_{46}H_{39}N_2O_9Br\cdot1.5H_2O$ | $C_{46}H_{39}N_2O_9Br\cdot1.5H_2O$ |
| Calc. (C, H, N) % | 64.75, 5.32, 3.28 | 63.45, 4.86, 3.22 | 63.45, 4.86, 3.22 |
| Found (C, H, N) % | 64.59, 5.35, 3.29 | 63.62, 4.73, 3.23 | 63.51, 4.92, 3.25 |

TABLE 2-continued

| power Infrared absorption (KBr, cm⁻¹) | 1720, 1630, 1580, 1560, 1460, 1390, 1260, 1190, 1090, 800, 705 | 1725, 1630, 1580, 1560, 1470, 1395, 1250, 1200, 1100, 920, 800, 710 | 1730, 1630, 1585, 1560, 1470, 1395, 1310, 1275, 1200, 1090 | 1730, 1630, 1600, 1580, 1470, 1450, 1400, 1385, 1370, 1270, 1210, 1120, 1100 |
|---|---|---|---|---|
| Ultraviolet absorption ($\lambda_{max}^{EtOH}$, nm) | 201 (ε56000) 280 (ε28000) 232 (ε57000) 319 (ε72000) 257 (ε31000) | 201 (ε38000) 280 (ε22000) 232 (ε40000) 318 (ε59000) 257 (ε25000) | 201 (ε42000) 280 (ε24000) 230 (ε38000) 319 (ε61000) 258 (ε27000) | 201 (ε41000), 280 (ε24000) 231 (ε40000) 319 (ε61000) 258 (ε36000) |
| Mass spectrum (SIMS, m/z) | 763 | 643 | 629⁺ | 643 |
| Proton NMR (DMSO—d₆, δ in ppm, CD₂HSOCD₃ proton chemical shift (δ 2.50 was used as internal standard, Intensity of NMR magnetic field was indicated in each compound) | [C₄₆H₃₉N₂O₉]⁺ 2.36 (3H,S) 3.20 (3H,S) 3.28 (3H,S) 4.34 (3H,S) 4.86 (2H,m) 5.74 (1H,m) 6.01 (1H,t) 6.25 (1H,S) 7.21 (1H,d,J = 1.5Hz,1'-H) 7.30–8.15 (17H,m) 8.26 (1H,d,J = 2Hz) 8.72 (1H,d,J = 7.5Hz) 8.83 (1H,d,J = 7.5Hz) 10.16 (1H,S) (360 MHz) | [C₃₉H₃₅N₂O₉]⁺ 1.68 (3H,d,J = 6.5Hz) 2.36 (3H,S) 3.18 (3H,S) 3.23 (3H, S) 4.33 (3H,S) 5.43 (1H,q) 5.60 (1H,S) 6.12 (1H,S) 7.16 (1H,S,1'-H) 7.19–8.16 (12H,m) 8.23 (1H,d,J = 2Hz) 8.70 (1H,d,J = 7.9Hz) 8.75 (1H,d,J = 7.9Hz) 10.08 (1H,S) (270 MHz) | [C₃₈H₃₃N₂O₇]⁺ 2.36 (3H,S) 3.15 (3H,S) 3.26 (3H,S) 4.28 (3H,S) 4.60 (1H,d,J = 10.6Hz) 5.22 (1H,dd,J = 3.3,10.6Hz) 6.08 (1H,t) 6.29 (1H,t, J = 5Hz) 7.02 (1H,d,J = 6Hz) 7.39–8.10 (12H,m) 8.23 (1H,d,J = 2Hz) 8.70 (1H,d,J = 7.5Hz) 8.85 (1H,d,J = 7.5Hz) 10.30 (1H,S) | [C₃₉H₃₅N₂O₇]⁺ Same as in the left |
| Elementary analysis Molecular formula Calc. (C, H, N) % Found (C, H, N) % | — | — | C₃₈H₃₃N₂O₇Cl·2.5H₂O 64.27, 5.39, 3.94 64.49, 5.10, 4.08 | C₃₈H₃₃N₂O₇Cl·2.5H₂O 64.27, 5.39, 3.94 64.15, 5.40, 3.98 |

| Example No. | 119 | 119 | 120 | 120 | 121 |
|---|---|---|---|---|---|
| R² | (structure with OBn groups) | (structure with OBn groups) | (structure with OH groups) | (structure with OH groups) | (structure with OH groups) |
| R¹ R³ X⁻ | OAc CH₃ Br⁻ | OAc CH₃ Br⁻ | OH CH₃ Cl⁻ | OH CH₃ Cl⁻ | OH CH₃ Br⁻ |
| Crystalline form Specific rotatory [α]_D power | Amorphous orange powder +35° (C=0.11, CH₃OH) | Amorphous orange powder −34° (C=0.12, CH₃OH) | Amorphous orange powder (28° C.) +175° (C=0.05, DMSO) | Amorphous orange powder (28° C.) −168° (C=0.07, DMSO) | Amorphous orange powder (28° C.) −118° (C=0.5, DMSO) |
| Infrared absorption (KBr, cm⁻¹) | 1755, 1630, 1580, 1465, 1390 1370, 1290, 1250, 1200, 1090 | 1755, 1630, 1580, 1465, 1390 1370, 1290, 1250, 1200, 1090 | 3250, 2930, 1640, 1585, 1560, 1470, 1395, 1290, 1220, 1100, 1050, 900, 810, 750 | 3250, 2930, 1640, 1585, 1560, 1470, 1395, 1290, 1220, 1100, 1050, 900, 810, 750 | 1640, 1580, 1480, 1450, 1400, 1290, 1245, 1220, 1150, 1110, 1090, 1040, 900, 860, 810, 800, 3250 |
| Ultraviolet absorption ($\lambda_{max}^{EtOH}$, nm) | 206 (ε40000) 318 (ε62000) 257 (ε25000) 280 (ε21000) | 206 (ε40000) 318 (ε62000) 257 (ε25000) 280 (ε21000) | 211 (ε24000) 284 (ε26000) 227 (ε17000) 327 (ε49000) 220 (ε29000) | 211 (ε24000) 284 (ε26000) 227 (ε17000) 327 (ε49000) 220 (ε29000) | 210 (ε24000) 284 (ε25000) 227 (ε17000) 327 (ε51000) 270 (ε30000) |
| Mass spectrum (SIMS, m/z) | 721 [C₄₆H₄₅N₂O₆]⁺ | 721 [C₄₆H₄₅N₂O₆]⁺ Same as in the left | 409 [C₂₃H₂₅N₂O₅]⁺ | 409 [C₂₃H₂₅N₂O₅]⁺ Same as in the right | 409 [C₂₃H₂₅N₂O₅]⁺ |
| Proton NMR (DMSO—d₆, δ in ppm, CD₂HSOCD₃ proton chemical shift (δ 2.50 | 2.37 (3H,S) 3.11 (3H,S) 3.17 (3H,S) 3.91 (2H,m) 4.30 (3H,S) 4.34–4.79 (10H,m) 6.85 (3H,m) | | 3.05 (3H,S) 3.18 (3H,S) 4.17 (3H,S) 3.97 (2H,m), 4.17 (1H,S) 4.34 (1H,S) 4.49 (1H,q), 5.11 (1H,t,J = 3.5Hz) 5.73 (1H,S) | | 3.11 (3H,S) 3.24 (3H,S) 3.81 (1H,brd,J = 12Hz) 3.91 (1H,brd,J = 12Hz) 4.23 (3H,S) 4.23–4.29 (2H,m) |

TABLE 2-continued

| | | | | | |
|---|---|---|---|---|---|
| was used as internal standard, Intensity of NMR magnetic field was indicated in each compound) | 7.03 (3H,m) 7.36–7.41 (9H,m) 7.53 (1H,dd,J=2,9Hz) 7.87 (1H,d,J=9Hz) 8.23 (1H,d,J=2Hz) 8.34 (1H,d,J=7.5Hz) 8.62 (1H,d,J=7.5Hz) 10.06 (1H,S) | | 6.37 (1H,d,J=3Hz) 6.33 (1H,S,1'-H) 7.20 (1H,dd, J=2,9Hz) 7.59 (1H,d,J=9Hz) 7.81 (1H,d,J=2Hz) 8.55 (1H,d, J=7.5Hz) 8.63 (1H,d,J=7.5Hz) 9.53 (1H,S) 10.10 (1H,S) | | 4.34 (1H,m) 5.49 (1H,brs) 5.64 (1H,brs) 5.90 (1H,brs) 6.28 (1H,d,J=4.5Hz,1'-H) 7.22 (1H,dd,J=2Hz,9Hz) 7.64 (1H,d,J=9Hz) 7.84 (1H,d, J=2Hz) 8.61 (1H,d,J=7Hz) (1H,brs) 10.25 (1H,S) [360 MHz] |
| Elementary analysis Molecular formula Calc. (C, H, N) % Found (C, H, N) % | — | | $C_{23}H_{25}N_2O_5Cl\cdot H_2O$ 59.68, 5.88, 6.05 59.52, 5.81, 6.09 | | $C_{23}H_{25}N_2O_5Br$ 56.45, 5.15, 5.72 56.26, 5.12, 5.67 |

| Example No. | 121 | 122 | 123 | 124 |
|---|---|---|---|---|
| $R^2$ | [structure with OH, OH, O ring] | [structure with OH, OH, O ring] | [structure with OH, CH$_3$, O ring] | [structure with OH, OH, O ring] |
| $R^1$ $R^3$ $X^-$ | OH CH$_3$ Br$^-$ | OH CH$_3$ Br$^-$ | OH CH$_3$ Cl$^-$ | OH CH$_3$ Cl$^-$ |
| Crystalline form Specific rotatory $[\alpha]_D$ power | Amorphous orange powder (28° C.) +123° (C=0.06, DMSO) | Amorphous orange powder (28° C.) +48° (C=0.08, DMSO) | Amorphous orange powder (28° C.) −44° (C=0.8, DMSO) | Amorphous orange powder (28° C.) −49° (C=0.6, DMSO) | Amorphous orange powder +100° (C=0.02, DMSO) |
| Infrared absorption (KBr, cm$^{-1}$) | 1640, 1580, 1480, 1450, 1400, 1290, 1245, 1220, 1150, 1110, 1090, 1040, 900, 860, 810, 800, 3250 | 3250, 1630, 1580, 1560, 1470, 1390, 1220, 1090, 1060, 1040, 895, 795, 740 | 3250, 1630, 1580, 1560, 1470, 1390, 1220, 1090, 1060, 1040, 895, 795, 740 | 3250, 1630, 1585, 1560, 1475, 1400, 1230, 1100, 1050, 900, 800, 750 | 3300, 1630, 1580, 1560, 1465, 1400, 1380, 1220, 1085, 1045 |
| Ultraviolet absorption ($\lambda_{max}^{EtOH}$, nm) | 210 (ε24000) 284 (ε25000) 227 (ε17000) 327 (ε51000) 270 (ε30000) | 210 (ε24000) 284 (ε25000) 227 (ε17000) 327 (ε49000) 270 (ε29000) | 210 (ε24000) 284 (ε25000) 227 (ε17000) 327 (ε49000) 270 (ε29000) | 211 (ε20000) 283 (ε21000) 228 (ε14000) 327 (ε42000) 270 (ε25000) | 210 (ε23000) 284 (ε24000) 227 (ε16000) 328 (ε45000) 270 (ε29000) |
| Mass spectrum (SIMS, m/z) | 409 [$C_{23}H_{25}N_2O_5$]$^+$ | 409 [$C_{23}H_{25}N_2O_5$]$^+$ | 409 Same as in the left [$C_{23}H_{25}N_2O_5$]$^+$ | 393 [$C_{23}H_{23}N_2O_4$]$^+$ | 379 [$C_{22}H_{23}N_2O_4$]$^+$ |
| Proton NMR (DMSO—d$_6$, δ in ppm, CD$_2$HSOCD$_3$ proton chemical shift (δ 2.50 was used as internal standard, Intensity of NMR magnetic field was indicated in each compound) | 3.11 (3H,S) 3.24 (3H,S) 3.81 (1H,brd,J=12Hz) 3.91 (1H,brd,J=12Hz) 4.23 (3H,S) 4.23–4.29 (2H,m) 4.34 (1H,m) 5.49 (1H,brs) 5.64 (1H,brs) 5.90 (1H,brs) 6.28 (1H,d,J=4.5Hz,1'-H) 7.22 (1H,dd,J=2Hz,9Hz) 7.64 (1H,d,J=9Hz) 7.84 (1H,d, J=2Hz) 8.61 (1H,d,J=7Hz) 9.56 (1H,brs) 10.25 (1H,S) [360 MHz] | 3.12 (3H,S) 3.27 (3H,S) 3.70 (2H,m) 4.16 (1H,q) 4.37 (1H,q) 4.59 (1H,q) 4.23 (3H,S) 5.20 (1H,t) 5.69 (1H,d) 6.18 (1H,d) 6.37 (1H,d,J=3Hz,1'-H) 7.22 (1H,dd,J=2,9Hz) 7.65 (1H,d J=9Hz) 7.87 (1H,d,J=2Hz) 8.58 (2H,S) 9.53 (1H,S) 9.97 (1H,S) (360 MHz) | 1.44 (3H,d,J=6.5Hz) 3.10 (3H,S) 3.25 (3H,S) 3.92 (1H,t) 4.20 (3H,S) 4.36 (1H,brs) 4.72 (1H,m) 5.73 (1H,d) 6.35 (1H,brs) 6.42 (1H,d,J=2.5Hz,1'-H) 7.22 (1H,dd,J=2,9Hz) 7.63 (1H,d,J=9Hz) 7.86 (1H,d, J=2Hz) 8.57 (2H,S) 9.58 (1H,brs) 9.98 (1H,S) (360 MHz) | 3.12 (3H,S) 3.26 (3H,S) 4.09 (1H,d) 4.28 (1H,m) 4.45 (1H,m) 4.72 (1H,dd) 4.23 (3H,S) 5.58 (1H,d) 5.93 (1H,d) 6.27 (1H,dd,J=2,9Hz) 7.23 (1H,d,J=9Hz) 7.65 (1H,dd,J=2.9Hz,1'-H) 7.87 (1H,d,J=2Hz) 8.54 (1H,d,J=7.5Hz) 8.58 (1H,d,J=7.5Hz) 9.58 (1H,S) 10.01 (1H,S) |
| Elementary analysis Molecular formula Calc. (C, H, N) % Found (C, H, N) % | $C_{23}H_{25}N_2O_5Br$ 56.45, 5.15, 5.72 56.53, 5.21, 5.68 | $C_{23}H_{25}N_2O_5Br\cdot H_2O$ 54.44, 5.36, 5.52 54.35, 4.98, 5.38 | $C_{23}H_{25}N_2O_5Br\cdot H_2O$ 54.44, 5.36, 5.52 54.46, 5.21, 5.63 | — |

TABLE 2-continued

| Example No. | 124 | 125 | 126 | 127 |
|---|---|---|---|---|
| R[2] | (structure with OH, OH, OBz groups on furanose ring) | (structure with OH, OH, CH₃ groups on furanose ring) | (structure with OH, OH, OH groups on furanose ring) | (structure with OBz, OBz, OBz groups on furanose ring) |
| R[1] | OH | OH | OH | OAc |
| R[3] | CH₃ | CH₃ | CH₃ | CH₃ |
| X[−] | Cl[−] | Cl[−] | Br[−] | Cl[−] |
| Crystalline form | Amorphous orange powder | Amorphous red powder | Amorphous dark red powder Poor permeability | Amorphous reddish orange powder |
| Specific rotatory $[\alpha]_D$ power | −98° (C=0.03, DMSO) | −40° (C=0.04, DMSO) | Not determinable | +176° (C=0.14, MeOH) (28°) |
| Infrared absorption (KBr, cm⁻¹) | 3300, 1630, 1580, 1560, 1465 1400, 1380, 1220, 1085, 1045 800 | 3200, 1630, 1585, 1560, 1470 1450, 1395, 1220, 1090, 1020 | 3350, 1630, 1590, 1560, 1470 1400, 1290, 1065, 800 | 1730, 1630, 1595, 1585, 1470 1450, 1395, 1270, 1200, 1090, 705 |
| Ultraviolet absorption ($\lambda_{max}^{EtOH}$, nm) | 210 (ε23000) 284 (ε24000) 227 (ε16000) 328 (ε45000) 270 (ε29000) | 212 (ε20000) 286 (ε21000) 228 (ε15000) 328 (ε42000) 272 (ε25000) | 215 (ε25000) 283 (ε22000) 324 (ε24000) | 201 (ε48000) 278 (ε26000) 230 (ε53000) 319 (ε65000) 257 (ε28000) |
| Mass spectrum (SIMS, m/z) | 379 | 393 | 409 | 763 |
| Proton NMR (DMSO-d₆, δ in ppm, CD₂HSOCD₃ proton chemical shift (δ 2.50) was used as internal standard, Intensity of NMR magnetic field was indicated in each compound) | [C₂₂H₂₃N₂O₄]⁺ 3.12 (3H,S) 3.26 (3H,S) 4.09 (1H,d) 4.28 (1H,m) 4.45 (1H,m) 4.72 (1H,dd) 4.23 (3H,S) 5.58 (1H,d) 5.93 (1H,d) 6.27 (1H,d,J=7Hz, 1'-H) 7.23 (1H,dd,J=2.9Hz, 7.65 (1H,d,J=9Hz) 7.87 (1H, d,J=2Hz) 8.54 (1H,d,J=7.5Hz) 8.58 (1H,d,J=7.5Hz) 9.58 (1H,S) 10.01 (1H,S) | [C₂₃H₂₅N₂O₄]⁺ 1.53 (3H,d,J=6.5Hz) 3.11 (3H,S) 3.25 (3H,S) 3.96 (1H,q,J=4Hz) 4.33 (1H,dq, J=4,6.5Hz) 4.40 (1H,m) 5.52 (1H,d,J=4Hz) 5.94 (1H,m) 6.28 (1H,d,J=5Hz,1'-H) 7.22 (1H,dd,J=2.9Hz) 7.54 (1H,d,J=9Hz) 7.76 (1H,d, J=2Hz) 8.43 (1H,d,J=7.5Hz) 8.58 (1H,d,J=7.5Hz) 9.60 (1HbrS) 9.98 (1H,S) | [C₂₃H₂₅N₂O₅]⁺ 3.13 (3H,S) 3.84 (1H,m) 3.96 (1H,m) 4.04 (1H,m) 4.16 (1H,m) 4.53 (1H,m) 4.24 (3H,S) 5.70 (2H,d) 5.95 (1H,d), 6.56 (1H,d, J=6Hz,1'-H) 7.23 (1H,dd, J=2.9Hz) 7.66 (1H,d,J=9Hz) 7.87 (1H,d,J=2Hz) 8.56 (2H,ABq) 9.52 (1H,S), 10.22 (1H,S) | [C₄₆H₃₉N₂O₉]⁺ α-Form 2.36 (3H,S) 3.18 (3H,S) 4.33 (3H,S) 4.82 (2H,m) 5.80 (1H,m) 6.27 (1H,t) 6.42 (1H,dd) 7.36–8.11 (17H,m) 7.87 (1H,d,J=9Hz) 8.26 (1H,d,J=2Hz) 8.75 (1H,1'-H) 7.23 (1H,dd, d,J=7.5Hz) 8.93 (1H, d,J=7.5Hz) 10.33 (1H,S) β-Form 2.34 (3H,S) 3.04 (3H,S) 5.01 (1H,dd) 5.25 (1H,dd) 5.36 (1H,m) 6.09 (1H,dd) 6.51 (1H,dd) 7.10–8.05 (18H,m) 8.18 (1H,d,J=2Hz) 8.64 (1H,d,J=7.5Hz) 8.98 (1H,d, J=7.5Hz) 10.23 (1H,S) |

Elementary analysis

| Molecular formula | | | | C₄₆H₃₉N₂O₉Cl.2H₂O |
|---|---|---|---|---|
| Calc. (C, H, N) % | | | | 66.14, 5.19, 3.35 |
| Found (C, H, N) % | | | | 65.90, 4.88, 3.48 |

| Example No. | 128 | 129 | 130 | 131 | 132 |
|---|---|---|---|---|---|
| R[2] | (structure with OBz, OBz, OBz groups on furanose ring) | (structure with OH, OH, OH groups on furanose ring) | (structure with OH, OH, OH groups on furanose ring) | (structure with OAc, OAc, OAc groups on pyranose ring) | (structure with OAc, OAc, OAc groups on pyranose ring) |
| R[1] | OAc | OH | OH | OAc | OAc |
| R[3] | CH₃ | CH₃ | CH₃ | CH₃ | CH₃ |

TABLE 2-continued

| | | | | | | |
|---|---|---|---|---|---|---|
| X⁻ | Cl⁻ | Cl⁻ | Cl⁻ | Br⁻ | Br⁻ | |
| Crystalline form | Amorphous reddish orange powder | Amorphous reddish orange powder | Amorphous orange powder | Amorphous red powder | Amorphous red powder | |
| Specific rotatory [α]_D power | −168° (C=0.11, MeOH) (28° C.) | −17° (C=0.06, DMSO) (28° C.) | +16° (C=0.04, DMSO) (28° C.) | +3° (C=0.11, MeOH) (27° C.) | −3° (C=0.11, MeOH) (27° C.) | |
| Infrared absorption (KBr, cm⁻¹) | 1730, 1650, 1595, 1585, 1470, 3250, 1630, 1595, 1560, 1470, 1450, 1395, 1270, 1200, 1090, 705 | 3250, 1630, 1595, 1560, 1470, 1440, 1400, 1220, 1140, 1100, 1050, 805, 750 | 1750, 1635, 1590, 1480, 1470, 1440, 1400, 1220, 1140, 1100, 1050, 805, 750 | 1750, 1635, 1590, 1480, 1470, 1400, 1370, 1295, 1200, 1100, 1070, 1040, 940, 890, 810 | 1400, 1370, 1295, 1210, 1100, 1070, 1040, 940, 890, 810 | |
| Ultraviolet absorption (λ_max^EtOH, nm) | 201 (ε48000) 270 (ε26000) 230 (ε53000) 319 (ε65000) 257 (ε28000) | 211 (ε28000) 284 (ε30000) 227 (ε20000) 328 (ε58000) 270 (ε35000) | 211 (ε28000) 284 (ε30000) 227 (ε20000) 328 (ε58000) 270 (ε35000) | 209 (ε20000) 283 (ε21000) 245 (ε21000) 320 (ε54000) 258 (ε23000) | 209 (ε20000) 284 (ε21000) 245 (ε21000) 320 (ε54000) 258 (ε23000) | |
| Mass spectrum (SIMS, m/z) | 763 | 409 | 409 | 577 | 577 | |
| Proton NMR (DMSO-d₆, δ in ppm, CD₂HSOCD₃ proton chemical shift (δ 2.50) was used as internal standard, Intensity of NMR magnetic field was indicated in each compound) | [C₄₆H₃₉N₂O₉]⁺ α-Form 2.36 (3H,S) 3.18 (3H,S) 4.33 (3H,S) 4.82 (2H,m) 5.80 (1H,m) 6.27 (1H,t) 6.42 (1H,dd) 7.36–8.11 (17H,m) 7.87 (1H,d,J=9Hz) 8.26 (1H,d,J=2Hz) 8.75 (1H,d,J=7.5Hz) 8.93 (1H, d,J=7.5Hz) 10.33 (1H,S) β-Form 2.34 (3H,S) 3.04 (3H,S) 5.01 (1H,dd) 5.25 (1H,dd) 5.36 (1H,m) 6.09 (1H,dd) 6.51 (1H,dd,J=2Hz) 7.10–8.05 (18H,m) 8.18 (1H,d,J=2Hz) 8.64 (1H,d,J=7.5Hz) 8.98 (1H,S) (1H,d,J=7.5Hz) 10.23 (1H,S) | [C₂₃H₂₅N₂O₅]⁺ α-Form 3.08 (3H,S) 3.23 (3H,S) 3.69 (1H,m) 3.80 (1H,m) 4.19 (3H,s) 4.23 (1H,m) 4.55 (1H,m) 4.80 (1H,m) 4.91 (1H,t) 5.58 (1H,d) 5.96 (1H,d) 6.28 (1H,d,J=7Hz,1′-H) 7.22 (1H,dd, J=2.9Hz) 7.62 (1H,d,J=9Hz) 7.84 (1H,d,J=2Hz) 8.56 (2H,ABq) 9.59 (1H,S) 9.98 (1H,S) β-Form 3.05 (3H,S) 3.18 (3H,S) 3.95 (1H,m) 4.02 (1H,m) 4.31 (1H,m) 4.74 (1H,m) 5.10 (1H,t) 5.51 (1H,d) 6.44 (1H,d, J=6.5Hz,1′1′-H) 7.19 (1H,dd, J=2.9Hz) 8.48 (2H,ABq) 9.56 (1H,S) | [C₂₃H₂₅N₂O₅]⁺ α-Form 3.08 (3H,S) 3.23 (3H,S) 3.69 (1H,m) 3.80 (1H,m) 4.19 (3H,S) 4.23 (1H,m) 4.55 (1H,m) 4.80 (1H,m) 4.91 (1H,t) 5.58 (1H,d) 5.96 (1H,d) 6.28 (1H,d,J=7Hz,1′-H) 7.22 (1H,dd, J=2.9Hz) 7.62 (1H,d,J=9Hz) 7.84 (1H,d,J=2Hz) 8.56 (2H,ABq) 9.59 (1H,S) 9.98 (1H,S) β-Form 3.05 (3H,S) 3.95 (1H,m) 4.02 (1H,m) 4.31 (1H,m) 4.74 (1H,m) 5.10 (1H,t) 5.51 (1H,d) 6.44 (1H,d, J=6.5Hz,1′-H) 7.19 (1H,dd, J=2.9Hz) 8.48 (2H,ABq) 9.56 (1H,S) | [C₃₁H₃₃N₂O₉]⁺ 1.77, 2.05, 2.29, (each 3H, S) 2.37 (3H,S) 3.17 (3H,S) 4.06 (1H,m) 4.28 (1H,m) 4.33 (3H,S) 5.54 (1H,m) 5.78 (1H,d,J=2Hz) 5.92 (1H,dd,J=2Hz,7Hz) 6.48 (1H,d,J=7Hz,1′-H) 7.56 (1H,dd,J=2Hz,9Hz) 7.91 (1H,d,J=9Hz) 8.31 (1H,d,J=2Hz) 8.70 (1H,d,J=6.5Hz) 8.79 (1H,d,J=6.5Hz) 10.29 (1H,S) 270 MHz | [C₃₁H₃₃N₂O₉]⁺ 1.77, 2.05, 2.29, (each 3H,S) 2.37 (3H,S) 3.17 (3H,S) 4.06 (1H,m) 4.28 (1H,m) 4.33 (3H,S) 5.54 (1H,m) 5.78 (1H,d,J=2Hz) 5.92 (1H,dd,J=2Hz,7Hz) 6.48 (1H,d,J=7Hz,1′-H) 7.56 (1H,dd,J=2Hz,9Hz) 7.91 (1H,d,J=9Hz) 8.31 (1H,d,J=2Hz) 8.70 (1H,d,J=6.5Hz) 8.79 (1H,d,J=6.5Hz) 10.29 (1H,S) 270 MHz | |

| Elementary analysis | | | | | |
|---|---|---|---|---|---|
| Molecular formula | C₄₉H₃₉N₂O₉Cl.2H₂O | C₂₃H₂₅N₂O₅Cl.1.5H₂O | C₂₃H₂₅N₂O₅Cl.1.5H₂O | C₃₁H₃₃N₂O₉Br.3H₂O | C₃₁H₃₃N₂O₉Br.3H₂O |
| Calc. (C, H, N) % | 66.14, 5.19, 3.35 | 58.54, 5.98, 5.94 | 58.54, 5.98, 5.94 | 52.33, 5.52, 3.94 | 52.33, 5.52, 3.94 |
| Found (C, H, N) % | 66.05, 5.03, 3.27 | 58.49, 5.76, 6.00 | 58.62, 5.82, 5.95 | 52.07, 5.41, 3.73 | 52.32, 5.65, 4.01 |
| Example No. | 133 | 134 | 135 | 136 | 137 |

| R² | R¹ | R³ | X⁻ | Crystalline form | Specific rotatory [α]_D power |
|---|---|---|---|---|---|
| (sugar structures shown) | OAc | CH₃ | Br⁻ | Amorphous reddish orange powder (27° C.) | −14° (C=0.14, MeOH) |
| | OAc | CH₃ | Br⁻ | Amorphous reddish orange powder (27° C.) | +11° (C=0.23, MeOH) |
| | OAc | CH₃ | Br⁻ | Amorphous red powder (27° C.) | −23° (C=0.11, MeOH) |
| | OAc | CH₃ | Br⁻ | Amorphous orange powder (27° C.) | +24° (C=0.11, MeOH) |
| | OAc | CH₃ | Cl⁻ | Amorphous reddish orange powder (27° C.) | −75° (C=0.10, MeOH) |

TABLE 2-continued

| Infrared absorption (KBr, cm⁻¹) | 1750, 1630, 1580, 1460, 1390, 1360, 1240, 1210, 1070, 1050, 920, 810 | 1750, 1630, 1580, 1560, 1465, 1750, 1630, 1580, 1560, 1465, 1370, 1210, 1045, 930, 810, 750 | 1750, 1630, 1580, 1560, 1460, 1370, 1210, 1045, 930, 810, 750 | 1750, 1630, 1580, 1560, 1460, 1390, 1365, 1210, 1050, 940, 810, 750 |
|---|---|---|---|---|
| Ultraviolet absorption ($\lambda_{max}^{EtOH}$, nm) | 210 ($\varepsilon$18000) 282 ($\varepsilon$17000) 245 ($\varepsilon$16000) 321 ($\varepsilon$44000) 259 ($\varepsilon$19000) | 211 ($\varepsilon$18000) 282 ($\varepsilon$22000) 244 ($\varepsilon$21000) 321 ($\varepsilon$57000) 260 ($\varepsilon$25000) | 209 ($\varepsilon$18000) 282 ($\varepsilon$21000) 245 ($\varepsilon$20000) 321 ($\varepsilon$54000) 260 ($\varepsilon$24000) | 209 ($\varepsilon$20000) 200 ($\varepsilon$22000) 245 ($\varepsilon$22000) 320 ($\varepsilon$56000) 258 ($\varepsilon$24000) |
| Mass spectrum (SIMS, m/z) | 591 | 577 | 577 | 577 |
| Proton NMR (DMSO—$d_6$, $\delta$ in ppm, CD$_3$HSOCD$_3$ proton chemical shift ($\delta$ 2.50) was used as internal standard, Intensity of NMR magnetic field was indicated in each compound) | [C$_{32}$H$_{35}$N$_2$O$_9$]⁺ 1.26 (3H,d,J=6.5Hz) 1.79 1.99 2.30 (each 3H,S) 2.36 (3H,S) 3.17 (3H,S) 4.34 (3H,S) 4.56 (1H,m) 5.39–5.54 (3H,m) 6.42 (1H,d,J=9Hz,1'-H) 7.55 (1H,dd,J=2Hz,9Hz) 7.92 (1H,d,J=9Hz) 8.31 (1H,S) 8.56 (1H,d,J=7.5Hz) 8.67 (1H,d,J=7.5Hz) 10.17 (1H,S) (270 MHz) | [C$_{31}$H$_{33}$N$_2$O$_9$]⁺ 1.79, 2.00, 2.27 (each 3H,S) 2.36 (3H,S) 3.16 (3H,S) 4.32 (3H,S) 4.34 (2H,m) 5.44 (1H,S) 5.51 (2H, AB portion of ABX J$_{2,3}$=10Hz,J$_{1',3'}$=4Hz) 6.37 (1H, X portion of ABX, J$_{1',2'}$=8Hz,1'-H) 7.55 (1H, dd,J=2, 9Hz) 7.90 (1H,d, J=9Hz) 8.30 (1H,d,J=2Hz) 8.58 (1H,d,J=7.5Hz) 8.67 (1H,d,J=7.5Hz) 10.17 (1H,S) (360 MHz) | [C$_{31}$H$_{33}$N$_2$O$_9$]⁺ 1.79, 2.00, 2.27 (each 3H,S) 2.36 (3H,S) 3.16 (3H,S) 4.32 (3H,S) 4.34 (2H,m) 5.05 (1H,d) 5.53 (2H,m) 6.59 (1H,d,J=9Hz,1'-H) 7.55 (1H,dd,J=2,9Hz) 7.90 (1H,d,J=9Hz) 8.29 (1H,d,J=2Hz) 8.65 (2H,S) 10.29 (1H,S) (270 MHz) | [C$_{31}$H$_{33}$N$_2$O$_9$]⁺ 1.76, 2.26, 2.28 (each 3H,S) 2.37 (3H,S) 3.16 (3H,S) 4.30 (2H,S) 4.32 (3H,S) 5.05 (1H,d) 5.53 (2H,m) 6.59 (1H,d,J=9Hz,1'-H) 7.55 (1H,dd,J=2.9Hz) 7.90 (1H,d,J=9Hz) 8.29 (1H,d,J=2Hz) 8.65 (2H,S) 10.29 (1H,S) (270 MHz) |

| Elementary analysis | | | | |
|---|---|---|---|---|
| Molecular formula Calc. (C, H, N) % Found (C, H, N) % | — | — | — | C$_{31}$H$_{33}$N$_2$O$_9$Cl.4H$_2$O 54.35, 6.03, 4.09 54.08, 5.95, 4.12 |

| Example No. | 138 | 139 | 139 | 140 |
|---|---|---|---|---|
| R² | OAc structures | OAc structures | OAc structures | OAc structures |
| R¹ | OAc | OAc | OAc | OAc |
| R³ | CH₃ | CH₃ | CH₃ | CH₃ |
| X⁻ | Cl⁻ | Br⁻ | Br⁻ | Br⁻ |
| Crystalline form | Amorphous reddish orange powder | Amorphous reddish orange powder | Amorphous reddish orange powder | Amorphous reddish orange powder |
| Specific rotatory [$\alpha$]$_D$ power | (28° C.) +89° (C=0.10, MeOH) | (27° C.) −1° (C=0.11, MeOH) | (27° C.) +1° (C=0.13, MeOH) | (27° C.) −87° (C=0.13, CH$_3$OH) | (27° C.) +90° (C=0.11, CH$_3$OH) |
| Infrared absorption (KBr, cm⁻¹) | 1750, 1630, 1580, 1560, 1460, 1390, 1365, 1210, 1050, 940, 810, 750 | 1755, 1630, 1585, 1560, 1470, 1400, 1370, 1290, 1210, 1050, 920, 910, 810 | 1755, 1630, 1585, 1560, 1470, 1400, 1370, 1290, 1210, 1050, 930, 910, 810 | 1760, 1630, 1585, 1560, 1480, 1470, 1440, 1390, 1370, 1290, 1210, 1140, 1100, 1040 |
| Ultraviolet absorption ($\lambda_{max}^{EtOH}$, nm) | 210 ($\varepsilon$20000) 282 ($\varepsilon$20000) 244 ($\varepsilon$20000) 320 ($\varepsilon$50000) 258 ($\varepsilon$22000) | 210 ($\varepsilon$20000) 283 ($\varepsilon$22000) 247 ($\varepsilon$22000) 322 ($\varepsilon$57000) 260 ($\varepsilon$25000) | 210 ($\varepsilon$20000) 280 ($\varepsilon$23000) 245 ($\varepsilon$23000) 322 ($\varepsilon$59000) 258 ($\varepsilon$26000) | 210 ($\varepsilon$20000) 280 ($\varepsilon$23000) 245 ($\varepsilon$23000) 322 ($\varepsilon$59000) 258 ($\varepsilon$26000) |
| Mass spectrum | 577 | 649 | 649 | 649 |

TABLE 2-continued

| Example No. | 141 | 142 | 143 | 144 | 145 |
|---|---|---|---|---|---|
| R² | AcHN, OAc, ⫽OAc, OAc (structure) | OAc, ⫽OAc, OAc, CO₂CH₃ (structure) | OAc, OAc, ⫽OAc, OAc (structure) | OAc, OAc, ⫽OAc, OAc (structure) | OH, OH, ⫽OH, OH (structure) |
| R¹ | OAc | OAc | OAc | OAc | OH |
| R³ | CH₃ | CH₃ | CH₃ | CH₃ | CH₃ |
| X⁻ | Cl⁻ | Br⁻ | Br⁻ | Br⁻ | Br⁻ |
| Crystalline form | Amorphous reddish orange powder | Amorphous orange powder | Amorphous reddish orange powder | Amorphous reddish orange powder | Amorphous red powder |
| Specific rotatory [α]_D power | −120° (C=0.16, CH₃OH) | −57° (C=0.15, CH₃OH) | −81° (C=0.11, MeOH) (27° C.) | +76° (C=0.13, MeOH) (27° C.) | −26° (C=0.07, DMSO) (28° C.) |
| Infrared absorption (KBr, cm⁻¹) | 1750, 1680, 1630, 1580, 1560, 1460, 1370, 1290, 1220, 1040, 930, 810, 750 | 1750, 1630, 1590, 1560, 1465, 1370, 1290, 1210, 1040, 885 | 1750, 1630, 1580, 1480, 1460, 1390, 1370, 1240, 1210, 1040, 930, 890, 810 | 1750, 1630, 1580, 1480, 1460, 1390, 1370, 1240, 1210, 1040, 930, 890, 810 | 1630, 1580, 1560, 1490, 1480, 1440, 1400, 1300, 1180, 1090, 1050, 1035, 905, 800, 3250 |
| Ultraviolet absorption (λ_max^EtOH, nm) | 210 (ε19000), 280 (ε22000), 244 (ε21000), 321 (ε58000), 258 (ε25000) | 210 (ε21000), 280 (ε23000), 247 (ε23000), 322 (ε55000), 259 (ε25000) | 209 (ε21000), 282 (ε22000), 245 (ε23000), 320 (ε58000), 258 (ε26000) | 209 (ε21000), 282 (ε22000), 245 (ε23000), 320 (ε58000), 258 (ε26000) | 211 (ε25000), 284 (ε26000), 227 (ε17000), 328 (ε52000), 270 (ε31000) |
| Mass spectrum (SIMS, m/z) | 648 | 635 | 577 | 577 | 409 |
| Proton NMR (DMSO-d₆, δ in ppm, CD₂HSOCD₃ proton chemical shift (δ 2.50) was used as internal standard, Intensity of NMR magnetic field was indicated in each compound) | [C₃₄H₃₈N₃O₁₀]⁺ 1.49 (3H,S) 1.98, 2.05, 2.08 (each 3H,S) 2.37 (3H,S) 3.12 (3H,S) 4.28 (3H,S) 4.30 (3H,m) 4.93 (1H,m) 5.35 (1H,t,J=9Hz) 5.49 (1H,d,J=9Hz) 6.30 (1H,d,J=9.9Hz,1'-H) 7.53 (1H,dd,J=2,9Hz) | [C₃₃H₃₅N₂O₁₁]⁺ 1.78, 2.04, 2.07 (each 3H, S) 2.37 (3H,S) 3.14 (3H,S) 3.69 (3H,S) 4.29 (3H,S) 4.90 (1H,d,J=9Hz) 5.65 (1H, t,J=9Hz) 5.70 (1H,t,J=9Hz) 6.05 (1H,t,J=9Hz) 6.47 (1H,d,J=9Hz,1'-H) 7.55 (1H,dd,J=2,9Hz) | [C₃₁H₃₃N₂O₉]⁺ [β-form] 1.78, 2.04, 2.08 (each 3H, S) 2.37 (3H,S) 3.16 (3H,S) 4.32 (3H,S) 3.88 (1H,m) 4.40 (1H,m), 5.48–5.56 (2H,m) 5.91 (1H,m) 6.32 (1H,d,J=9Hz, 1'-H) 7.55 (1H,dd,J=2Hz,8Hz) 7.90 (1H,d,J=8Hz) 8.31 (1H,d, | [C₃₁H₃₃N₂O₉]⁺ Same as in compound 143 | [C₂₁H₂₅N₂O₅]⁺ Same as in compound 146 |
| Elementary analysis Molecular formula Calc. (C, H, N) % Found (C, H, N) % | C₃₁H₃₃N₂O₉Cl.4H₂O 54.35, 6.03, 4.09 54.30, 6.01, 4.02 | — | | | |

(SIMS, m/z)
Proton NMR (DMSO-d₆, δ in ppm, CD₂HSOCD₃ proton chemical shift (δ 2.50) was used as internal standard, Intensity of NMR magnetic field was indicated in each compound):

Compound 141: [C₃₁H₃₃N₂O₉]⁺ 1.76, 2.26, 2.28 (each 3H,S) 2.37 (3H,S) 3.16 (3H,S) 4.30 (2H,m) 4.32 (3H,S) 5.05 (1H,d) 5.53 (2H,m) 6.59 (1H,d,J=9Hz,1'-H) 7.55 (1H,dd,J=2,9Hz) 7.90 (1H,d,J=9Hz) 8.29 (1H,d,J=2Hz) 8.65 (2H,S) 10.29 (1H,S) (270 MHz)

Compound 143: [C₃₄H₃₇N₂O₁₁]⁺ 1.81, 1.99, 2.00, 2.29 (each 3H,S) 2.37 (3H,S) 3.18 (3H,S) 4.25 (2H,m) 4.34 (3H,S) 4.76 (1H,m) 5.45–5.63 (3H,m) 6.46 (1H,d,J=9Hz,1'-H) 7.56 (1H,dd,J=1.3Hz,9Hz) 7.91 (1H,d,J=9Hz) 8.31 (1H,d,J=1.3Hz) 8.59 (1H,d,J=8Hz) 8.69 (1H,d,J=8Hz) 10.18 (1H,S) (270 MHz)

Compound 144: [C₃₄H₃₇N₂O₁₁]⁺ 1.81, 1.99, 2.00, 2.29 (each 3H,S) 2.37 (3H,S) 3.15 (3H,S) 4.27 (2H,m) 4.31 (3H,S) 4.43 (1H,m) 5.56–5.60 (2H,m) 5.93 (1H,m) 6.42 (1H,dd,J=8.5Hz,1'-H) 7.55 (1H,dd,J=2,8.5Hz) 7.90 (1H,d,J=8.5Hz) 8.30 (1H,d,J=2Hz) 8.65 (1H,d,J=7.5Hz) 8.75 (1H,d,J=7.5Hz) 10.24 (1H,S)

Compound 145: [C₃₄H₃₇N₂O₁₁]⁺ 1.79, 2.01, 2.05, 2.09 (each 3H,S) 2.37 (3H,S) 3.15 (3H,S) 4.31 (3H,S) 4.27 (2H,m) 4.43 (1H,m) 5.56–5.60 (2H,m) 5.93 (1H,m) 6.42 (1H,dd,J=8.5Hz,1'-H) 7.55 (1H,dd,J=2,8.5Hz) 7.90 (1H,d,J=8.5Hz) 8.30 (1H,d,J=2Hz) 8.65 (1H,d,J=7.5Hz) 8.75 (1H,d,J=7.5Hz) 10.24 (1H,S)

TABLE 2-continued

| Example No. | 146 | 147 | 148 | 149 | 150 |
|---|---|---|---|---|---|
| R² (compound) | [pyranose structure with OH groups] | [pyranose structure with OH and CH₃] | [pyranose structure with OH and CH₃] | [pyranose structure with OH groups] | [pyranose structure with OH groups] |
| R¹ | OH | OH | OH | OH | OH |
| R³ | CH₃ | CH₃ | CH₃ | CH₃ | CH₃ |
| X⁻ | Br⁻ | Br⁻ | Br⁻ | Br | Br⁻ |
| Crystalline form | Amorphous red powder | Amorphous reddish orange powder | Amorphous reddish orange powder | Amorphous orange powder | Amorphous orange powder |
| Specific rotatory [α]_D power | (28° C.) +28° (C=0.07, DMSO) | (28° C.) −97° (C=0.07, DMSO) | (28° C.) +89° (C=0.06, DMSO) | (28° C.) −108° (C=0.06, DMSO) | (28° C.) +122° (C=0.06, DMSO) |
| Infrared absorption (KBr, cm⁻¹) | 1630, 1580, 1560, 1490, 1480, 1440, 1300, 1180, 1090, 1050, 1035, 905, 800, 3250 | 3370, 1630, 1590, 1470, 1440, 1400, 1220, 1200, 1140, 1120, 1100, 1040, 1000, 900, 880, 860, 820, 810, 740 | 3370, 1630, 1590, 1470, 1440, 1400, 1220, 1200, 1140, 1120, 1100, 1040, 1000, 900, 880, 860, 820, 810, 740 | 3250, 2910, 1630, 1580, 1560, 1480, 1400, 1230, 1180, 1150, 1090, 900, 800, 745 | 3250, 2910, 1630, 1580, 1560, 1480, 1400, 1230, 1180, 1150, 1090, 900, 900, 800 |
| Ultraviolet absorption (λ_max^EtOH, nm) | 211 (ε25000) 284 (ε26000) 227 (ε17000) 328 (ε52000) 270 (ε31000) | 212 (ε25000) 283 (ε26000) 227 (ε17000) 328 (ε52000) 270 (ε30000) | 212 (ε25000) 282 (ε26000) 227 (ε17000) 328 (ε52000) 270 (ε30000) | 211 (ε25000) 284 (ε25000) 227 (ε17000) 327 (ε49000) 270 (ε29000) | 211 (ε22000) 285 (ε23000) 227 (ε15000) 328 (ε46000) 270 (ε27000) |
| Mass spectrum (SIMS, m/z) | 409 [C₂₃H₂₅N₂O₅]⁺ | 423 [C₂₄H₂₇N₂O₅]⁺ | 423 [C₂₄H₂₇N₂O₅]⁺ | 409 [C₂₃H₂₅N₂O₅]⁺ | 409 [C₂₃H₂₅N₂O₅]⁺ |
| Proton NMR (DMSO-d₆, δ in ppm, CD₂HSOCD₃ proton chemical shift (δ 2.50) was used as internal standard, Intensity of NMR magnetic field was indicated in each compound) | 3.10 (3H,S) 3.28 (3H,S) 3.84–3.88 (2H,m) 3.91–3.97 (2H,m) 4.09 (1H,m) 4.24 (3H,S) 5.12 (1H,d,J=6Hz) 5.41 (1H,brd) 5.48 (1H,d) 5.98 (1H,d,J=9Hz,1'-H) 7.22 (1H,dd,J=2Hz,9Hz) 7.65 (1H,d,J=9Hz) 7.86 (1H,d,J=2Hz) 8.55 (2H,S) 9.54 (1H,brs) 10.05 (1H,S) (360 MHz) | Same as in compound 148 | 1.30 (3H,d,J=6.5Hz) 3.12 (3H,S) 3.26 (3H,S) 3.62–3.69 (2H,m) 3.88 (1H,m) 4.04 (1H,q,J=6.5Hz) 4.77 (1H,d,J=6.5Hz) 5.20 (1H,d J=5.5Hz), 5.58 (1H,d,J=5Hz) 5.81 (1H,d,J=8.5Hz,1'-H) 7.23 (1H,dd,J=2Hz,9Hz) 7.66 (1H,d,J=9Hz) 7.87 (1H,d,J=2Hz) 8.51 (1H,d,J=7.5Hz) 9.55 (1H,brs) 10.03 (1H,S) (360 MHz) | 3.00 (3H,S) 3.25 (3H,S) 3.66 (1H,m) 3.91 (3H,m) 4.10 (1H,d) 4.22 (3H,S) 5.13 (1H,d) 5.25 (1H,d) 5.63 (1H,d) 5.76 (1H,d,J=9Hz, 1'-H) 7.23 (1H,dd,J=9Hz) 7.86 (1H,d, J=2Hz) 8.50 (1H,d,J=7.5Hz) 8.61 (1H,d,J=7.5Hz) 9.54 (1H,S) 10.02 (1H,S) (360 MHz) | Same as in the left |
| Elementary analysis Molecular formula Calc. (C, H, N) % Found (C, H, N) % | C₃₄H₃₈N₃O₁₀Cl.3.5H₂O 54.65, 6.07, 5.62 54.82, 5.70, 5.66 | — | C₃₁H₃₃N₂O₉Br.2.5H₂O 53.00, 5.45, 3.99 53.16, 5.11, 4.05 | C₃₁H₃₃N₂O₉Br.2.5H₂O 53.00, 5.45, 3.99 53.05, 5.31, 3.85 | C₂₃H₂₅N₂O₅Br 56.45, 5.15, 5.72 56.71, 5.32, 5.69 |
| compound | 7.85 (1H,d,J=9Hz) 8.27 (1H,d,J=2Hz) 8.47 (1H,d,J=9Hz) 8.64 (2H,ABq) 10.16 (1H,S) | 7.88 (1H,d,J=9Hz) 8.28 (1H,d,J=2Hz) 8.66 (1H,d,J=7Hz) 8.80 (1H,d,J=7Hz) 10.26 (1H,S) | J=2Hz) 8.66 (1H,d,J=7.5Hz) 8.73 (1H,d,J=7.5Hz) 10.23 (1H,S) [α-form] 1.96, 2.19, 2.28 (each 3H,S) 5.40 4.85 (1H,m) 5.21 (1H,m) (1H,m) 6.63 (1H,S,1'-H) 10.14 (1H,S) 270 MHz | | |

TABLE 2-continued

| Elementary analysis | | | | |
|---|---|---|---|---|
| Molecular formula | $C_{23}H_{25}N_2O_5Br$ | $C_{24}H_{27}N_2O_5Br$ | $C_{24}H_{27}N_2O_5Br$ | $C_{23}H_{25}N_2O_5Br \cdot \frac{1}{2}H_2O$ | $C_{23}H_{25}N_2O_5Br \cdot \frac{1}{2}H_2O$ |
| Calc. (C, H, N) % | 56.45, 5.15, 5.72 | 57.26, 5.41, 5.56 | 57.26, 5.41, 5.56 | 55.43, 5.26, 5.62 |
| Found (C, H, N) % | 56.32, 5.15, 5.68 | 57.58, 5.54, 5.62 | 57.35, 5.41, 5.52 | 55.64, 5.15, 5.63 | 55.38, 5.03, 5.59 |
| Example No. | 151 | 152 | 153 | 153 | 154 |
| R² | [structure] | [structure] | [structure] | [structure] | [structure] |
| R¹ | OH | OH | OH | OH | OH |
| R³ | CH₃ | CH₃ | CH₃ | CH₃ | CH₃ |
| X⁻ | Cl⁻ | Cl⁻ | Br⁻ | Br⁻ | Br⁻ |
| Crystalline form | Amorphous orange powder | Amorphous orange powder | Amorphous reddish orange powder | Amorphous reddish orange powder | Amorphous red powder |
| Specific rotatory $[\alpha]_D$ power | −47° (C=0.06, DMSO) (28° C.) | +58° (C=0.06, DMSO) (28° C.) | +98° (C=0.07, DMSO) (28° C.) | −96° (C=0.06, DMSO) (28° C.) | 53° (C=0.06, DMSO) 53° (C=0.06, DMSO) |
| Infrared absorption (KBr, cm⁻¹) | 3280, 2910, 1630, 1580, 1560, 1480, 1400, 1225, 1185, 1125, 1105, 1080, 1050, 910, 810, 740 | 3280, 2910, 1630, 1580, 1560, 1480, 1400, 1225, 1185, 1125, 1105, 1080, 1050, 910, 810, 740 | 3350, 1630, 1590, 1470, 1440, 1400, 1220, 1200, 1180, 1140, 1120, 1090, 1050, 900, 880, 801, 800, 740 | 3350, 1630, 1590, 1470, 1440, 1400, 1220, 1200, 1180, 1140, 1120, 1090, 1050, 900, 880, 810, 800, 740 | 3300, 1630, 1580, 1480, 1440, 1400, 1380, 1370, 1350, 1320, 1310, 1290, 1220, 1200, 1100, 1070, 1040, 1010 |
| Ultraviolet absorption ($\lambda_{max}^{EtOH}$, nm) | 212 (ε24000) 284 (ε25000) 227 (ε16000) 328 (ε50000) 270 (ε29000) | 211 (ε22000) 284 (ε24000) 227 (ε16000) 328 (ε47000) 270 (ε28000) | 212 (ε18000) 284 (ε19000) 227 (ε12000) 328 (ε37000) 270 (ε22000) | 212 (ε18000) 284 (ε19000) 227 (ε12000) 328 (ε37000) 270 (ε22000) | 210 (ε24000) 284 (ε26000) 227 (ε1700) 328 (ε52000) 270 (ε31000) |
| Mass spectrum (SIMS, m/z) | 409 | 409 | 439 | 439 | 439 |
| Proton NMR (DMSO-d₆, δ in ppm, CD₂HSOCD₃ proton chemcial shift (δ 2.50) was used as internal standard, Intensity of NMR magnetic field was indicated in each compound) | [C₂₃H₂₅N₂O₅]⁺ 3.11 (3H,S) 3.27 (3H,S) 3.75 (1H,m) 3.95 (1H,d,J=12Hz) 4.16 (1H,d,J=12Hz) 4.02 (2H,m) 4.23 (3H,S) 5.41 (1H,d) 5.51 (1H,d) 5.72 (1H,d) 6.03 (1H,d,J=9Hz,1'-H) 7.23 (1H,dd,J=2,9Hz) 7.88 (1H,d,J=2Hz) 8.55 (1H,d, J=7.5Hz) 8.59 (1H,d,J=7.5Hz) 9.59 (1H,brs) 10.07 (1H,S) (360 MHz) | [C₂₃H₂₅N₂O₅]⁺ Same as in compound 151 | [C₂₄H₂₇N₂O₆]⁺ 3.05 (3H,S) 3.18 (3H,S) 3.64-3.73 (3H,m) 3.87-3.95 (3H,m) 4.17 (3H,S) 4.90 (1H,brs) 4.99 (1H,d,J=7Hz) 5.26 (1H,brs) 5.66 (1H,brs) 5.84 (1H,d,J=8.5Hz, 1'-H) 7.22 (1H,dd,J=2H,9Hz, J=2Hz) 8.50 (1H,d,J=7.5Hz) 8.56 (1H,d,J=7.5Hz) 9.55 (1H,brs) 9.98 (1H,S) 360 MHz | [C₂₄H₂₇N₂O₆]⁺ Same as in the left | [C₂₄H₂₇N₂O₆]⁺ 3.11 (3H,S) 3.42–3.51 (2H,m) 3.57–3.71 (3H,m) 3.84 (1H,m) 4.23 (3H,S) 4.81 (1H,t,J=5.5Hz) 5.38 (1H,d,J=5Hz) 5.52 (1H,d J=4Hz) 5.72 (1H,d,J=5Hz) 5.88 (1H,d,J=9Hz,1'-H) 7.24 (1H,dd,J=2,9Hz) 7.87 (1H,d,J=2Hz) 8.57 (2H,S) 9.56 (1H,brs) 10.03 (1H,S) |

| Elementary analysis | | | | |
|---|---|---|---|---|
| Molecular formula | $C_{23}H_{25}N_2O_5Cl \cdot H_2O$ | $C_{23}H_{25}N_2O_5Cl \cdot H_2O$ | $C_{24}H_{27}N_2O_6Br$ | $C_{24}H_{27}N_2O_6Br$ | $C_{24}H_{27}N_2O_6Br \cdot \frac{1}{2}H_2O$ |
| Calc. (C, H, N) % | 59.68, 5.88, 6.05 | 59.68, 5.88, 6.00 | 55.50, 5.24, 5.39 | 55.50, 5.24, 5.39 | 54.55, 5.34, 5.30 |
| Found (C, H, N) % | 59.78, 5.69, 6.07 | 59.46, 5.58, 6.00 | 55.42, 5.14, 5.34 | 55.21, 5.29, 5.35 | 54.88, 5.19, 5.27 |
| Example No. | 154 | 155 | 156 | 157 | 158 |

TABLE 2-continued

| $R^2$ | [structure with OH, OH, OH, O-OH] | [structure with AcHN, OH, OH, O-OH] | [structure with OH, OH, OH, O-CONH₂] | [structure with OH, OH, ||||OH, O] | [structure with OH, OH, OH, O] |
|---|---|---|---|---|---|
| $R^1$ | OH | OH | OH | OH | OH |
| $R^3$ | CH₃ | CH₃ | CH₃ | CH₃ | CH₃ |
| $X^-$ | Br⁻ | Cl⁻ | Br⁻ | Br⁻ | Br⁻ |
| Crystalline form | Amorphous red powder | Amorphous reddish orange powder | Amorphous orange powder | Amorphous red powder | Amorphous red powder |
| Specific rotatory $[\alpha]_D$ power | −58° (C=0.04, DMSO) | −83° (C=0.07, DMSO) | +20° (C=0.05, DMSO) | +30° (C=0.06, DMSO) (28° C.) | −28° (C=0.05, DMSO) (28° C.) |
| Infrared absorption (KBr, cm⁻¹) | 3300, 1630, 1580, 1480, 1440, 1400, 1380, 1370, 1350, 1320, 1310, 1290, 1220, 1200, 1100, 1070, 1040, 1010 | 3300, 1670, 1640, 1590, 1560 1480, 1400, 1300, 1225, 1100 1050 | 3300, 1680, 1630, 1580, 1470, 1445, 1400, 1220, 1095, 800 | 3300, 1680, 1630, 1580, 1470, 1400, 1220 1180, 1100, 1050, 1000, 900, 810, 3300 | 1630, 1580, 1470, 1400, 1220, 1180, 1100, 1050, 1000, 900, 810, 3300 |
| Ultraviolet absorption ($\lambda_{max}^{EtOH}$, nm) Intensity of absorption | 210 (ε24000) 284 (ε26000) 227 (ε17000) 328 (ε52000) 270 (ε31000) | 210 (ε22000) 285 (ε23000) 228 (ε15000) 330 (ε45000) 272 (ε28000) | 210 (ε27000) 284 (ε29000) 227 (ε19000) 329 (ε56000) 270 (ε34000) | 210 (ε25000) 284 (ε26000) 227 (ε17000) 328 (ε50000) 270 (ε30000) | 210 (ε25000) 284 (ε26000) 227 (ε17000) 328 (ε50000) 270 (ε30000) |
| Mass spectrum (SIMS, m/z) | 439 [C₂₄H₂₇N₂O₆]⁺ | 480 [C₂₆H₃₀N₃O₆]⁺ | 452 [C₂₄H₂₆N₃O₆]⁺ | 409 [C₂₃H₂₅N₂O₅]⁺ | 409 [C₂₃H₂₅N₂O₅]⁺ Same as in compound 157 |
| Proton NMR (DMSO—d₆, δ in ppm, CD₂HSOCD₃ proton chemical shift (δ 2.50) was used as internal standard, Intensity of NMR magnetic field was indicated in each compound) | 3.11 (3H,S) 3.42–3.51 (2H,m) 3.57–3.71 (3H,m) 3.84 (1H,m) 4.23 (3H,S) 4.81 (1H,t,J=5.5Hz) 5.38 (1H,d,J=5Hz) 5.52 (1H,d, J=4Hz) 5.72 (1H,d,J=5Hz) 5.88 (1H,d,J=9Hz,1'-H) 7.24 (1H,dd,J=2,9Hz) 7.66 (1H,d,J=9Hz) 7.87 (1H,d,J=2Hz) 8.57 (2H,S) 9.56 (1H,brs) 10.03 (1H,S) | 1.52 (3H,S) 3.05 (3H,S) 3.23 (3H,S) 3.63 (4H,m) 3.88 (1H,m) 4.12 (1H,m) 4.17 (3H,S) 4.89 (1H,t) 5.48 (1H,d) 5.50 (1H,d) 5.94 (1H,d,J=9.5Hz,1'-H) 7.23 (1H,dd,J=2,9Hz) 7.62 (1H,d,J=9Hz) 7.84 (1H, d,J=2Hz) 8.28 (1H,d,J=9Hz) 8.49 (1H,d,J=7.5Hz) 8.54 (1H,d,J=7.5Hz) 9.60 (1H,S) | 3.11 (3H,S) 3.49 (1H,m) 3.70–3.77 (2H,m) 3.94 (1H,d, J=10Hz) 4.24 (3H,S) 5.52 (1H, d,J=5.5Hz) 5.64 (1H,d,J=4.5Hz) 5.78 (1H,m) 5.93 (1H,dd,J=9Hz, 1'-H) 7.23 (1H,dd,J=9.5Hz,1'-H) 7.40 (1H,S) 7.72 (1H,S) 7.66 (1H,d,J=9Hz) 7.87 (1H,d,J=2Hz) 8.58 (1H,d,J=7.5Hz) 8.64 (1H,d,J=7.5Hz) 9.56 (1H,brs) 10.05 (1H,S) | [β-form] 3.14 (3H,S) 3.65–3.79 (3H,m) 4.08–4.20 (2H,m) 4.27 (3H,S) 5.35 (1H,d,J=5.5Hz) 5.53 (1H, d,J=4.5Hz) 5.71 (1H,d,J=5.5Hz) 5.81 (1H,d,J=9Hz,1'-H) 7.24 (1H,dd,J=2Hz,9Hz) 7.68 (1H,d, J=9Hz) 7.89 (1H,d,J=2Hz) 8.57 (2H,S) 9.54 (1H,S) 10.04 (1H,S) [α-form] 4.26 (3H,S) 5.42 (1H,d,J=8Hz) 5.60 (1H,d,J=5.5Hz) 5.87 (1H, d,J=3.5Hz) 6.34 (1H,brs,1'-H) 7.67 (1H,d,J=9Hz) 9.52 (1H,S) 10.00 (1H,S) 360 MHz | |

Elementary analysis

| | | | | | |
|---|---|---|---|---|---|
| Molecular formula | C₂₄H₂₇N₂O₆Br.½H₂O | C₂₆H₃₀N₃O₆Br.½H₂O | — | C₂₃H₂₅N₂O₅Br.½H₂O | C₂₃H₂₅N₂O₅Br.½H₂O |
| Calc. (C, H, N) % | 54.55, 5.34, 5.30 | | | 55.43, 5.26, 5.62 | 55.43, 5.26, 5.62 |
| Found (C, H, N) % | 54.63, 5.32, 5.21 | | | 55.36, 5.14, 5.61 | 55.38, 5.25, 5.69 |
| Example No. | 159 | 160 | 160 | 161 | 162 |

TABLE 2-continued

| | | | | | |
|---|---|---|---|---|---|
| R² | [structure with OAc, OAc, OAc, CH₃] | [structure with OAc, OAc, OAc, CH₂OAc] | [structure with OAc, OAc, OAc, CH₂OAc] | [structure with OH, OH, OH, CH₃] | [structure with OH, OH, OH, OH] |
| R¹ | OH | OH | OH | OH | OH |
| R³ | CH₃ | CH₃ | CH₃ | CH₃ | CH₃ |
| X⁻ | Br⁻ | Br⁻ | Br⁻ | Br⁻ | Br⁻ |
| Crystalline form | Amorphous orange powder | Amorphous orange powder | Amorphous orange powder | Amorphous reddish orange powder | Amorphous orange powder |
| Specific rotatory [α]_D | +35° (C=0.04, MeOH) (27° C.) | +44° (C=0.06, MeOH) (28° C.) | (28° C.) | +3° (C=0.13, DMSO) (28° C.) | +75° (C=0.07, DMSO) (28° C.) |
| Infrared absorption (KBr, cm⁻¹) | 3400, 3150, 1750, 1640, 1590, 1565, 1480, 1410, 1380, 1220, 1140, 1050, 915, 810, 750 | 3400, 3100, 1750, 1630, 1585, 1560, 1470, 1450, 1400, 1390, 1220, 1050, 800, 745 | 3400, 3100, 1750, 1630, 1585, 1560, 1470, 1450, 1400, 1390, 1220, 1050 | 3250, 2900, 1630, 1580, 1560, 1470, 1395, 1220, 1200, 1180, 1140, 1100, 1040, 920, 800, 740 | 3250, 2900, 1630, 1585, 1560, 1470, 1400, 1220, 1110, 1050, 810, 750 |
| Ultraviolet absorption (λ_max^EtOH, nm) | 211 (ε22000) 286 (ε23000) 228 (ε15000) 331 (ε43000) 272 (ε27000) | 210 (ε24000) 288 (ε23000) 228 (ε16000) 330 (ε42000) 273 (ε27000) | 210 (ε24000) 288 (ε23000) 228 (ε16000) 330 (ε42000) 273 (ε27000) | 209 (ε27000) 284 (ε27000) 226 (ε18000) 327 (ε53000) 269 (ε31000) | 211 (ε23000) 283 (ε25000) 227 (ε16000) 327 (ε48000) 270 (ε28000) |
| Mass spectrum (SIMS, m/z) | 549 | 607 | 607 | 423 | 439 |
| Proton NMR (DMSO—d₆, δ in ppm, CD₂HSOCD₃ proton chemical shift (δ 2.50) was used as internal standard, Intensity of NMR magnetic field was indicated in each compound) | [C₃₀H₃₃N₂O₈]⁺ 1.56 (3H,d,J=7Hz) 1.86, 2.20 2.25 (each 3H,S) 3.11 (3H,S) 3.30 (3H,S) 4.25 (3H,S) 4.53 (1H,m) 4.99 (1H,t) 5.50 (1H,t) 5.76 (1H,dd) 6.70 (1H, d,J=8Hz,1'-H) 7.24 (1H,dd, J=2,9Hz) 7.68 (1H,d,J=9Hz) 7.90 (1H,d,J=2Hz) 8.59 (2H,AB) 9.58 (1H,S) 10.13 (1H,S) (360 MHz) | [C₃₂H₃₅N₂O₁₀]⁺ 1.86, 2.06, 2.20, 2.24 (each 3H,S) 3.13 (3H,S) 4.26 (3H,S) 4.48 (1H,m) 4.61 (2H,m) 5.18 (1H,t) 5.55 (1H,t) 5.80 (1H,dd) 6.73 (1H, d,J=8Hz,1'-H) 7.24 (1H,dd, J=2,9Hz) 7.70 (1H,d,J=9Hz) 7.91 (1H,d,J=2Hz) 8.59 (2H,S) 9.59 (1H,brs) 10.08 (1H,S) (270 MHz) | [C₃₃H₃₅N₂O₁₀]⁺ Same as in the left | [C₂₄H₂₇N₂O₅]⁺ 1.53 (3H,d,J=7Hz) 3.09 (3H,S) 3.26 (3H,S) 3.71 (1H,m) 4.00 (1H,m) 4.10 (1H,m) 4.23 (3H,S) 4.32 (1H,m) 5.38 (1H,d) 5.46 (1H,d) 5.64 (1H,d) 6.23 (1H,d,J=9Hz,1'-H) 7.22 (1H,dd,J=2,9Hz) 7.64 (1H,d,J=9Hz) 7.86 (1H,d,J=2Hz) 8.57 (2H,S) 9.52 (1H,S) 10.07 (1H,S) 360 MHz | [C₂₄H₂₇N₂O₆]⁺ 3.10 (3H,S) 3.26 (3H,S) 3.70 (1H,m) 4.02 (1H,m) 3.78 (1H,m) 3.96 (1H,m) 4.11 (2H,m) 4.23 (3H,S) 4.95 (1H,t) 5.45 (1H,d) 5.51 (1H,d) 5.66 (1H,d) 6.17 (1H,d,J=9Hz,1'-H) 7.23 (1H,dd,J=2,9Hz) 7.64 (1H,d,J=9Hz) 7.86 (1H,d,J=2Hz) 8.58 (2H,S) 9.54 (1H,brs) 10.07 (1H,S) (360 MHz) |

Elementary analysis

| Molecular formula Calc. (C, H, N) % Found (C, H, N) % | — | C₃₂H₃₅N₂O₁₀Br.2.5H₂O 52.47, 5.50, 3.82 52.43, 5.13, 3.76 | C₃₂H₃₅N₂O₁₀Br.2.5H₂O 52.47, 5.50, 3.82 52.56, 5.35, 3.91 | C₂₄H₂₇N₂O₅Br 57.26, 5.41, 5.56 56.94, 5.40, 5.53 | C₂₄H₂₇N₂O₆Br.1.5H₂O 52.76, 5.53, 5.13 52.50, 5.18, 5.04 |
| --- | --- | --- | --- | --- | --- |
| Example No. | 162 | 163 | 164 | 165 | 166 |
| R² | [structure with OH, OH, CH₂OH] | [structure with OAc, OAc, OAc, CH₃] | [structure with OH, OH, CH₃] | [structure with OAc, OAc, OAc, CH₃] | [structure with OH, OH, CH₃] |
| R¹ | OH | OAc | OH | OAc | OH |

TABLE 2-continued

| | | | | | |
|---|---|---|---|---|---|
| $R^3$ | $CH_3$ | $-CH_2CH_3$ | $-CH_2CH_3$ | $-CH\begin{smallmatrix}CH_3\\CH_3\end{smallmatrix}$ | $-CH\begin{smallmatrix}CH_3\\CH_3\end{smallmatrix}$ |
| $X^-$ | $Br^-$ | $Br^-$ | $Br^-$ | $Br^-$ | $Br^-$ |
| Crystalline form | Amorphous orange powder | Amorphous orange powder | Amorphous orange powder | Amorphous red powder | Amorphous reddish orange powder |
| Specific rotatory $[\alpha]_D$ power | $-78°$ (28° C.) (C=0.07, DMSO) | $+25°$ (27° C.) (C=0.11, MeOH) | $+9°$ (28° C.) (C=0.06, DMSO) | $+33°$ (28° C.) (C=0.15, MeOH) | $+13°$ (28° C.) (C=0.06, DMSO) |
| Infrared absorption (KBr, $cm^{-1}$) | 3250, 2900, 1630, 1585, 1500, 1470, 1400, 1220, 1110, 1050 | 1750, 1630, 1585, 1560, 1470, 1400, 1370, 1200, 1135, 1050, 910, 805, 740 | 3300, 1630, 1585, 1470, 1400, 1415, 1220, 1050, 800, 735 | 1750, 1630, 1580, 1470, 1400, 1370, 1210, 1140, 1055, 940, 910, 810 | 1630, 1580, 1470, 1400, 1280, 1215, 1140, 1100, 1050, 910, 805, 3300 |
| Ultraviolet absorption ($\lambda_{max}$ EtOH, nm) | 211 (ε23000) 283 (ε23000) 227 (ε16000) 327 (ε48000) 270 (ε28000) | 209 (ε23000) 283 (ε23000) 245 (ε23000) 320 (ε60000) 258 (ε27000) | 212 (ε25000) 283 (ε27000) 227 (ε23000) 327 (ε52000) 270 (ε31000) | 210 (ε22000) 283 (ε23000) 245 (ε24000) 320 (ε57000) 258 (ε27000) | 212 (ε25000) 284 (ε28000) 230 (ε17000) 328 (ε53000) 270 (ε31000) |
| Mass spectrum (SIMS, m/z) | 439 $[C_{24}H_{27}N_2O_6]^+$ | 605 $[C_{33}H_{37}N_2O_9]^+$ | 437 $[C_{25}H_{29}N_2O_5]^+$ | 619 $[C_{34}H_{39}N_2O_9]^+$ | 451 $[C_{26}H_{31}N_2O_5]^+$ |
| Proton NMR (DMSO-$d_6$, δ in ppm, $CD_2HSOCD_3$ proton chemical shift (δ 2.50) was used as internal standard, Intensity of NMR magnetic field was indicated in each compound) | Same as in the left | 1.50 (3H,t,J=7Hz) 1.54 (3H,d J=7Hz) 1.85, 2.20, 2.24 (each 3H,S) 2.38 (3H,S) 3.14 (3H,S) 3.37 (3H,S) 4.53 (1H,m) 4.85 (2H,q,J=7Hz) 4.99 (1H,t) 5.51 (1H,t) 5.79 (1H,dd) 6.71 (1H,d,J=8Hz,1'-H) 7.56 (1H,dd, J=2,9Hz) 7.94 (1H,d,J=9Hz) 8.32 (1H,d,J=2Hz) 8.70 (2H, ABq) 10.22 (1H,S) (360 MHz) | 1.45 (3H,t,J=7Hz) 1.53 (3H, d,J=7Hz) 1.85, 2.20, 2.24 (each 3H,S) 3.07 (3H,S) 3.70 (1H,m) 3.99 (1H,m) 4.09 (1H,m) 4.32 (1H,m) 4.75 (2H,q,J=7Hz) 5.37 (1H,d) 5.46 (1H,d) 5.64 (1H,d) 6.23 (1H,d,J=9Hz, 1'-H) 7.23 (1H,dd,J=2,9Hz) 7.69 (1H,d,J=9Hz) 7.89 (1H, d,J=2Hz) 8.58 (1H,d,J=7.5Hz) 8.63 (1H,brs) 10.10 (1H,S) (360 MHz) | 1.54 (3H,d,J=6.5Hz) 1.71 (3H, d,J=6.5Hz) 1.75 (3H,d,J=6.5Hz) 1.85, 2.19, 2.24 (each 3H,S) 2.37 (3H,S) 3.07 (3H,S) 4.54 (1H,m) 4.99 (1H,t,J=4Hz) 5.50 (1H,t,J=4Hz) 5.62 (1H,dq, J=6.5Hz) 5.77 (1H,d,J=2Hz, 8Hz) 6.71 (1H,d,J=8Hz,1'-H) 7.48 (1H,dd,J=2.5Hz,9Hz) 8.06 (1H,d,J=9Hz) 8.31 (1H,d J=2.5Hz) 8.66 (1H,d,J=7.5Hz) 8.69 (1H,d,J=7.5Hz) 10.21 (1H,S) (270 MHz) | 1.53 (3H,d,J=7Hz) 1.67 (3H,d, J=7Hz) 1.68 (3H,d,J=7Hz) 3.04 (3H,S) 3.70 (1H,m) 3.99 (1H,q) 4.08 (1H,m) 4.31 (1H,dq) 5.37 (1H,d,J=7.5Hz) 5.46 (1H,m) 4.99 (1H,t,J=5.5Hz) 5.63 (1H,d,J=4Hz) 5.52 (1H,dq, J=7Hz) 6.24 (1H,d,J=9Hz,1'-H) 7.18 (1H,dd,J=2.5Hz,9Hz) 7.84 (1H,d,J=9Hz) 7.90 (1H,d, J=2.5Hz) 8.59 (2H,S) 9.54 (1H,S) 10.11 (1H,S) (360 MHz) |

Elementary analysis

| Molecular formula | $C_{46}H_{39}N_2O_9Br \cdot 1.5H_2O$ | — | $C_{24}H_{39}N_2O_4Br$ | — | — |
|---|---|---|---|---|---|
| Calc. (C, H, N) % | 63.54, 4.86, 3.22 | | 56.08, 5.84, 5.23 | | |
| Found (C, H, N) % | 63.51, 4.92, 3.25 | | 56.32, 5.43, 5.19 | | |

| Example No. | 167 | 168 | 169 | 170 |
|---|---|---|---|---|
| $R^2$ | sugar (tetra-OAc, $CH_3$) | sugar (di-OH, $CH_3$) | sugar (tri-OAc, $CH_3$) | sugar (tri-OH, $CH_3$) |
| $R^1$ | OAc | OH | H | H |
| $R^3$ | $-CH_2$-cyclopropyl | $-CH_2$-cyclopropyl | $CH_3$ | $CH_3$ |

TABLE 2-continued

| | | | | |
|---|---|---|---|---|
| X[-] | Br[-] | Br[-] | Br[-] | Br[-] |
| Crystalline form | Amorphous reddish orange powder | Amorphous orange powder | Amorphous yellowish orange powder | Amorphous yellowish orange powder |
| Specific rotatory $[\alpha]_D$ | +25° (C=0.13, MeOH) (28° C.) | +28° (C=0.05, DMSO) (28° C.) | +24° (C=0.13, CH$_3$OH) | −17° (C=0.07, DMSO) |
| Infrared absorption (KBr, cm$^{-1}$) | 1750, 1603, 1580, 1560, 1465, 1400, 1370, 1300, 1210, 1140, 1050, 910, 810, 755 | 3300, 1630, 1580, 1550, 1480, 1410, 1270, 1210, 1050, 920, 800, 740 | 1750, 1630, 1590, 1560, 1480, 1445, 1395, 1365, 1240, 1210, 1050 | 3300, 1630, 1585, 1560, 1480, 1470, 1450, 1400, 1300, 1240, 1050, 800, 750 |
| Ultraviolet absorption ($\lambda_{max}^{EtOH}$, nm) | 210 ($\epsilon$22000) 283 ($\epsilon$23000) 245 ($\epsilon$24000) 330 ($\epsilon$59000) 258 ($\epsilon$26000) | 212 ($\epsilon$26000) 284 ($\epsilon$27000) 227 ($\epsilon$17000) 328 ($\epsilon$53000) 270 ($\epsilon$31000) | 209 ($\epsilon$22000) 287 ($\epsilon$24000) 245 ($\epsilon$22000) 320 ($\epsilon$60000) 256 ($\epsilon$23000) | 209 ($\epsilon$21000) 286 ($\epsilon$25000) 244 ($\epsilon$23000) 316 ($\epsilon$68000) 254 ($\epsilon$25000) |
| Mass spectrum (SIMS, m/z) | 631 [C$_{35}$H$_{39}$N$_2$O$_9$]$^+$ | 463 [C$_{27}$H$_{31}$N$_2$O$_5$]$^+$ | 533 [C$_{30}$H$_{33}$N$_2$O$_7$]$^+$ | 407 [C$_{24}$H$_{27}$N$_2$O$_4$]$^+$ |
| Proton NMR (DMSO—d$_6$, $\delta$ in ppm, CD$_2$HSOCD$_3$ proton chemical shift ($\delta$ 2.50) was used as internal standard, Intensity of NMR magnetic field was indicated in each compound) | 0.46 (4H,m) 1.30 (1H,m) 1.54 (3H,d,J=6.6Hz) 1.87, 2.19, 2.24 (each 3H,S) 2.37 (3H,S) 3.17 (3H,S) 4.52 (1H,m) 4.80 (2H,d,J=6Hz) 5.00 (1H,t) 5.51 (1H,t) 5.81 (1H,dd) 6.72 (1H,d, J=8Hz,1'-H) 7.53 (1H,dd,J=2, 9Hz) 7.97 (1H,d,J=9Hz) 8.32 (1H,d,J=2Hz) 8.71 (2H,ABq) 10.23 (1H,S) (270 MHz) | 0.42 (4H,m) 1.25 (1H,m) 1.53 (3H,d,J=7Hz) 3.12 (3H,S) 3.70 (1H,m) 3.99 (1H,m) 4.09 (1H,m) 4.32 (1H,m) 4.71 (2H,d,J=6Hz) 5.38 (1H,d) 5.46 (1H,dd) 5.64 (1H,d) 6.14 (1H,d,J=9Hz,1'-H) 7.21 (1H,dd,J=2,9Hz) 7.72 (1H,d,J=9Hz) 7.89 (1H,d, J=2Hz) 8.59 (1H,d,J=7.5Hz) 9.54 (1H,brs) 10.13 (1H,S) (360 MHz) | 1.55 (3H,d,J=7.3Hz) 1.86, 2.19, 2.24 (each 3H,S) 3.17, 3.41, 4.32 (each 3H,S) 4.52 (1H,m) 4.99 (1H,t) 5.51 (1H,d) 5.80 (1H,dd) 6.70 (1H,d,J=8.5Hz,1'-H) 7.51 (1H,t,J=7.5Hz) 7.78 (1H,t,J=7.5Hz) 7.87 (1H,d,J=7.5Hz) 8.57 (1H,d,J=7.5Hz) 8.66 (2H,S) 10.18 (1H,S) | 1.54 (3H,d,J=7.3Hz) 3.16 (3H,S) 3.71, 4.00, 4.10, 4.33 (each 1H,m) 4.30 (3H,S) 5.39 (1H,d) 5.47 (1H,d) 5.65 (1H,d) 6.26 (1H,d,J=9Hz,1'-H) 7.47 (1H,t,J=7.5Hz) 7.76 (1H,t,J=7.5Hz) 7.84 (1H,d,J=7.5Hz) 8.52 (1H,d,J=7.5Hz) 8.64 (2H,ABq) 10.15 (1H,S) |
| Elementary analysis Molecular formula Calc. (C, H, N) % Found (C, H, N) % | — | C$_{27}$H$_{31}$N$_2$O$_5$Br 59.67, 5.75, 5.15 59.42, 5.88, 5.10 | — | — |

| Example No. | 171 | 172 |
|---|---|---|
| R$^2$ | (OAc-sugar structure with CH$_3$) | (OH-sugar structure with CH$_3$) |
| R$^1$ | OCH$_3$ | OCH$_3$ |
| R$^3$ | CH$_3$ | CH$_3$ |
| X[-] | Br[-] | Br[-] |
| Crystalline form | Amorphous reddish powder | Amorphous reddish orange powder |
| Specific rotatory $[\alpha]_D$ power | +42° (C=0.10, CH$_3$OH) | +20° (C=0.04, DMSO) |
| Infrared absorption (KBr, cm$^{-1}$) | 1760, 1640, 1590, 1560, 1480, 1400, 1380, 1300, 1220, 1140, 1070, 1050 | 3300, 1630, 1580, 1560, 1470 1390, 1290, 1260, 1220, 1180 1140, 1105, 1090, 1045 |
| Ultraviolet absorption ($\lambda_{max}^{EtOH}$, nm) | 211 ($\epsilon$24000) 285 ($\epsilon$24000) 229 ($\epsilon$18000) 328 ($\epsilon$51000) 270 ($\epsilon$29000) | 210 ($\epsilon$24000) 282 ($\epsilon$26000) 228 ($\epsilon$17000) 325 ($\epsilon$55000) 268 ($\epsilon$29000) |

TABLE 2-continued

| | | |
|---|---|---|
| Mass spectrum (SIMS, m/z) | 563 | 437 |
| Proton NMR (DMSO—d₆, δ in ppm, CD₂HSOCD₃ proton chemical shift (δ 2.50) was used as internal standard. Intensity of NMR magnetic field was indicated in each compound) | [C₃₁H₃₅N₂O₈]⁺<br>1.54 (3H,d,J=7Hz)<br>1.86, 2.19, 2.24 (each 3H,S)<br>3.15 (3H,S) 3.40 (3H,S)<br>3.97 (3H,S) 4.30 (3H,S)<br>4.50 (1H,m) 4.99 (1H,t,J=4Hz)<br>5.51 (1H,t,J=4Hz)<br>5.80 (1H,dd,J=4,8Hz)<br>6.67 (1H,d,J=8Hz,1'-H)<br>7.43 (1H,dd,J=2,9Hz)<br>7.82 (1H,d,J=9Hz) 8.02 (1H, d,J=2Hz) 8.62 (2H,S)<br>10.14 (1H,S) | [C₂₅H₂₉N₂O₅]⁺<br>1.54 (3H,d,J=7Hz) 3.13 (3H,S)<br>3.30 (3H,S) 3.96 (3H,S)<br>4.27 (3H,S) 3.71 (1H,m)<br>4.00 (1H,m) 4.09 (1H,dt, J=3,9Hz), 4.32 (1H,dq,J=2,7Hz)<br>5.38 (1H,d,J=7.5Hz)<br>5.46 (1H,d,J=5.5Hz)<br>5.65 (1H,d,J=4Hz) 6.25 (1H,d, J=9Hz) 7.40 (1H,dd,J=2.5,9Hz)<br>7.77 (1H,d,J=9Hz) 7.96 (1H,d, J=2.5Hz) 8.59 (1H,d,J=8Hz)<br>8.60 (1H,d,J=8Hz) 10.12 (1H,S) |
| Elementary analysis | | |
| Molecular formula | — | C₂₅H₂₉N₂O₅Br·H₂O |
| Calc. (C, H, N) % | | 56.08, 5.84, 5.23 |
| Found (C, H, N) % | | 55.90, 5.61, 5.20 |

EXAMPLE 113

Preparation of 2-(2,3,5-tri-O-benzoyl-β-D-xylofuranosyl)-9-acetoxy-6-methylellipticinium chloride

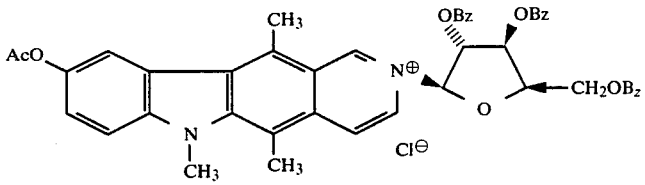

A 809 mg amount of 2,3,5-tri-O-benzoyl-α-D-xylofuranosyl chloride was dissolved in 30 ml of nitromethane and, then, 223 mg of 9-acetoxy-6-methylellipticine and 220 mg of cadmium carbonate were added thereto. The mixture was heated under reflux for 10 minutes. The insoluble matter was removed by filtration and the filtrate was concentrated.

The residue obtained above was subjected to silicagel column chromatography (Kieselgel 60, 100 ml), followed by eluting with methylene chloride-methanol (94:6–92:8). Thus, 170 mg of the product was obtained. This product was then subjected to gel filtration column chromatography (Sephadex LH20, 4.6 cmφ×32 cm), followed by eluting with methanol. As a result, 149 mg (27% yield) of the desired compound was obtained.

The results are shown in Table 2.

Similarly, 2-(2,3,5-tri-O-benzoyl-β-L-xylofuranosyl)-9-acetoxy-6-methylellipticinium chloride was obtained from 2,3,5-tri-O-benzoyl-α-L-xylofuranosyl chloride.

EXAMPLES 114 to 119

The following ellipticine derivatives were prepared in the same manner as in Example 113. The results are shown in Table 2.

Example 114:
2-(2,3,5-tri-O-benzoyl-β-D-ribofuranosyl)-9-acetoxy-6-methylellipticinium bromide.
2-(2,3,5-tri-O-benzoyl-β-L-ribofuranosyl)-9-acetoxy-6-methylellipticinium bromide.
Example 115:
2-(2,3,5-tri-O-benzoyl-α-L-arabinofuranosyl)-9-acetoxy-6-methylellipticinium bromide.
2-(2,3,5-tri-O-benzoyl-β-D-arabinofuranosyl)-9-acetoxy-6-methylellipticinium bromide.
Example 116:
2-(2,3-di-O-benzoyl-5-deoxy-α-L-arabinofuranosyl)-9-acetoxy-6-methylellipticinium chloride.
Example 117:
2-(2,3-di-O-benzoyl-β-D-erythrofuranosyl)-9-acetoxy-6-methylellipticinium chloride.
2-(2,3-di-O-benzoyl-β-L-erythrofuranosyl)-9-acetoxy-6-methylellipticinium chloride.
Example 118:
2-(2,3-di-O-benzoyl-5-deoxy-β-D-ribofuranosyl)-9-acetoxy-6-methylellipticinium chloride.
Example 119:
2-(2,3,5-tri-O-benzyl-β-D-arabinofuranosyl)-9-acetoxy-6-methylellipticinium bromide.
2-(2,3,5-tri-O-benzyl-β-L-arabinofuranosyl)-9-acetoxy-6-methylellipticinium bromide.

In Example 119, 1',2'-cis-compound was prepared from 2,3,5-tri-O-benzyl-α-D-arabinofuranosyl bromide or 2,3,5-tri-O-benzyl-α-L-arabinofuranosyl bromide.

EXAMPLE 120

Preparation of 2-β-D-xylofuranosyl-9-hydroxy-6-methylellipticinium chloride

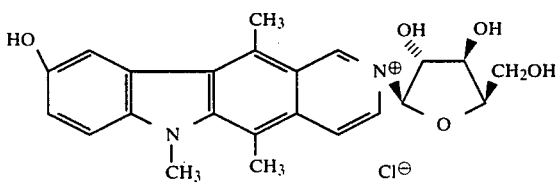

A 126 mg amount of 2-(2,3,5-tri-O-benzoyl-β-D-xylofuranosyl)-9-acetoxy-6-methylellipticinium chloride was dissolved in 38 ml of methanol saturated with gaseous ammonia and the mixture was allowed to stand at room temperature overnight. After concentrating in vacuo, the resultant residue was dissolved in 10 ml of hot methanol. Ethyl acetate was added to the solution to cause crystallization. The powder was collected by filtration and was washed with a solvent mixture of ethyl acetate and methanol (4:1). Thus, 63 mg (90% yield) of the desired compound was obtained.

The results are shown in Table 2.

Similarly, 2-β-L-xylofuranosyl-9-hydroxy-6-methylellipticinium chloride was obtained.

EXAMPLES 121 to 126

The following ellipticine derivatives were prepared in the same manner as in Example 120. The results are shown in Table 2.

Example 121:
2-β-D-ribofuranosyl-9-hydroxy-6-methylellipticinium bromide.
2-β-L-ribofuranosyl-9-hydroxy-6-methylellipticinium bromide.
Example 122:
2-α-L-arabinofuranosyl-9-hydroxy-6-methylellipticinium bromide.
2-α-D-arabinofuranosyl-9-hydroxy-6-methylellipticinium bromide.
Example 123:
2-(5-deoxy-α-L-arabinofuranosyl)-9-hydroxy-6-methylellipticinium chloride.
Example 124:
2-β-D-erythrofuranosyl-9-hydroxy-6-methylellipticinium chloride.
2-β-L-erythrofuranosyl-9-hydroxy-6-methylellipticinium chloride.
Example 125:
2-(5-deoxy-β-D-ribofuranosyl)-9-hydroxy-6-methylellipticinium chloride.

The following ellipticine derivatives were prepared in the same manner as in Example 109. The results are shown in Table 2.

Example 126:

2-β-D-arabinofuranosyl-9-hydroxy-6-methylellipticinium bromide.

2-β-L-arabinofuranosyl-9-hydroxy-6-methylellipticinium bromide.

EXAMPLE 127

Preparation of 2-(2,3,5-tri-O-benzoyl-D-lyxofuranosyl)-9-acetoxy-6-methylellipticinium chloride

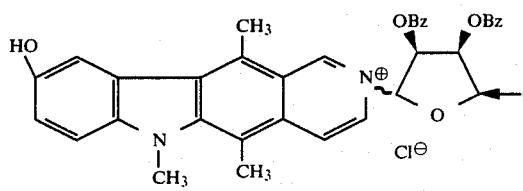

By using 150 mg of 9-acetoxy-6-methylellipticine and 424 mg of 2,3,5-tri-O-benzoyl-D-lyxofuranosyl chloride, 224 mg (60% yield) of the desired compound was prepared in the same manner as in Example 113.

This compound had two stereoisomers on the 1-position of the sugar at a ratio of the α-form/β-form=5/1. The data in Table 2 represent the values of the α- and β-form separately in NMR spectrum and the values of the mixture in the other items.

EXAMPLE 128

2-(2,3,5-tri-O-benzoyl-L-lyxofuranosyl)-9-acetoxy-6-methylellipticinium chloride was prepared in the same manner as in Example 127.

This compound also had two stereoisomers at the same ratio of α-/β-form as that of D-enantiomer. The physical data are shown in Table 2 as in Example 127.

EXAMPLE 129

Preparation of 2-D-lyxofuranosyl-9-hydroxy-6-methylellipticinium chloride

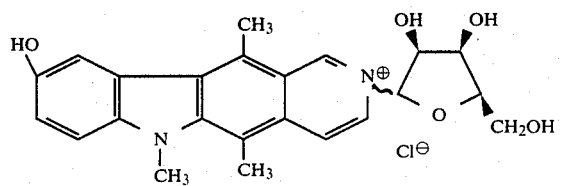

By using 203 mg of the compound obtained in Example 127, 84 mg (74% yield) of the desired compound was prepared in the same manner as in Example 120. This product was also a mixture of the α-form/β-form=5/1 with respect to the 1-position of the sugar.

The NMR data of the α- and β-form are separately shown and the other data represent those of the mixture of the α- and β-form in Table 2.

EXAMPLE 130

2-L-lyxofuranosyl-9-hydroxy-6-methylellipticinium chloride having the α-form/the β-form=5/1 was prepared in the same manner as in Example 129.

The results are shown in Table 2 as in Example 129.

EXAMPLE 131

Preparation of 2-(2,3,4-tri-O-acetyl-β-L-ribopyranosyl)-9-acetoxy-6-methylellipticinium bromide

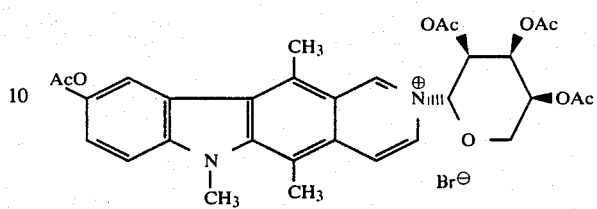

The reaction was carried out by using 100 mg of 9-acetoxy-6-methylellipticine, 288 mg of 2,3,4-tri-O-acetyl-β-L-ribopyranosyl bromide, 150 mg of cadmium carbonate, and 10 ml of nitromethane in the same manner as mentioned above. As a result, 206 mg of the desired compound was prepared.

The results are shown in Table 2.

EXAMPLE 132

2-(2,3,4-tri-O-acetyl-β-D-ribopyranosyl)-9-acetoxy-6-methylellipticinium bromide was prepared in the same manner as in Example 131.

The results are shown in Table 2.

EXAMPLE 133

Preparation of 2-(2,3,4-tri-O-acetyl-β-L-fucopyranosyl)-9-acetoxy-6-methylellipticinium bromide

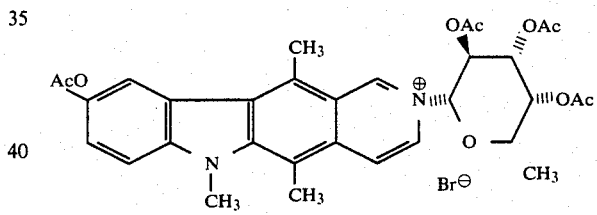

The reaction was carried out by using 100 mg of 9-acetoxy-6-methylellipticine, 220 mg of 2,3,4-tri-O-acetyl-L-fucopyranosyl bromide, 120 mg of cadmium carbonate, and 10 ml of nitromethane in the same manner as mentioned above. As a result 176 mg (84% yield) of the desired compound was obtained.

The results are shown in Table 2.

EXAMPLE 134

2-(2,3,4-tri-O-acetyl-β-D-fucopyranosyl)-9-acetoxy-6-methylellipticinium bromide was prepared in the same manner as in Example 133.

The results are shown in Table 2.

EXAMPLES 135 to 142

The following ellipticine derivatives were prepared in the same manner as in Examples 131 and 133. The results are shown in Table 2.

Example 135:
2-(2,3,4-tri-O-acetyl-β-D-arabinopyranosyl)-9-acetoxy-6-methylellipticinium bromide.

Example 136:
2-(2,3,4-tri-O-acetyl-β-L-arabinopyranosyl)-9-acetoxy-6-methylellipticinium bromide.

Example 137:

2-(2,3,4-tri-O-acetyl-α-D-lyxopyranosyl)-9-acetoxy-6-methylellipticinium chloride.

Example 138:

2-(2,3,4-tri-O-acetyl-α-L-lyxopyranosyl)-9-acetoxy-6-methylellipticinium chloride.

Example 139:

2-(2,3,4,6-tetra-O-acetyl-β-D-galactopyranosyl)-9-acetoxy-6-methylellipticinium bromide.

2-(2,3,4,6-tetra-O-acetyl-β-L-galactopyranosyl)-9-acetoxy-6-methylellipticinium bromide.

Example 140:

2-(2,3,4,6-tetra-O-acetyl-β-D-glucopyranosyl)-9-acetoxy-6-methylellipticinium bromide.

2-(2,3,4,6-tetra-O-acetyl-β-L-glucopyranosyl)-9-acetoxy-6-methylellipticinium bromide.

Example 141:

2-(2-acetamido-3,4,6-tri-O-acetyl-2-deoxy-β-D-glucopyranosyl)-9-acetoxy-6-methylellipticinium chloride.

Example 142:

2-(methyl 2,3,4-tri-O-acetyl-β-D-glucuronopyranosyl)-9-acetoxy-6-methylellipticinium bromide.

EXAMPLE 143

Preparation of 2-(2,3,4-tri-O-acetyl-D-xylopyranosyl)-9-acetoxy-6-methylellipticinium bromide

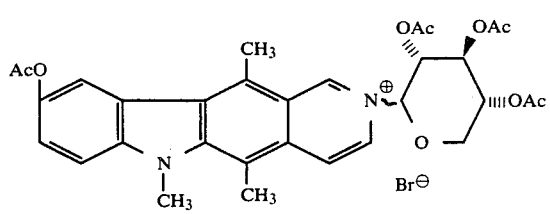

The reaction was carried out by using 100 mg of 9-acetoxy-6-methylellipticine, 210 mg of 2,3,4-tri-O-acetyl-α-D-xylopyranosyl bromide, 120 mg of cadmium carbonate, and 10 ml of nitromethane in the same manner as mentioned above. As a result, 107 mg (52% yield) of the desired compound was obtained.

This product had a mixture of two isomers of the α- and β-form with respect to the 1-position of the sugar at a ratio of α-form/β-form = $\frac{1}{3}$.

The NMR data of the α- and β-form are separately shown and the other data represent those of the mixture of the α- and β-form.

EXAMPLE 144

2-(2,3,4-tri-O-acetyl-L-xylopyranosyl)-9-acetoxy-6-methylellipticinium bromide was prepared in the same manner as in Example 143.

The ratio of α-form/β-form was $\frac{1}{3}$.

The physical data are shown in Table 2 as in Example 143.

EXAMPLE 145

Preparation of 2-β-L-ribopyranosyl-9-hydroxy-6-methylellipticinium bromide

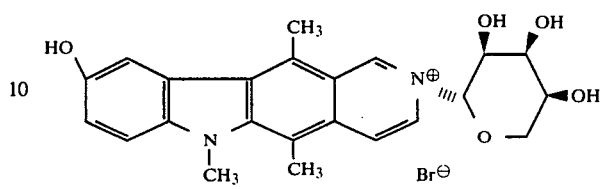

A 122 mg amount of the compound obtained in Example 131 was dissolved in 10 ml of methanol saturated with gaseous ammonia to effect the hydrolysis in the same manner as mentioned above. Thus, 53 mg (59% yield) of the desired compound was obtained.

The results are shown in Table 2.

EXAMPLE 147

2-β-D-ribopyranosyl-9-hydroxy-6-methylellipticinium bromide was prepared in the same manner as in Example 145. The results are shown in Table 2.

EXAMPLE 147

Preparation of 2-β-L-fucopyranosyl-9-hydroxy-6-methylellipticinium bromide

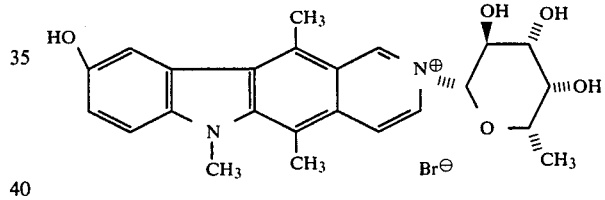

The reaction was carried out by using 153 mg of the compound obtained in Example 133 and 15 ml of methanol saturated with gaseous ammonia in the same manner as mentioned above. Thus, 82 mg (72% yield) of the desired compound was obtained.

The results are shown in Table 2.

EXAMPLE 148

2-β-D-fucopyranosyl-9-hydroxy-6-methylellipticinium bromide was prepared in the same manner as in Example 147.

The results are shown in Table 2.

EXAMPLE 149 to 155

The following ellipticine derivatives were prepared in the same manner as in Examples 145 and 147. The results are shown in Table 2.

Example 149:

2-α-D-arabinopyranosyl-9-hydroxy-6-methylellipticinium bromide.

Example 150:

2-α-L-arabinopyranosyl-9-hydroxy-6-methylellipticinium bromide.

Example 151:

2-α-D-lyxopyranosyl-9-hydroxy-6-methylellipticinium chloride.

Example 152:

2-α-L-lyxopyranosyl-9-hydroxy-6-methylellipticinium chloride.

Example 153:
2-β-D-galactopyranosyl-9-hydroxy-6-methylellipticinium bromide.
2-β-L-galactopyranosyl-9-hydroxy-6-methylellipticinium bromide.

Example 154:
2-β-D-glucopyranosyl-9-hydroxy-6-methylellipticinium bromide.
2-β-L-glucopyranosyl-9-hydroxy-6-methylellipticinium bromide.

Example 155:
2-(2-acetamido-2-deoxy-β-D-glucopyranosyl)-9-hydroxy-6-methylellipticinium chloride.

EXAMPLE 156

Preparation of 2-β-D-glucuronamidopyranosyl-9-hydroxy-6-methylellipticinium bromide

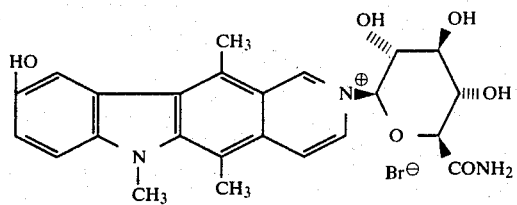

The compound of Example 142 was dissolved in methanol saturated with gaseous ammonia and the mixture was allowed to stand at a temperature of 0° C. to 5° C. for 15 hours in the same manner as mentioned above. Thus, the desired compound was obtained.

The results are shown in Table 2.

EXAMPLE 157

Preparation of 2-D-xylopyranosyl-9-hydroxy-6-methylellipticinium bromide

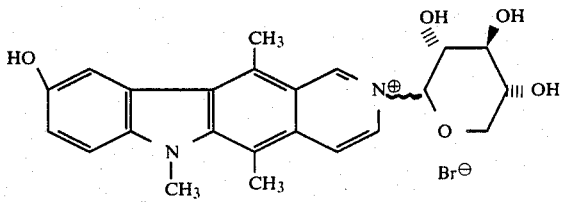

The reaction was carried out by using 84 mg of the compound obtained in Example 143 and 10 ml of methanol saturated with gaseous ammonia in the same manner as mentioned above. Thus, 41 mg (66% yield) of the desired compound having two isomers with respect to the 1-position of the sugar at a ratio of the β-form/the β-form = ⅓.

The NMR spectra of the α- and β-form, and the other physical data of the mixture are shown in Table 2.

EXAMPLE 158

2-L-xylopyranosyl-9-hydroxy-6-methylellipticinium bromide was prepared in the similar manner as in Example 157. The ratio of the α-form/β-form was also ⅓.

The NMR spectra of the α- and β-form, and the other properties of the mixture are shown in Table 2.

EXAMPLE 159

Preparation of 2-(2,3,4-tri-O-acetyl-α-L-rhamnopyranosyl)-9-hydroxy-6-methylellipticinium bromide

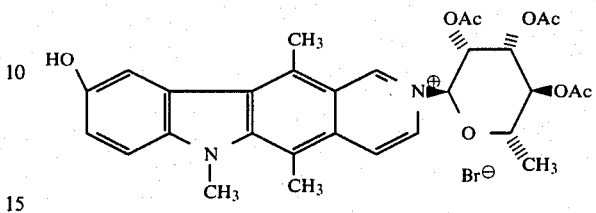

A 190 mg amount of 9-hydroxy-6-methylellipticine, 190 mg of cadmium carbonate, and 399 mg of α-bromoaceto-L-rhamnose were suspended in 19 ml of nitromethane and the suspension was heated under reflux for 10 minutes. After removing the insoluble matter, the reaction mixture was concentrated. The residue was subjected to column chromatography of 200 ml of silicagel (elution: methylene chloride-methanol = 95-:5-92:8) and Sephadex LH20 (4.0 cmφ×23 cm, methanol). Thus, 214 mg (49% yield) of the desired compound was obtained.

The results are shown in Table 2.

EXAMPLE 160

The following compound was prepared in the same manner as in Example 159. The results are shown in Table 2

2-(2,3,4,6-tetra-O-acetyl-β-D-mannopyranosyl)-9-hydroxy-6-methylellipticinium bromide 2-(2,3,4,6-tetra-O-acetyl-α-L-mannopyranosyl)-9-hydroxy-6-methylellipticinium bromide

EXAMPLE 161

Preparation of 2-α-L-rhamnopyranosyl-9-hydroxy-6-methylellipticinium bromide

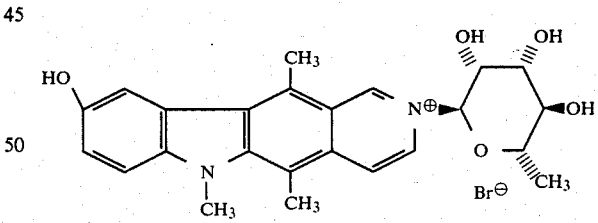

A 194 mg amount of the compound obtained in Example 159 was dissolved in 32 ml of methanol saturated with gaseous ammonia and the solution was allowed to stand in a refrigerator for 15 hours. Thus, 98 mg (79% yield) of the desired compound was obtained.

The results are shown in Table 2.

EXAMPLE 162

2-α-D-mannopyranosyl-9-hydroxy-6-methylellipticinium bromide and 2-α-L-mannopyranosyl-9-hydroxy-6-methylellipticinium bromide were prepared in the same manner as in Example 161.

The results are shown in Table 2.

EXAMPLE 163

Preparation of
2-(2,3,4-tri-O-acetyl-α-L-rhamnopyranosyl)-9-acetoxy-6-ethylellipticinium bromide

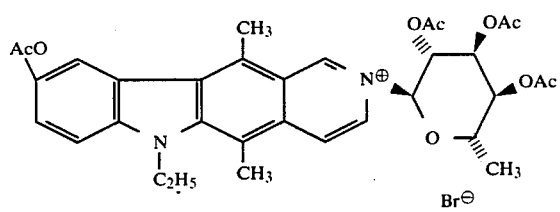

A 190 mg amount of 9-acetoxy-6-ethylellipticine, 170 mg of cadmium carbonate, and 292 mg (1.6 equivalent) of 2,3,4-tri-O-acetyl-α-L-rhamnopyranosyl bromide were suspended in 17 ml of nitromethane and was heated under reflux for 10 minutes. The insoluble matter was removed by filtration and the filtrate was concentrated. The residue thus obtained was subjected to silicagel column chromotography (silicagel 100 ml, elution solvent:methylene chloride:methanol=96:4–93:7) and Sephadex LH20 column chromatography (4 cm$\phi$×30 cm, methanol). Thus, 262 mg (75% yield) of the desired compound was obtained.

The results are shown in Table 2.

EXAMPLE 164

Preparation of
2-α-L-rhamnopyranosyl-9-hydroxy-6-ethylellipticinium bromide

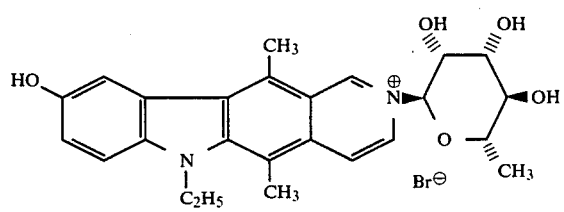

A 240 mg amount of the compound obtained in Example 163 was dissolved in 40 ml of methanol saturated with gaseous ammonia and was allowed to stand overnight in a refrigerator. The reaction mixture was concentrated and the resultant residue was powdered with methanolethyl acetate. Thus, 131 mg (72% yield) of the desired compound was obtained.

The results are shown in Table 2.

EXAMPLE 165

Preparation of
2-(2,3,4-tri-O-acetyl-α-L-rhamnopyranosyl)-9-acetoxy-6-isopropylellipticinium bromide

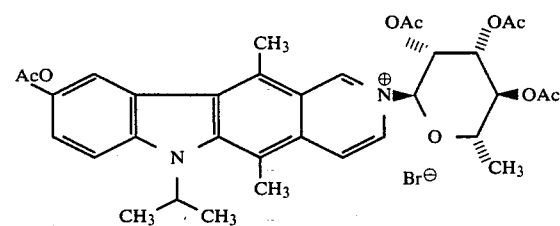

A 142 mg amount of 9-acetoxy-6-isopropylellipticine, 100 mg of cadmium carbonate, and 200 mg of 2,3,4-tri-O-acetyl-α-L-rhamnopyranosyl bromide were suspended in 12 ml of nitromethane and the mixture was heated under reflux for 10 minutes. After removing the insoluble matter by filtration, the filtrate was concentrated. The resultant residue was subjected to silicagel column chromatography (silicagel: 80 g, solvent: 5% methanol-chloroform) and, then, to Sephadex LH-20 column chromatography (4.8 cm$\phi$×27.5 cm, methanol). Thus, 152 mg (53% yield) of the desired compound was obtained.

The results are shown in Table 2.

EXAMPLE 166

Preparation of
2-α-L-rhamnopyranosyl-9-hydroxy-6-isopropylellipticinium bromide

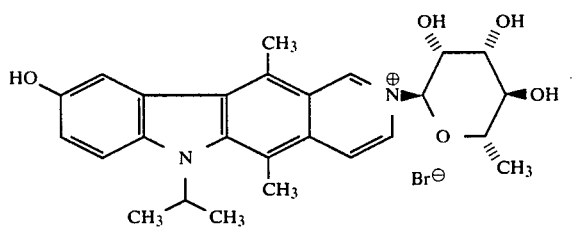

A 130 mg amount of the compound obtained in Example 165 was dissolved in 10 ml of methanol saturated with ammonia and was allowed to stand for 21 hours in a refrigerator. The residue obtained after concentrating was powdered with methanol-ethyl acetate. Thus, 70 mg (71% yield) of the desired compound was obtained.

The results are shown in Table 2.

EXAMPLE 167

Preparation of
2-(2,3,4-tri-O-acetyl-α-L-rhamnopyranosyl)-9-acetoxy-6-cyclopropylmethylellipticinium bromide

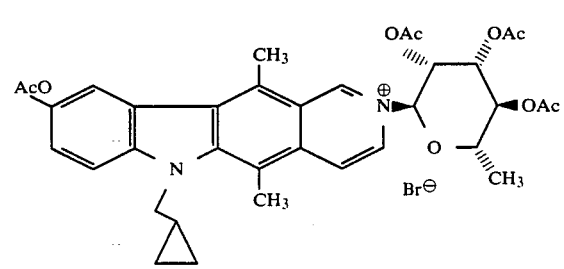

A 172 mg amount of 9-acetoxy-6-cyclopropylmethylellipticine, 170 mg of cadmium carbonate, and 275 mg of 2,3,4-tri-O-acetyl-α-L-rhamnopyranosyl bromide were suspended in 17 ml of nitromethane and the mixture was heated under reflux for 7 minutes. After removing the insoluble matter by filtration, the filtrate was concentrated. The residue thus obtained was subjected to silicagel column chromatography (gel: 100 ml, solvent: methylene chloride: methanol=95:5) and, then, to Sephadex LH-20 (2.5 cm$\phi$×53 cm, methanol). Thus, 259 mg (76% yield) of the desired compound was obtained.

The results are shown in Table 2.

EXAMPLE 168

Preparation of 2-α-L-rhamnopyranosyl-9-hydroxy-6-cyclopropylmethylellipticinium bromide

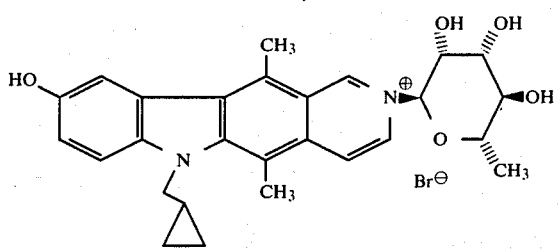

A 184 mg amount of the compound obtained in Example 167 was dissolved in 32 ml of methanol saturated with ammonia and was allowed to stand overnight in a refrigerator. After concentrating, the resultant residue was crystallized from methanol-ethyl acetate. Thus, 122 mg (87% yield) of the desired compound was obtained. The results are shown in Table 2.

EXAMPLE 169 to 172

The following ellipticine derivatives were prepared in the same manner as mentioned above. The results are shown in Table 2.

Example 169:
2-(2,3,4-tri-O-acetyl-α-L-rhamnopyranosyl)-6-methylellipticinium bromide Example 170:
2-α-L-rhamnopyranosyl-6-methylellipticinium bromide Example 171:
2-(2,3,4-tri-O-acetyl-αL-rhamnopyranosyl)-9-methoxy-6-methylellipticinium bromide.

Example 172: 2-α-L-rhamnopyranosyl-9-methoxy-6-methylellipticinium bromide.

REFERENCE EXAMPLE 1

Synthesis of 9-Hydroxy-6-isopropylellipticine

A 1.0 g amount of 9-acetoxyellipticine was dissolved in 40 ml of anhydrous dimethylformamide and, then, to this solution, 160 ml of sodium hydride (50% in oil) and 10 ml of anhydrous dimethylformamide were added at a temperature of 0° C. The mixture was stirred for 30 minutes. To this reaction mixture, 0.33 ml of isopropyl iodide was added at a temperature of 0° C. and the mixture was then stirred at room temperature for 43 hours. Ice water was added to the reaction mixture and the mixture was extracted 4 times with chloroform. After the organic layer was washed with water, the organic layer was dried over anhydrous magnesium sulfate. The mixture was concentrated to form the residue. The residue thus obtained was subjected to silicagel column chromatography and eluted with 1% methanol-chloroform solvent. Thus, 268 mg (24% yield) of 9-acetoxy-6-isopropylellipticine was obtained.

The compound thus obtained was treated with methanol saturated with ammonia at a temperature of 0° C. to 5° C. for 15 hours to obtain the desired compound at a yield of 22%. The physical data is as follows:

Crystalline form: prism crystal (yellowish brown)
Melting point: 270°–285° C. (sublimation with decomposition).

IR spectrum (KBr, cm$^{-1}$): 1600, 1590, 1580, 1500, 1465, 1390, 1380, 1370, 1280, 1270, 1260, 1210, 1170, 1145, 1135, 1125, 1100, 1025.

UV spectrum ($\lambda_{max}^{C_2H_5OH}$, nm): 212(ε26,000), 250(ε30,000) 277(ε40,000), 298(ε55,000).

Mass spectrum (EI, m/z): 304(M+), 288, 261, 247, 233, 217, 77, 28.

NMR spectrum (DMSO-d$_6$, δppm): 1.57(6H, d, J=7 Hz), 2.91(3H, s) 3.18(3H, s), 5.27(1H, dq, J=7 Hz), 7.01(1H, dd, J=2.5, 8.5 Hz), 7.62(1H, d, J=8.5 Hz), 7.79(1H, d, J=2.5 Hz), 7.94(1H, d, J=6.5 Hz), 8.42(1H, d, J=6.5 Hz), 9.19(1H, s), 9.65(1H, s). Elementary analysis (C$_{20}$H$_{20}$N$_2$O)

|  | C(%) | H(%) | N(%) |
| --- | --- | --- | --- |
| Calc.: | 78.92 | 6.62 | 9.20 |
| Found: | 78.80 | 6.42 | 9.10 |

REFERENCE EXAMPLE 2

Synthesis of 9-Acetoxy-6-Cyclopropylmethylellipticine

A 1.0 g amount of 9-acetoxyellipticine was dissolved in 40 ml of anhydrous dimethylformamide and, then, to this solution, 131 mg of sodium hydride was added. The mixture was stirred at room temperature for 10 minutes. To this reaction mixture, a solution of 442 mg of bromomethylcyclopropane in 1 ml of anhydrous dimethylformamide was added. The mixture was then stirred at room temperature for 6 hours. Water was added to the reaction mixture to form the precipitated powder. After the powder was separated by filtration and was subjected to silicagel column chromatography (gel: 200 ml, 1% methanol-chloroform). Thus, 577 mg (49% yield) of the desired compound was obtained.

Crystalline form: Yellow needle-like crystal.
Melting point: 200°–205° C.

IR spectrum (KBr, cm$^{-1}$): 3000, 2920, 1740, 1595, 1480, 1370, 1300, 1220, 1200, 1140, 1010.

UV spectrum ($\lambda_{max}^{C_2H_5OH}$, nm): 205(ε16,000), 220(ε16,000), 250(ε23,000), 278(ε38,000), 290(ε53,000), 298(ε60,000).

Mass spectrum (EI, m/z): 358M+), 316, 232, 204.

NMR spectrum (DMSO-d$_6$, δppm): 0.33–0.47(4H, m), 1.22(1H, m), 2.34(3H, s), 3.04(3H, s), 3.19(3H, s), 4.62(2H, d, J=6 Hz), 7.34(1H, dd, J=2, 9 Hz), 7.71(1H, d, J=9 Hz), 8.04(1H, d, J=6.5 Hz), 8.11(1H, d, J=2 Hz), 8.46(1H, d, J=6.5 Hz), 9.71(1H, s).

| Elementary analysis (C$_{23}$H$_{22}$N$_2$O$_2$) | | | |
| --- | --- | --- | --- |
|  | C(%) | H(%) | N(%) |
| Calc.: | 77.07 | 6.19 | 7.82 |
| Found: | 77.05 | 6.21 | 7.89 |

EVALUATION TEST

The antineoplastic or antitumor activity of the various ellipticine derivatives listed in Table 3 prepared above was evaluated, by using mouse experimental tumor L-1210, as follows:

(i) Animal used:
BDF$_1$ mouse, female, 6 weeks ago, average body weight of 17 to 18 g, 6 mice in one group (ii) Type of tumor used:
L 1210 (mouse lymphoid leukemia cells ) 10$^5$ cells/mouse, intraperitoneally injection (ip)

(iii) Sample administration method:

L 1210 was intraperitoneally injected into mice and the sample was successively administered once a day for 5 days from the second day after the injection of L 1210 cells.

(iv) Evaluation method:

The effectivity of the sample was determined in increased life span of mean survival day of the administered group (ILS%) when compared with the control group.

$$ILS(\%) = \frac{\text{Mean survival day of the administered group}}{\text{Mean survival day of the control group}} - 1 \times 100$$

The results were shown in Table 3. From the results shown in Table 3, it is clear that the present ellipticine derivatives have excellent or remarkable antineoplastic or antitumor effects against mouse lymphoid leukemia L 1210. Thus, it is believed that the present ellipticine derivatives are effective as an antitumor agent.

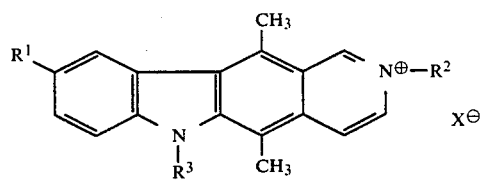

TABLE 3

| Example No. (R²) | Dose (mg/kg) | Toxicity | ILS % | 80 days' survival |
|---|---|---|---|---|
| Control | 0 | 0/6 | 0 | 0/6 |
| 2 | 20 | 0/6 | 33.8 | 0/6 |
| D-galactopyranosyl | 40 | 0/6 | 39.0 | 0/6 |
|  | 80 | 6/6 | toxic | 0/6 |
| 4 | 10 | 0/6 | 57.8 | 0/6 |
| D-ribofuranosyl | 20 | 0/6 | 80.0 | 0/6 |
| 12 | 10 | 0/6 | 28.9 | 0/6 |
| L-rhamnopyranosyl | 20 | 0/6 | 37.8 | 0/6 |
|  | 40 | 0/6 | 40.0 | 0/6 |
| 18 | 5 | 0/6 | 53.3 | 0/6 |
| D-ribofuranosyl | 10 | 0/6 | 60.0 | 0/6 |
|  | 30 | 0/6 | 75.6 | 0/6 |
| 26 | 5 | 0/6 | 44.4 | 0/6 |
| L-rhamnopyranosyl | 10 | 0/6 | 62.5 | 0/6 |
| 53 | 10 | 0/6 | 53.3 | 0/6 |
| L-rhamnopyranosyl | 30 | 0/6 | 68.8 | 0/6 |
|  | 60 | 0/6 | 88.8 | 0/6 |
| 62 | 5 | 0/6 | 62.2 | 0/6 |
| D-galactopyranosyl | 10 | 0/6 | 86.7 | 0/6 |
|  | 20 | 0/6 | >728.9 | 4/6 |
|  | 40 | 6/6 | toxic | 0/6 |
| 63 | 5 | 0/6 | >209.6 | 1/6 |
| L-arabinofuranosyl | 10 | 0/6 | >378.7 | 2/6 |
|  | 30 | 6/6 | toxic | 0/6 |
| 64 | 2.5 | 0/6 | 56.8 | 0/6 |
| D-arabinofuranosyl | 5 | 0/6 | 61.4 | 0/6 |
|  | 10 | 0/6 | 72.7 | 0/6 |
|  | 20 | 0/6 | 90.9 | 0/6 |
| 66 | 5 | 0/6 | 56.8 | 0/6 |
| D-mannopyranosyl | 10 | 0/6 | 87.7 | 0/6 |
|  | 30 | 6/6 | toxic | 0/6 |
| 66 | 5 | 0/6 | >361.7 | 2/6 |
| L-mannopyranosyl | 10 | 0/6 | >243.6 | 1/6 |
|  | 30 | 0/6 | 4.3 | 0/6 |
| 67 | 5 | 0/6 | 95.7 | 0/6 |
| D-talopyranosyl | 10 | 0/6 | >211.3 | 1/6 |
|  | 30 | 6/6 | toxic | 0/6 |
| 68 | 0.1 | 0/6 | 6.7 | 0/6 |
| L-galactopyranosyl | 0.5 | 0/6 | 28.6 | 0/6 |
|  | 2.5 | 0/6 | 57.1 | 0/6 |
| 69 | 5 | 4/6 | toxic | 0/6 |
|  | 5 | 0/6 | 97.8 | 0/6 |
| D-allopyranosyl | 10 | 0/6 | >254.4 | 2/6 |
|  | 30 | 2/6 | toxic | 0/6 |
| 70 | 5 | 0/6 | 58.4 | 0/6 |
| L-glucopyranosyl | 10 | 0/6 | 14.3 | 0/6 |
|  | 30 | 6/6 | toxic | 0/6 |
| 71 | 5 | 0/6 | 68.9 | 0/6 |
| L-rhamnopyranosyl | 10 | 0/6 | 95.6 | 0/6 |
|  | 30 | 0/6 | >693.3 | 4/6 |
| 72 | 5 | 0/6 | 78.1 | 0/6 |
| 2-deoxy-D- | 10 | 0/6 | >390.4 | 2/6 |
| ribofuranosyl | 20 | 0/6 | >200.0 | 1/6 |
| 73 | 5 | 0/6 | 46.7 | 0/6 |
| 5-deoxy- | 10 | 0/6 | 80.0 | 0/6 |
| D-ribofuranosyl | 30 | 0/6 | >230.0 | 1/6 |
| 74 | 5 | 0/6 | 82.2 | 0/6 |
| 5-deoxy-L- | 10 | 0/6 | 73.3 | 0/6 |
| arabinofuranosyl | 30 | 0/6 | >261.1 | 1/6 |
| 75 | 5 | 0/6 | 54.4 | 0/6 |
| D-fucopyranosyl | 10 | 0/6 | 68.9 | 0/6 |
|  | 30 | 0/6 | 124.4 | 0/6 |
| 76 | 5 | 0/6 | 62.2 | 0/6 |
| L-fucopyranosyl | 10 | 0/6 | 117.8 | 0/6 |
|  | 30 | 0/6 | >583.3 | 3/6 |
| 77 | 5 | 0/6 | 117.8 | 0/6 |
| D-xylofuranosyl | 10 | 0/6 | >384.4 | 2/6 |
|  | 30 | 0/6 | >682.2 | 4/6 |
| 77 | 5 | 0/6 | 97.8 | 0/6 |
| L-xylofuranosyl | 10 | 0/6 | >227.8 | 1/6 |
|  | 30 | 0/6 | >386.7 | 2/6 |
| 79 | 5 | 0/6 | 122.2 | 0/6 |
| D-erythrofuranosyl | 10 | 0/6 | 4.7 | 0/6 |
|  | 30 | 0/6 | toxic | 0/6 |
| 80 | 5 | 0/6 | 87.0 | 0/6 |
| L-ribopyranosyl | 10 | 0/6 | >512.0 | 3/6 |
|  | 30 | 0/6 | >943.5 | 6/6 |
| 81 | 5 | 0/6 | 57.5 | 0/6 |
| D-ribopyranosyl | 10 | 0/6 | 75.3 | 0/6 |
|  | 30 | 0/6 | 112.3 | 0/6 |
| 82 | 5 | 0/6 | 106.7 | 0/6 |
| L-ribofuranosyl | 10 | 0/6 | >391.1 | 2/6 |
|  | 30 | 0/6 | 2.2 | 0/6 |
| 83 | 5 | 0/6 | 86.7 | 0/6 |
| D-ribofuranosyl | 10 | 0/6 | 137.8 | 0/6 |
|  | 30 | 0/6 | toxic | 0/6 |
| 84 | 2.5 | 0/6 | 77.3 | 0/6 |
| D-arabinopyranosyl | 5 | 0/6 | 93.2 | 0/6 |
|  | 10 | 0/6 | >381.8 | 2/6 |
|  | 20 | 0/6 | >605.7 | 3/6 |
| 85 | 5 | 0/6 | 76.4 | 0/6 |
| L-arabinopyranosyl | 10 | 0/6 | 115.3 | 0/6 |
|  | 30 | 0/6 | >839.4 | 5/6 |
| 86 | 5 | 0/6 | >191.0 | 1/6 |
| D-lyxofuranosyl | 10 | 0/6 | >675.6 | 4/6 |
|  | 30 | 0/6 | >966.7 | 6/6 |
| 87 | 5 | 0/6 | >234.4 | 1/6 |
| L-lyxofuranosyl | 10 | 0/6 | >552.2 | 3/6 |
|  | 30 | 0/6 | — | 0/6 |
| 88 | 5 | 0/6 | 83.3 | 0/6 |
| L-lyxopyranosyl | 10 | 0/6 | >213.8 | 1/6 |
|  | 30 | 0/6 | >786.2 | 5/6 |
| 89 | 5 | 0/6 | 121.8 | 0/6 |
| D-lyxopyranosyl | 10 | 0/6 | >651.1 | 4/6 |
|  | 30 | 6/6 | toxic | 0/6 |
| 90 | 5 | 0/6 | 6.5 | 0/6 |
| 2-acetamido-2- | 10 | 0/6 | 19.5 | 0/6 |
| deoxy-D-glucopyranosyl | 30 | 0/6 | 39.0 | 0/6 |
| 92 | 5 | 0/6 | 48.9 | 0/6 |
| D-glucuronamido- | 10 | 5/6 | toxic | 0/6 |
| pyranosyl | 30 | 6/6 | toxic | 0/6 |
| 93 | 5 | 0/6 | 77.8 | 0/6 |
| D-xylopyranosyl | 10 | 0/6 | >248.6 | 1/6 |
|  | 30 | 0/6 | >805.3 | 5/6 |
| 94 | 5 | 0/6 | >385.1 | 2/6 |
| L-xylopyranosyl | 10 | 0/6 | >395.7 | 2/6 |
|  | 30 | 6/6 | toxic | 0/6 |
| 95 | 5 | 0/6 | 81.2 | 0/6 |

TABLE 3-continued

Results of Screening Test (L 1210)

| Example No. (R²) | Dose (mg/kg) | Toxicity | ILS % | 80 days' survival |
|---|---|---|---|---|
| L-rhamnopyranosyl | 10 | 0/6 | 127.3 | 0/6 |
| | 30 | 0/6 | >614.8 | 3/6 |
| 96 | 5 | 0/6 | 71.2 | 0/6 |
| β-D-arabinofuranosyl | 10 | 0/6 | 80.8 | 0/6 |
| | 30 | 0/6 | >261.6 | 1/6 |
| 96 | 5 | 0/6 | 64.4 | 0/6 |
| β-L-arabinofuranosyl | 10 | 0/6 | >239.7 | 1/6 |
| | 30 | 0/6 | >268.5 | 1/6 |
| 97 | 5 | 0/6 | 72.2 | 0/6 |
| 5-deoxy-β-L-arabino- | 10 | 0/6 | >216.7 | 1/6 |
| furanosyl | 30 | 0/6 | >216.7 | 1/6 |
| 112 | 5 | 0/6 | 35.9 | 0/6 |
| D-glucopyranosyl | 10 | 0/6 | 52.4 | 0/6 |
| | 30 | 4/6 | toxic | 0/6 |
| 120 | 5 | 0/6 | 75.6 | 0/6 |
| D-xylofuranosyl | 10 | 0/6 | 86.7 | 0/6 |
| | 30 | 0/6 | >554.4 | 3/6 |
| 121 | 5 | 0/6 | 74.0 | 0/6 |
| D-ribofuranosyl | 10 | 0/6 | 101.4 | 0/6 |
| | 20 | 0/6 | 308.2 | 1/6 |
| 122 | 5 | 0/6 | 65.8 | 0/6 |
| L-arabinofuranosyl | 10 | 0/6 | 270.7 | 1/6 |
| | 30 | 0/6 | 644.0 | 3/6 |
| 123 | 5 | 0/6 | 69.3 | 0/6 |
| 5-deoxy-L-arabino- | 10 | 0/6 | 66.7 | 0/6 |
| furanosyl | 30 | 0/6 | 80.0 | 0/6 |
| 124 | 5 | 0/6 | 61.4 | 0/6 |
| D-erythrofuranosyl | 10 | 0/6 | 84.1 | 0/6 |
| | 30 | 0/6 | 4.5 | 0/6 |
| 129 | 5 | 0/6 | 76.7 | 0/6 |
| D-lyxofuranosyl | 10 | 0/6 | 84.9 | 0/6 |
| | 30 | 0/6 | >300.0 | 1/6 |
| 145 | 5 | 0/6 | -54.8 | 0/6 |
| L-ribopyranosyl | 10 | 0/6 | 57.5 | 0/6 |
| | 30 | 0/6 | >265.3 | 1/6 |
| 147 | 5 | 0/6 | 59.1 | 0/6 |
| L-fucopyranosyl | 10 | 0/6 | >235.2 | 1/6 |
| | 30 | 0/6 | >420.5 | 2/6 |
| 149 | 5 | 0/6 | 108.9 | 0/6 |
| D-arabinopyranosyl | 10 | 0/6 | >576.7 | 3/6 |
| | 30 | 5/6 | toxic | 0/6 |
| 150 | 5 | 0/6 | 62.2 | 0/6 |
| L-arabinopyranosyl | 10 | 0/6 | 113.3 | 0/6 |
| | 30 | 0/6 | >314.4 | 1/6 |
| 151 | 5 | 0/6 | 74.0 | 0/6 |
| D-lyxopyranosyl | 10 | 0/6 | 76.7 | 0/6 |
| | 30 | 0/6 | 17.4 | 0/6 |
| 152 | 5 | 0/6 | 93.2 | 0/6 |
| L-lyxopyranosyl | 10 | 0/6 | 115.1 | 0/6 |
| | 30 | 0/6 | >501.4 | 2/6 |
| 153 | 5 | 0/6 | 33.3 | 0/6 |
| D-galactopyranosyl | 10 | 0/6 | 66.7 | 0/6 |
| | 30 | 6/6 | toxic | 0/6 |
| 154 | 5 | 0/6 | 46.7 | 0/6 |
| D-glucopyranosyl | 10 | 0/6 | 80.0 | 0/6 |
| | 30 | 4/6 | toxic | 0/6 |
| 156 | 5 | 0/6 | 31.1 | 0/6 |
| D-glucuronamido- | 10 | 0/6 | 48.9 | 0/6 |
| pyranosyl | 30 | 5/6 | toxic | 0/6 |
| 157 | 5 | 0/6 | 112.5 | 0/6 |
| D-xylopyranosyl | 10 | 0/6 | 97.7 | 0/6 |
| | 30 | 0/6 | >848.9 | 5/6 |
| 161 | 5 | 0/6 | 75.5 | 0/6 |
| L-rhamnopyranosyl | 10 | 0/6 | 126.7 | 0/6 |
| | 30 | 0/6 | >500.0 | 2/6 |
| 162 | 5 | 0/6 | 67.7 | 0/6 |
| D-mannopyranosyl | 10 | 0/6 | 84.5 | 0/6 |
| | 30 | 6/6 | toxic | 0/6 |
| 164 | 5 | 0/6 | 32.0 | 0/6 |
| L-rhamnopyranosyl | 10 | 0/6 | 53.7 | 0/6 |
| | 30 | 0/6 | 64.0 | 0/6 |
| Ellipticine | 120 | 0/6 | 127.5 | 0/6 |
| 9-Methoxyellipticine | 30 | 0/6 | 27.3 | 0/6 |
| 9-Hydroxyellipticine | 60 | 0/6 | 78.6 | 0/6 |
| Celiptium | 5 | 0/6 | 47.8 | 0/6 |
| Adriamycin | 0.25 | 0/6 | 84.8 | 0/6 |

We claim:

1. A ellipticine derivative having the formula:

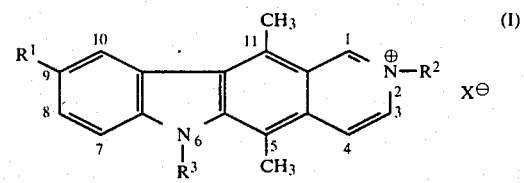

wherein

R¹ represents a hydrogen atom, a hydroxyl group, an alkoxyl group having 1 to 4 carbon atoms, or an acyloxy group having 2 to 7 carbon atoms;

R² represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid residue having, substituted for the hydrogen atom of the hydroxyl group of the sugar, an alkylacyl group with 2 to 4 carbon atoms or an arylacyl group with 7 to 9 carbon atoms, an acylated aldohexuronic acid ester residue having, substituted for the hydrogen atom of the hydroxyl group of the sugar, an alkylacyl group with 2 to 4 carbon atoms or an arylacyl group with 7 to 9 carbon atoms, an arylalkylated aldose residue having, substituted for the hydrogen atom of the hydroxyl group of the sugar, an arylalkyl group with 7 to 8 carbon atoms, an arylalkylated deoxyaldose residue having, substituted for the hydrogen atom of the hydroxyl group of the sugar, an alkylacyl group with 7 to 8 carbon atoms, an arylalkylated N-acylaminoaldose residue having an amino group with an acyl group with 2 to 4 carbon atoms and having, substituted for the hydrogen of the hydroxyl group of the sugar, an arylalkyl group with 7 to 8 carbon atoms, an arylalkylated aldohexuronic amide residue having, substituted for the hydrogen atom of the hydroxyl group of the sugar, an arylalkyl group with 7 to 8 carbon atoms, an arylalkylated aldohexuronic acid residue having, substituted for the hydrogen atom of the hydroxyl group of the sugar, an arylalkyl group with 7 to 8 carbon atoms, or an arylalkylated aldohexuronic acid ester residue having, substituted for the hydrogen atom of the hydroxyl group of the sugar, an arylalkyl group with 7 to 8 carbon atoms; and R³ represents a hydrogen atom, a linear, branched, cyclic, or cyclic-linear alkyl group having 1 to 5 carbon atoms;

X⊖ represents a pharmaceutically acceptable inorganic or organic acid anion; and the bond represented by N⊕—R² in the formula (I) represents a glycoside bond between a nitrogen atom in the 2-position of the ellipticine and a carbon atom in the 1-position of the sugar.

2. An ellipticine derivative as claimed in claim 1, wherein R² in the general formula (I) represents an aldotetrose residue, an acylated aldotetrose residue having, substituted for the hydrogen atom of the hydroxyl group of the sugar, an alkylacyl group with 2 to 4 carbon atoms or an arylacyl group with 7 to 9 carbon atoms, or an arylalkylated aldotetrose residue having an arylalkyl group with 7 to 8 carbon atoms substituted for the hydrogen atom of the hydroxyl group of the sugar.

3. An ellipticine derivative as claimed in claim 1, wherein R² in the formula (I) represents an aldopentose residue, an acylated aldopentose residue having, substituted for the hydrogen atom of the hydroxyl group of the sugar, an alkylacyl group with 2 to 4 carbon atoms or an arylacyl group with 7 to 9 carbon atoms, or an arylalkylated aldopentose residue having an arylalkyl group with 7 to 8 carbon atoms substituted for the hydrogen atom of the hydroxyl group of the sugar.

4. An ellipticine derivative as claimed in claim 1, R² in the formula (I) represents an aldohexose residue, an acylated aldohexose residue having, substituted for the hydrogen atom of the hydroxyl group of the sugar, an alkylacyl group with 2 to 4 carbon atoms or an arylacyl group with 7 to 9 carbon atoms, or an arylalkylated aldohexose residue having, substituted for the hydrogen atom of the hydroxyl group of the sugar, an arylalkyl group with 7 to 8 carbon atoms.

5. An ellipticine derivative as claimed in claim 1, wherein R² in the formula (I) represents a 2-deoyaldopentose residue, an acylated 2-deoxyaldopentose residue having, substituted for the hydrogen atom of the hydroxyl group of the sugar, with an alkylacyl group with 2 to 4 carbon atoms or an arylacyl group with 7 to 9 carbon atoms, or an arylalkylated 2-deoxyaldopentose residue having an arylalkyl group with 7 to 8 carbon atoms substituted for the hydrogen atom of the hydroxyl group of the sugar.

6. An ellipticine derivative as claimed in claim 1, wherein R² in the formula (I) represents a 2-deoxyaldohexose residue, an acylated 2-deoxyaldohexose residue having, substituted for the hydrogen atom of the hydroxyl group of the sugar, an alkylacyl group with 2 to 4 carbon atoms or an arylacyl group with 7 to 9 carbon atom, or an arylalkylated 2-deoxyaldohexose residue having an arylalkyl group with 7 to 8 carbon atoms substituted for the hydrogen atom of the hydroxyl group of the sugar.

7. An ellipticine derivative as claimed in claim 1, wherein R² is the formula (I) represents a 5-deoxyaldopentose residue, an acylated 5-deoxyaldopentose residue having, substituted for the hydrogen atom of the hydroxyl group of the sugar, an alkylacyl group with 2 to 4 carbon atoms or an arylacyl group with 7 to 9 carbon atoms, or an arylalkylated 5-deoxyaldopentose residue having, substituted for the hydrogen atom of the hydroxyl group of the sugar, an arylalkyl group with 7 to 8 carbon atoms.

8. An ellipticine derivative as claimed in claim 1, wherein R² is the formula (I) represents a 6-deoxyaldohexose residue, an acylated 6-deoxyaldohexose residue having, substituted for the hydrogen atom of the hydroxyl group of the sugar, an alkylacyl group with 2 to 4 carbon atoms or an arylacyl group with 7 to 9 carbon atoms, or an arylalkylated 6-deoxyaldohexose residue having, substituted for the hydrogen atom of the hydroxyl group of the sugar, an arylalkyl group with 7 to 8 carbon atoms.

9. An ellipticine derivative as claimed in claim 1, wherein R² is the formula (I) represents an N-acylaminoaldohexose residue having an amino group substituted with an acyl group with 2 to 4 carbon atoms, an acylated N-acylaminoaldohexose residue having an amino group substituted with an acyl group with 2 to 4 carbon atoms and having, substituted for the hydrogen atom or the hydroxyl group of the sugar, an alkylacyl group with 2 to 4 carbon atoms or an arylacyl group with 7 to 9 carbon atoms, or an arylalkylated N-acylaminoaldohexose residue having an acyl group substituted with an amino group with 2 to 4 carbon atoms having, substituted for the hydrogen atom of the hydroxyl group of the sugar, an arylalkyl group with 7 to 8 carbon atoms.

10. An ellipticine derivative as claimed in claim 1, wherein R² in the formula (I) represents an aldohexuronic acid residue, an aldohexuronic amide residue, an acylated aldohexuronic amide residue having, substituted for the hydrogen atom of the hydroxyl group of the sugar, an alkyacyl group with 2 to 4 carbon atoms or an arylacyl group with 7 to 9 carbon atoms, an acylated aldohexuronic acid residue having, substituted for the hydrogen atom of the hydroxyl group of the sugar, an alkylacyl group with 2 to 4 carbon atoms or an arylacyl group with 7 to 9 carbon atoms, an acylated aldohexuronic acid-lower alkyl ester residue having, substituted for the hydrogen atom of the hydroyl group of the sugar, an alkylacyl group with 2 to 4 carbon atoms or an arylacyl group with 7 to 9 carbon atoms, an arylalkylated aldohexuronic amide residue having, substituted for the hydrogen atom of the hydroxyl group of the sugar, an arylalkyl group with 7 to 8 carbon atoms, an arylalkylated aldohexuronic acid residue having, substituted for the hydrogen atom of the hydroxyl group of the sugar, an arylalkyl group with 7 to 8 carbon atoms, or an arylalkylated aldohexuronic acid-lower alkyl ester residue having, substituted for the hydrogen atom of the hydroxyl group of the sugar, an arylalkyl group with 7 to 8 carbon atoms.

11. An ellipticine derivative as claimed in claim 1, wherein X⊖ in the formula (I) is an anion derived from an inorganic acid selected from the group consisting of hydrochloric acid, sulfuric acid, phosphoric acid, hydroidic acid, hydrobromic acid, and perchloric acid or an anion derived from an organic acid selected from the group consisting of acetic acid, propionic acid, oxalic acid, tartaric acid, lactic acid, malic acid, formic acid, fumaric acid, maleic acid, butyric acid, valeric acid, caproic acid, heptanoic acid, and capric acid.

12. An ellipticine derivative as claimed in claim 1, wherein R³ in the formula (I) represents a methyl group, an ethyl group, a propyl group, an isopropyl group, a butyl group, an isobutyl group, a sec-butyl group, a pentyl group, a cyclopropylmethyl group, or a cyclopropylethyl group.

13. A process for producing an ellipticine derivative having the formula (Ia):

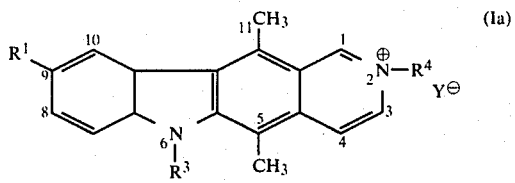 (Ia)

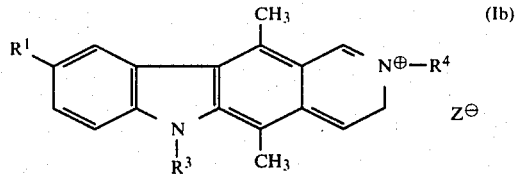 (Ib)

wherein
- $R^1$ represents a hydrogen atom, a hydroxyl group, an alkoxyl group having 1 to 4 carbon atoms, or an acyloxy group having 2 to 7 carbon atoms;
- $R^3$ represents a hydrogen atom, a linear, branched, cyclic, or cyclic-linear alkyl group having 1 to 5 carbon atoms;
- $R^4$ represents an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom or the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom or the hydroxyl group of the sugar, an alkylacyl group with 2 to 4 carbon atoms or an arylacyl group with 7 to 9 carbon atoms, an acylated aldohexuronic acid ester residue having, substituted for the hydrogen atom of the hydroxyl group of the sugar, an alkylacyl group with 2 to 4 carbon atoms or an arylacyl group with 7 to 9 carbon atoms, an arylalkylated aldose residue having, substituted for the hydrogen atom of the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated N-acylaminoaldose residue having an amino group with an acyl group with 2 to 4 carbon atoms and having, substituted for the hydrogen atom or the hydroxyl group of the sugar, an arylalkyl group with 7 to 8 carbon atoms, an arylalkylated aldohexuronic amide residue having, substituted for the hydrogen atom of the hydroxyl group of the sugar, an arylalkyl group with 7 to 8 carbon atoms, or an arylalkylated aldohexuronic acid ester residue having, substituted for the hydrogen atom of the hydroxyl group of the sugar, an arylalkyl group with 7 to 8 carbon atoms;
- Y represents a halogen atom; and
- the bond represented by $N^+$—$R^4$ in the formula (Ia) represents a glycoside bond between a nitrogen atom in the 2-position of the ellipticine and a carbon atom in the 1-position of the sugar, or the formula (Ib):

wherein
$R^1$, $R^3$, and $R^4$ are the same as defined above and $Z^\ominus$ is a pharmaceutically acceptable inorganic or organic acid anion; which comprises reacting a compound having the formula (II):

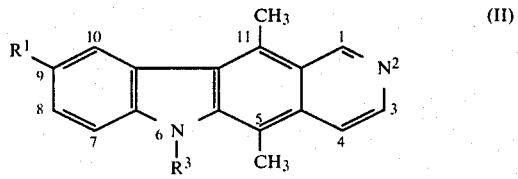 (II)

wherein
$R^1$ and $R^3$ are the same as defined above with an aldose derivative having the formula (III):

$$R^4-Y \qquad (III)$$

wherein
$R^4$ and Y are the same as defined above;
in the presence or absence of an acid captured reagent in an organic solvent to form an ellipticine derivative having the formula (Ia), which may be optionally subjected to an ion-exchange reaction with an ion-exchange resin to form an ellipticine derivative having the formula (Ib).

14. A process for producing an ellipticine derivative having the formula (Ic):

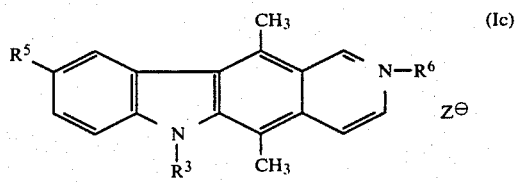 (Ic)

wherein
- $R^3$ represents a hydrogen atom, a linear, branched, cyclic, or cyclic-linear alkyl group having 1 to 5 carbon atoms;
- $R^5$ represents a hydrogen atom, a hydroxyl group, or an alkoxy group having 1 to 4 carbon atoms;
- $R^6$ represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an arylalkylated aldose residue having, substituted for the hydrogen atom of the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated aldohexuronic amide residue having, substituted for the hydrogen atom of the hydroxyl group of the sugar, an arylalkyl group with 7 to 8 carbon atoms, an arylalkylated aldohexuronic acid residue having, substituted for the hydrogen atom of the hydroxyl group of the sugar, an arylalkyl group with 7 to 8 carbon atoms, or an arylalkylated N-acrylaminaldose residue having an amino group substituted with an acyl group with 2 to 4 carbon atoms and having, substituted for the hydrogen atom of the hydroxyl group of the sugar, an arylalkyl group with 7 to 8 carbon atoms; and $Z^\ominus$ is a pharmaceutically acceptable inorganic or organic acid anion, which comprises hydrolyzing the ellipticine derivative having the formula (Ib):

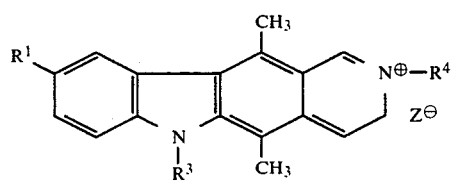

wherein $R^3$ and $Z^\ominus$ are as defined above, $R^1$ represents a hydrogen atom, a hydroxyl group, an alkoxyl group having 1 to 4 carbon atoms, or an acyloxy group having 2 to 7 carbon atoms; and $R^4$ represents an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid ester residue having substituted for the hydrogen atom of the hydroxyl group of the sugar, an alkylacyl group with 2 to 4 carbon atoms or an arylacyl group with 7 to 9 carbon atoms, an arylalkylated aldose residue having, substituted for the hydrogen atom of the hydroxyl group of the sugar, an arylalkyl group with 7 to 8 carbon atoms, an arylalkylated deoxyaldose residue having substituted for the hydrogen atom or the hydroxyl group of the sugar, an arylalkyl group with 7 to 8 carbon atoms, an arylalkylated N-acylaminoaldose residue having an amino group with an acyl group with 2 to 4 carbon atoms and having, substituted for the hydrogen atom of the hydroxyl group of the sugar, an arylalkyl group with 7 to 8 carbon atoms, an arylalkylated aldohexuronic amide residue having substituted for the hydrogen atom of the hydroxyl group of the sugar, an arylalkyl group with 7 to 8 carbon atoms, or an arylalkylated aldohexuronic acid ester residue having substituted for the hydrogen atom of the hydroxyl group of the sugar, an arylalkyl group with 7 to 8 carbon atoms;

in the presence of a base to form the ellipticine derivative having the formula (Ic).

15. A process for producing an ellipticine derivtive having the formula (Id):

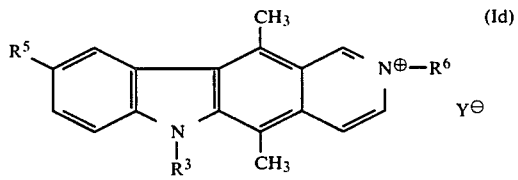

wherein $R^3$ represents a hydrogen atom, a linear, branched, cyclic, or cyclic-linear alkyl group having 1 to 5 carbon atoms;

$R^5$ represents a hydrogen atom, a hydroxyl group, or an alkoxyl group having 1 to 4 carbon atoms; and $R^6$ represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an arylalkylated aldose residue having, substituted for the hydrogen atom or the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated aldohexuronic amide residue having, substituted for the hydrogen atom of the hydroxyl group of the sugar, an arylalkyl group with 7 to 8 carbon atoms, an arylalkylted aldohexuronic acid residue having, substituted for the hydrogen atom of the hydroxyl group of the sugar, an arylalkyl group with 7 to 8 carbon atoms, or an arylalkylated N-acylaminoaldose residue having an amino group substituted with an acyl group with 2 to 4 carbon atoms and having, substituted for the hydrogen atom of the hydroxyl group of the sugar, an arylalkyl group with 7 to 8 carbon atoms; and Y represents a halogen atom, which comprises hydrolyzing the ellipticine derivative having the formula (Ia):

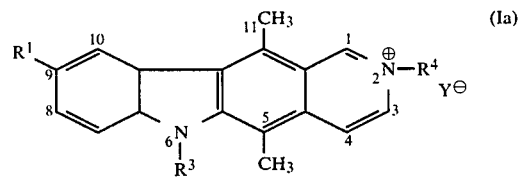

wherein $R^3$ and $Y^\ominus$ are as defined above, $R^1$ represents a hydrogen atom, a hydroxyl group, an alkoxyl group having 1 to 4 carbon atoms, or an acyloxy group having 2 to 7 carbon atoms; and $R^4$ represents an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid ester residue having, substituted for the hydrogen atom of the hydroxyl group of the sugar, an alkylacyl group with 2 to 4 carbon atoms or an arylacyl group with 7 to 9 carbon atoms, an arylalkylated aldose residue having, substituted for the hydrogen atom or the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated N-acylaminoaldose residue having an amino group with an acyl group with 2 to 4 carbon atoms and having, substituted for the hydrogen atom of the hydroxyl group of the sugar, an arylalkyl group with 7 to 8 carbon atoms, an arylalkylated aldohexuronic amide residue having, substituted for the hydrogen atom of the hydroxyl group of the sugar, an arylalkyl group with 7 to 8 carbon atoms, or an arylalkylated aldohexuronic acid ester residue having, substituted for the hydrogen atom of the hydroxyl group of the sugar, an arylalkyl group with 7 to 8 carbon atoms;

and the bond represented by $N^+—R^4$ in the formula (Ia) represents a glycoside bond between a nitrogen atom in the 2-position of the ellipticine and a carbon atom in the 1-position of the sugar, in the presence of a base to form an ellipticine derivative (Id).

16. A process for producing an ellipticine derivative having the formula (Ig):

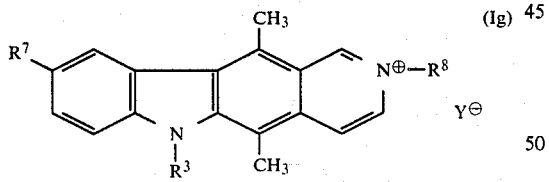

wherein
$R^3$ represents a hydrogen atom, a linear, branched, cyclic, or cyclic-linear alkyl group having 1 to 5 carbon atoms;
$R^7$ represents a hydrogen atom, a hydroxyl group, or an acyloxy group having 2 to 7 carbon atoms, and
$R^8$ represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid residue having, substituted for the hydrogen atom of the hydroxyl group of the sugar, an alkylacyl group with 2 to 4 carbon atoms or an arylacyl group with 7 to 9 carbon atoms, or an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms; and Y represents a halogen atom;

which comprises treating the ellipticine derivative having the formula (Ia):

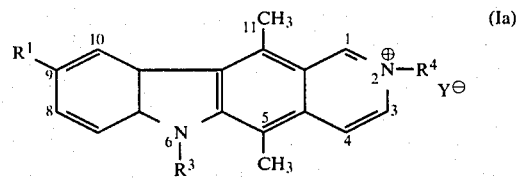

wherein
$R^3$ and $Y^\ominus$ are as defined above,
$R^1$ represents a hydrogen atom, a hydroxyl group, an alkoxyl group having 1 to 4 carbon atoms, or an acyloxy group having 2 to 7 carbon atoms; and
$R^4$ represents an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid ester residue having, substituted for the hydrogen atom of the hydroxyl group of the sugar, an alkylacyl group with 2 to 4 carbon atoms or an arylacyl group with 7 to 9 carbon atoms, an arylalkylated aldose residue having, substituted for the hydrogen atom of the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated N-acylaminoaldose residue having an amino group with an acyl group with 2 to 4 carbon atoms and having, substituted for the hydrogen atom of the hydroxyl group of the sugar, an arylalkyl group with 7 to 8 carbon atoms, an arylalkylated aldohexuronic amide residue having, substituted for the hydrogen atom of the hydroxyl group of the sugar, an arylalkyl group with 7 to 8 carbon atoms, or an arylalkylated aldohexuronic acid ester residue having, substituted for the hydrogen atom of the hydroxyl group of the sugar, an arylalkyl group with 7 to 8 carbon atoms;

and the bond represented by N+—R4 in the formula (Ia) represents a glycoside bond between a nitrogen atom in the 2-position of the elliptiine and a carbon atom in the 1-position of the sugar;

with a trialkyl silyl iodide to form the ellipticine derivative having the formula (Ig).

17. A process for producing an ellipticine derivative having the formula (Ih):

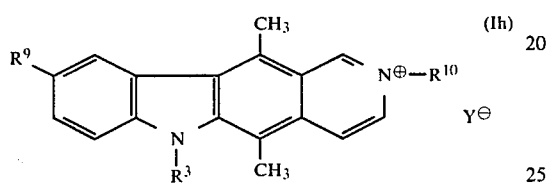

wherein
$R^3$ represents a hydrogen atom, a linear, branched, cyclic, or cyclic-linear alkyl group having 1 to 5 carbon atoms;
$R^9$ represents a hydrogen atom or a hydroxyl group,
$R^{10}$ represents an aldose residue, a deoxyaldose residue, an N-acylaminoaldose residue having a substituted acyl group with 2 to 4 carbon atoms bonded to the N atom, an aldohexuronic amide residue, or an aldohexuronic acid residue, and
$Y^\ominus$ represents a halogen atom;
which comprises hydrolyzing the ellipticine derivative (Ig):

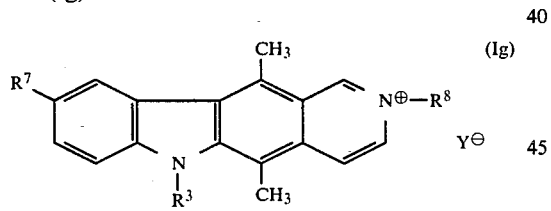

wherein
$R^3$ and Y is as defined above;
$R^7$ represents a hydrogen atom, a hydroxyl group, or an acyloxy group having 2 to 7 carbon atoms, and
$R^8$ represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid residue having, substituted for the hydrogen atom of the hydroxyl group of the sugar, an alkylacyl group with 2 to 4 carbon atoms or an arylacyl group with 7 to 9 carbon atoms, or an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, in the presence of a base to form a ellipticine derivative having the formula (Ih).

18. A process for producing an ellipticine derivative having the formula (If):

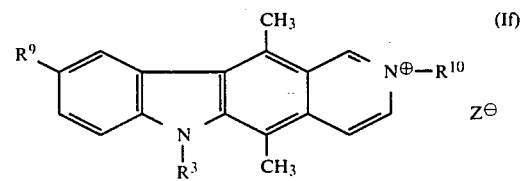

wherein
$R^3$ represents a hydrogen atom, a linear, branched, cyclic, or cyclic-linear alkyl group having 1 to 5 carbon atoms;
$R^9$ represents a hydrogen atom or a hydroxyl group,
$R^{10}$ represents an aldose residue, a deoxyaldose residue, an N-acylaminoaldose residue having a substituted acyl group with 2 to 4 carbon atoms bonded to the N atom, an aldohexuronic amide residue, or an aldohexuronic acid residue, and
$Z^\ominus$ represents a halogen atom; which comprises ion-exchanging the ellipticine derivative having the formula (Ih):

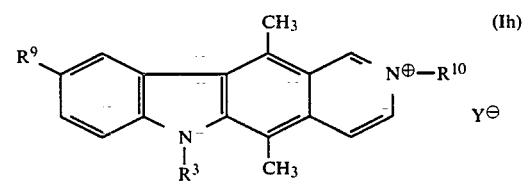

wherein
$R^3$, $R^9$ and $R^{10}$ are as defined above, and
Y represents a halogen atom;
with an ion-exchange resin to form the ellipticine derivative having the formula (If).

19. A process for producing an ellipticine derivative having the formula (Ie):

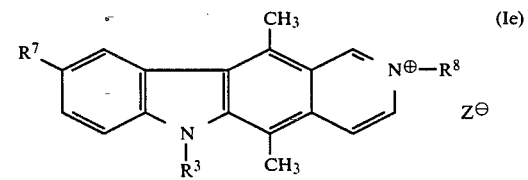

wherein
$R^3$ represents a hydrogen atom, a linear, branched, cyclic, or cyclic-linear alkyl group having 1 to 5 carbon atoms;

R[7] represents a hydrogen atom, a hydroxyl group, or an acyloxy group having 2 to 7 carbon atoms, and R[8] represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylted aldohexuronic acid residue having, substituted for the hydrogen atom of the hydroxyl group of the sugar, an alkylacyl group with 2 to 4 carbon atoms or an arylacyl group with 7 to 9 carbon atoms, or an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, and $Z^\ominus$ is a pharmaceutically acceptable inorganic or organic acid anion which comprises hydroxylizing the ellipticine derivative having the formula (Ib):

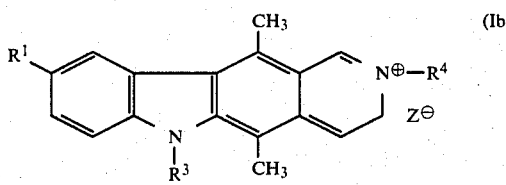

wherein $R^3$ and $Z^\ominus$ are as defined above;

R[1] represents a hydrogen atom, a hydroxyl group, an alkoxyl group having 1 to 4 carbon atoms, or an acyloxy group having 2 to 7 carbon atoms; and R[4] represents an acylated aldose residue having, substituted for the hydrogen atom of the hydroxyl group of the sugar, an alkylacyl group with 2 to 4 carbon atoms or an acryacyl group with 7 to 9 carbon atoms, an acylted deoxyaldose residue having, substituted for the hydrogen atom of the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid ester residue having, substituted for the hydrogen atom of the hydroxyl group of the sugar, an alkylacyl group with 2 to 4 carbon atoms or an arylacyl group with 7 to 9 carbon atoms, an arylalkylated aldose residue having, substituted for the hydrogen atom of the hydroxyl group of the sugar, an arylalkyl group with 7 to 8 carbon atoms, an arylalkylated deoxyaldose residue having, substituted for the hydrogen atom of the hydroxyl group of the sugar, an arylalkyl group with 7 to 8 carbon atoms, an arylalkylated N-acylaminoaldose residue having an amino group with an acyl group with 2 to 4 carbon atoms and having, substituted for the hydrogen atom of the hydroxyl group of the sugar, an arylalkyl group with 7 to 8 carbon atoms, an arylalkylated aldohexuronic amide residue having, substituted for the hydrogen atom of the hydroxyl group of the sugar, an arylalkyl group with 7 to 8 carbon atoms, or an arylalkylated aldohexuronic acid ester residue having, substituted for the hydrogen atom or the hydroxyl group of the sugar, an arylalkyl group with 7 to 8 carbon atoms;

with a trialkyl silyl iodide to form the ellipticine derivative having the formula (Ie).

20. A process for producing an ellipticine derivative having the formula (If):

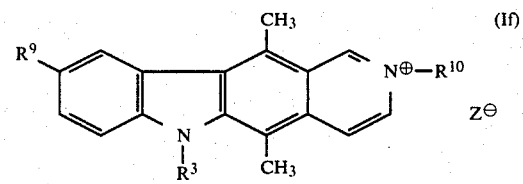

wherein $R^3$ represents a hydrogen atom, a linear, branched, cyclic, or cyclic-linear alkyl group having 1 to 5 carbon atoms;

$R^9$ represents a hydrogen atom or a hydroxyl group, $R^{10}$ represents an aldose residue, a deoxyaldose residue, an N-acylaminoaldose residue having a substituted acyl group with 2 to 4 carbon atoms bonded to the N atom, an aldohexuronic amide residue, or an aldohexuronic acid residue, and $Z^\ominus$ represents a halogen atom;

which comprises hydroxylicin the ellipticine derivative having the formula (Ie):

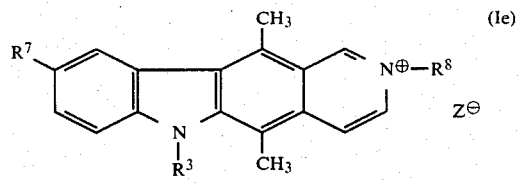

wherein $R^3$ and $Z^\ominus$ are as defined above;

R[7] represents a hydrogen atom, a hydroxyl group, or an acyloxy group having 2 to 7 carbon atoms, and R[8] represents an aldose residue, a deoxyaldose residue, an N-acylaminoaldose residue having a substituted acyl group with 2 to 4 carbon atoms bonded to the N atom, an aldohexuronic amide residue, an aldohexuronic acid residue, an acylated aldose residue having, substituted for the hydrogen atom of the hydroxyl group of the sugar, an alkylacyl group with 2 to 4 carbon atoms or an arylacyl group with 7 to 9 carbon atoms, an acylated deoxyaldose residue having, substituted for the hydrogen atom of the hydroxyl group of the sugar, an alkylacyl group with 2 to 4 carbon atoms or an arylacyl group with 7 to 9 carbon atoms, an acylated aldohexuronic amide residue having, substituted for the hydrogen atom of the hydroxyl group of the sugar, an alkylacyl group with 2 to 4 carbon atoms or an arylacyl group with 7 to 9 carbon atoms, an acylated aldohexuronic acid residue having, substituted for the hydrogen atom of the hydroxyl group of the sugar, an alkylacyl group with 2 to 4 carbon atoms or an arylacyl group with 7 to 9 carbon atoms, an acylated N-acylaminoaldose residue having an amino group substituted with an acyl group with 2 to 4 carbon atoms and having, substituted for the hydrogen atom of the hydroxyl group of the sugar, an alkylacyl group with 2 to 4 carbon atoms or an arylacyl group with 7 to 9 carbon atoms, in the presence of a base to form the ellipticine derivative having the formula (If).

* * * * *